(12) United States Patent
Chen et al.

(10) Patent No.: US 7,795,315 B2
(45) Date of Patent: Sep. 14, 2010

(54) N-(2-AMINO-PHENYL)-AMIDE DERIVATIVES

(75) Inventors: Li Chen, Shanghai (CN); Yun He, Shanghai (CN); Jason Christopher Wong, Shanghai (CN)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 12/358,348

(22) Filed: Jan. 23, 2009

(65) Prior Publication Data

US 2009/0203681 A1 Aug. 13, 2009

(30) Foreign Application Priority Data

Jan. 29, 2008 (EP) .................................. 08150805

(51) Int. Cl.
| | |
|---|---|
| C07C 255/60 | (2006.01) |
| C07C 237/20 | (2006.01) |
| A61K 31/277 | (2006.01) |
| A61K 31/167 | (2006.01) |
| A61K 31/54 | (2006.01) |
| A61K 31/538 | (2006.01) |
| A61K 31/535 | (2006.01) |
| A61K 31/495 | (2006.01) |
| A61K 31/47 | (2006.01) |
| A61K 31/4453 | (2006.01) |
| A61K 31/4402 | (2006.01) |
| A61K 31/4406 | (2006.01) |
| A61K 31/4409 | (2006.01) |
| A61K 31/4192 | (2006.01) |
| A61K 31/40 | (2006.01) |
| A61K 31/381 | (2006.01) |
| A61K 31/341 | (2006.01) |
| A61K 31/351 | (2006.01) |
| C07D 409/12 | (2006.01) |
| C07D 333/24 | (2006.01) |
| C07D 309/06 | (2006.01) |
| C07D 307/54 | (2006.01) |
| C07D 295/155 | (2006.01) |
| C07D 295/15 | (2006.01) |
| C07D 295/185 | (2006.01) |
| C07D 279/12 | (2006.01) |
| C07D 265/34 | (2006.01) |
| C07D 215/14 | (2006.01) |
| C07D 213/56 | (2006.01) |
| C07D 207/09 | (2006.01) |
| C07D 205/04 | (2006.01) |

(52) U.S. Cl. ............ 514/616; 544/168; 544/105; 544/58.1; 544/400; 514/237.8; 514/331; 514/230.5; 514/227.5; 514/237.5; 514/252.12; 514/428; 514/459; 514/330; 514/391; 514/438; 514/313; 514/352; 514/359; 514/471; 514/357; 564/156; 546/234; 546/163; 546/309; 546/337; 548/568; 548/261; 549/426; 549/77; 549/494

(58) Field of Classification Search .................. None
See application file for complete search history.

(56) References Cited

U.S. PATENT DOCUMENTS 3,810,910 A 5/1974 Meyer et al.

FOREIGN PATENT DOCUMENTS

| | | |
|---|---|---|
| DE | 2062265 | 5/1972 |
| FR | 2167954 | 1/1973 |
| WO | WO 01/38322 | 5/2001 |
| WO | WO 2007/087130 | 8/2007 |
| WO | WO 2007/100657 | 9/2007 |

OTHER PUBLICATIONS

Jordan, V. C. Nature Reviews: Drug Discovery, 2, 2003, pp. 205-213.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Golub et al., Science, vol. 286, Oct. 15, 1999, pp. 531-537.*
Koyama et al., Blood vol. 96, 2000, pp. 1490-1495.
Martin et al., Oncogene, 2007, vol. 26 pp. 5450-5467.
Matsuoka et al., Biochemical Pharmacology, 2007, vol. 74 pp. 465-476.

Rastogi et al., Indian J. Chem. Sect. B 21B(5), 1982 pp. 485-487.
Moll et al., Z. Chem. vol. 17, 1977 pp. 133-134.
Hassan et al., Indian J. Chem. vol. 39B, 2000 pp. 764-768.
Bastin et al., Organic Process Research & Development, 2000, vol. 4, pp. 427-435.
Ansel, et al., Pharm. Dosage Forms & Drug Delivery Systems pp. 456-457 (1995).
Zhang, et al., Mol. Cell. Bio. 2004, vol. 24 pp. 5106-5118.
English Language Abstract corresponding to B3 (DE 2062265), 1972.

\* cited by examiner

*Primary Examiner*—Rebecca L Anderson
*Assistant Examiner*—Matthew P Coughlin
(74) *Attorney, Agent, or Firm*—George W. Johnston; Patricia S. Rocha-Tramaloni; Gene J. Yao

(57) ABSTRACT

The present invention provides novel compounds of the general formula (I)

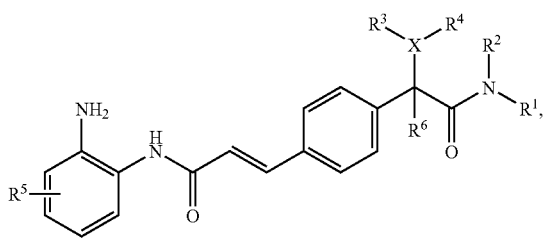

and pharmaceutically acceptable salts thereof, processes for the manufacture of these novel compounds and medicaments containing such compounds. The compounds of the present invention show anti-proliferative and differentiation-inducing activity, which results in inhibition of tumor cell proliferation, induction of apoptosis and inhibition of invasion. The invention also covers the use of such compounds for the treatment of diseases such as cancer and for the manufacture of corresponding medicaments.

4 Claims, 13 Drawing Sheets

N-(2-AMINO-PHENYL)-AMIDE DERIVATIVES

PRIORITY TO RELATED APPLICATION(S)

This application claims the benefit of European Patent Application No. 08150805.3, filed Jan. 29, 2008, which is hereby incorporated by reference in its entirety.

BACKGROUND OF THE INVENTION

The invention relates to novel antitumor agents and pharmaceutically acceptable salts thereof, processes for the manufacture of these novel compounds and medicaments, containing them. The compounds of the invention have antiproliferative and differentiation-inducing activity, which results in inhibition of tumor cell proliferation, induction of apoptosis and inhibition of invasion. The invention concerns thus also the use of such compounds for the treatment of diseases such as cancer and for the manufacture of corresponding medicaments.

The compounds according to this invention are inhibitors of histone deacetylase (HDAC) and therefore show antiproliferative and differentiation-inducing activity, which results in inhibition of tumor cell proliferation, induction of apoptosis and inhibition of invasion.

Transcriptional regulation is a major event in cell differentiation, proliferation, and apoptosis. Transcriptional activation of a set of genes determines cell destination and for this reason transcription is tightly regulated by a variety of factors. One of its regulatory mechanisms involved in the process is an alteration in the tertiary structure of DNA, which affects transcription by modulating the accessibility of transcription factors to their target DNA segments. Nucleosomal integrity is regulated by the acetylation status of the core histones. In a hypoacetylated state, nucleosomes are tightly compacted and thus are nonpermissive for transcription. On the other hand, nucleosomes are relaxed by acetylation of the core histones, with the result being permissiveness to transcription. The acetylation status of the histones is governed by the balance of the activities of histone acetyl transferase (HAT) and histone deacetylase (HDAC). Recently, HDAC inhibitors have been found to arrest growth and induce apoptosis in several types of cancer cells, including colon cancer cells, T-cell lymphoma cells, and erythroleukemic cells. Given that apoptosis is a crucial factor for cancer progression, HDAC inhibitors are promising reagents for cancer therapy as effective inducers of apoptosis (Koyama, Y., et al., Blood 96 (2000) 1490-1495).

Histone deacetylases (HDACs) are the key enzymatic components of multiprotein complexes responsible for deacetylation of lysine residues in histone and nonhistone protein substrates. HDACs can be subdivided into three major classes according to their sequence homology to the yeast HDACs, Rpd3, Hda1, and Sir2. The class I HDACs (HDACs 1, 2, 3, and 8), homologous to Rpd3, localize primarily in the nucleus and appear to be expressed in most tissues. The class II HDACs (HDACs 4, 5, 6, 7, 9, 10), homologous to Hda1, are able to shuttle between the nucleus and the cytoplasm depending on a variety of regulatory signals and cellular state, and have tissue-specific expression patterns. These HDACs can be further subdivided into class IIa (HDACs 4, 5, 7, 9), and class IIb (HDACs 6, 10). The class III HDACs, homologous to Sir2, are NAD$^+$-dependent deacetylases that are mechanistically distinct from the class I and II HDACs and are not inhibited by classical HDAC inhibitors such as trichostatin A, trapoxin B, or SNDX-275. The HDACs can thus be divided into three classes on the basis of sequence similarity, cellular localization tendencies, tissue expression patterns, and enzymatic mechanism.

The class I HDACs in particular have been closely associated with antiproliferative effects against tumor cells. For example, pharmacological inhibition of HDACs 1-3 leads to induction of the cyclin-dependent kinase inhibitor p21 and concomitant cell cycle arrest. The class IIa HDACs are known to associate with the HDAC3/SMRT/N—CoR complex and MEF2 and as such have important roles in regulating muscle cell gene expression (reviewed in *Oncogene* 2007, 26, 5450-5467) and the immune response (*Biochemical Pharmacology* 2007, 74, 465-476). Due to their specific antiproliferative function, selective inhibition of the class I HDACs may be desirable to achieve antitumor efficacy with lower toxicity.

The compounds of the present invention show enhanced potency and selectivity toward the class I HDACs over the class IIa HDACs. This potency and selectivity is evaluated by reporter gene assays that evaluate HDAC subtype activity in the context of relevant multiprotein complexes present in the cell that are typically absent in enzymatic selectivity assays. Thus, the compounds of the present invention possess in-cell selectivity that can lower toxicity associated with inhibition of the class IIa HDACs.

WO 2007/100657 describes related but structurally different o-phenylenediamine derivatives as cell differentiation inducers. The same type of compounds is also the subject of WO2007/087130. The compounds described in these applications are exclusively o-phenylene derivatives monoacylated with derivatives of benzoic acid. However there remains a need for new compounds with improved therapeutic properties, such as enhanced activity, decreased toxicity, better solubility and/or improved pharmacokinetic profile, to name only a few.

Monoacylated o-phenylenediamines are known in the art as precursors for the preparation of the corresponding benzimidazoles, such preparation methods are e.g. described in DE-A 2 062 265; FR 2 167 954; Rastogi, R., and Sharma, S., Indian J. Chem., Sect. B, 21B (5) (1982) 485-487; Moll, R., et al., Z. Chem. 17 (1977) 133-134; and Hassan, H., et al., Indian J. Chem. 39B (2000) 764-768.

It has been found that the compounds of the present invention are HDAC inhibitors which have anti-proliferative and differentiation-inducing activity, which results in inhibition of tumor cell proliferation, induction of apoptosis and inhibition of invasion. These compounds are therefore useful for the treatment of diseases such as cancer in humans or animals.

SUMMARY OF THE INVENTION

The present invention is directed to a compound of formula (I),

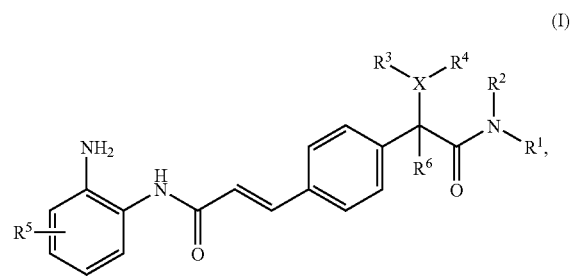

wherein:

X is —N— or —O—;

R[1] and R[2] are each independently selected from the group consisting of: hydrogen; a $C_{1-8}$ alkyl; a 3 to 8 membered mono- or bicyclic cycloalkyl; a 3 to 8 membered mono- or bicyclic heterocyclyl, wherein one, two or three ring atoms are, individually, oxygen, nitrogen, or sulphur; a 6 to 10 membered mono- or bicyclic aryl; and a 5 to 10 membered mono- or bicyclic heteroaryl; whereby all of the aforementioned groups may be unsubstituted or once or several times substituted;

R[3] and R[4] are:

each independently selected from the group consisting of: hydrogen; a $C_{1-8}$ alkyl; a 3 to 8 membered mono- or bicyclic cycloalkyl; a 3 to 8 membered mono- or bicyclic heterocyclyl, wherein one, two or three ring atoms are, individually, oxygen, nitrogen, or sulphur; a 6 to 10 membered mono- or bicyclic aryl; and a 5 to 10 membered mono- or bicyclic heteroaryl; whereby all of the aforementioned groups may be unsubstituted or once or several times substituted; or in instances in which X is —N—, R[3] and R[4] may, together with the nitrogen atom to which they are attached, form a 4- to 6-membered heterocyclyl wherein one ring atom, other than X, may be nitrogen, oxygen, or sulphur;

R[5] is —H or —F; and

R[6] is —H or —CH$_3$; and pharmaceutically acceptable salts of such a compound.

The invention is also directed to a composition comprising such a compound and a method for treating cancer comprising administering the compound to a patient in need of such treatment.

DETAILED DESCRIPTION OF THE INVENTION

Figure 1:
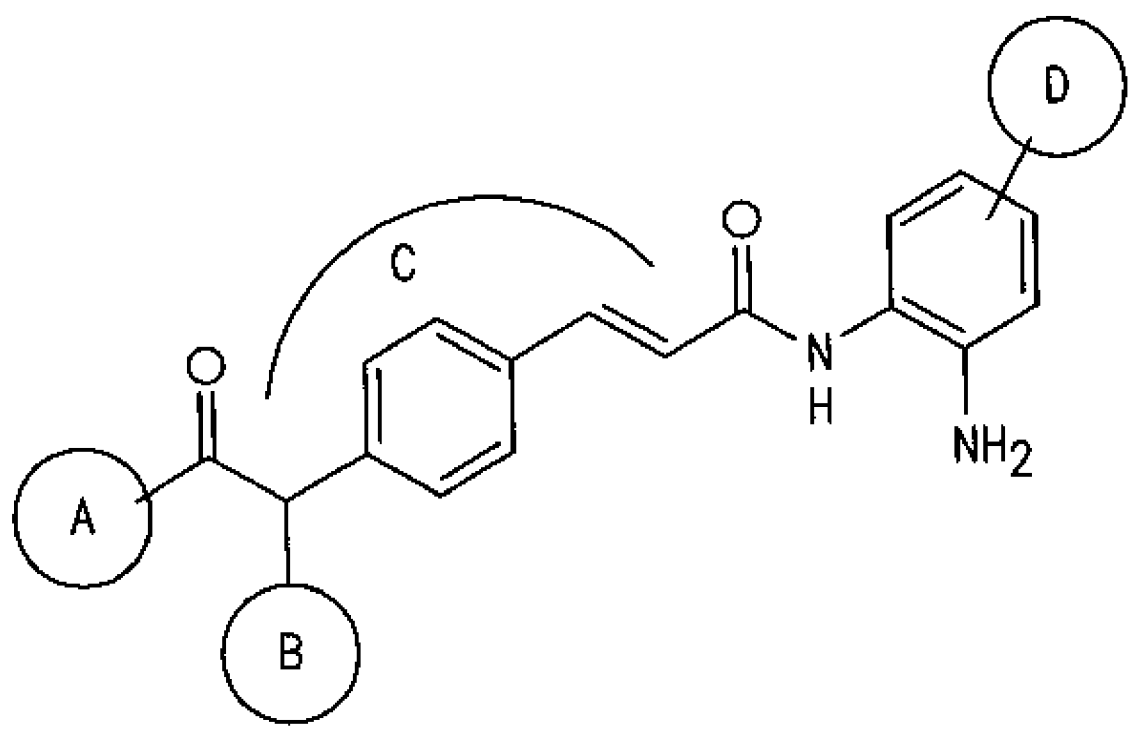
FIG. 1 depicts a general formula for 3-phenyl acrylamides, showing the locations of the A, B, C, and D regions thereof.

The present invention is directed to novel N-(2-Aminophenyl)-amide Derivatives, in particular (E)-N-(2-Aminophenyl)-3-phenyl-acrylamides. More particularly, the present invention discloses compounds of the general formula (I),

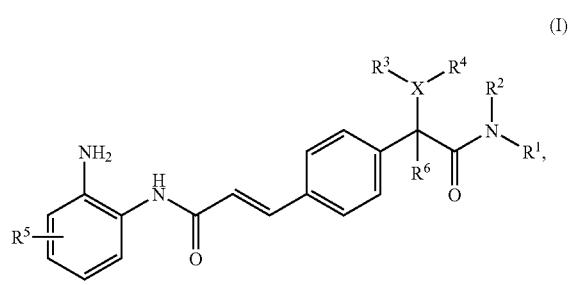

(I)

wherein:

X is —N— or —O—;

R[1] and R[2] are each independently selected from the group consisting of: hydrogen; a $C_{1-8}$ alkyl; a 3 to 8 membered mono- or bicyclic cycloalkyl; a 3 to 8 membered mono- or bicyclic heterocyclyl, wherein one, two or three ring atoms are, individually, oxygen, nitrogen, or sulphur; a 6 to 10 membered mono- or bicyclic aryl; and a 5 to 10 membered mono- or bicyclic heteroaryl; whereby all of the aforementioned groups may be unsubstituted or once or several times substituted;

R[3] and R[4] are:

each independently selected from the group consisting of: hydrogen; a $C_{1-8}$ alkyl; a 3 to 8 membered mono- or bicyclic cycloalkyl; a 3 to 8 membered mono- or bicyclic heterocyclyl, wherein one, two or three ring atoms are, individually, oxygen, nitrogen, or sulphur; a 6 to 10 membered mono- or bicyclic aryl; and a 5 to 10 membered mono- or bicyclic heteroaryl; whereby all of the aforementioned groups may be unsubstituted or once or several times substituted; or in instances in which X is —N—, R[3] and R[4] may, together with the nitrogen atom to which they are attached, form a 4- to 6-membered heterocyclyl wherein one ring atom, other than X, may be nitrogen, oxygen, or sulphur;

R[5] is —H or —F; and

R[6] is —H or —CH$_3$.

The present invention also encompasses pharmaceutically acceptable salts or prodrugs of the compounds of formula I as well as the use of these compounds to produce medicaments.

The term "alkyl", as used herein, denotes a saturated, linear- or branched chain alkyl group containing 1 to 8, preferably 1 to 6, more preferably 1 to 4 carbon-atoms, for example methyl, ethyl, propyl, isopropyl, 1-butyl, 2-butyl, tert-butyl and the like. Preferred alkyl groups have 1, 2 or 3 carbon-atoms.

The term "cycloalkyl", as used herein, means a saturated, cyclic hydrocarbon consisting of one or two rings, which may be fused or attached via a single bond, and containing from 3 to 8, preferably from 3 to 6 carbon atoms. Examples of such 3 to 8 membered cycloalkyl rings are cyclopropyl, cyclobutyl, cyclopentyl, cyclohexyl, cyclooctyl, octahydro-indene, bicyclo[2.2.1]heptane, bicyclohexyl and the like.

The term "heterocyclyl", as used herein, means a 3 to 8 membered mono- or bicyclic ring wherein up to four ring atoms, preferably one, two or three ring atoms are, individually, oxygen, nitrogen or sulphur and the remainder of the ring atoms are carbon. Examples include but are not limited to morpholine, thiomorpholine, piperidine, piperazine, tetrahydro-pyran, 2-Oxa-5-aza-bicyclo[2.2.1]heptane, [1,4]oxathiane, azepane, [1,4]diazepane, pyrrolidine, pyrazolidine, [1,2,3] triazolidine, imidazolidine, thiazolidine, azetidine.

The term "aryl", as used herein, means an aromatic, or partially aromatic, hydrocarbon containing 6 to 10 carbon atoms and consisting of one or two rings, which may be fused or attached via a single bond. Examples are phenyl, biphenyl, indene or naphthyl.

The term "heteroaryl", as used herein, means an aromatic or partially aromatic group consisting of one or two rings, which may be fused or attached via a single bond, and containing 5 to 10 ring atoms wherein up to four, preferably one, two or three ring atoms are, individually, oxygen, nitrogen or sulphur. Examples of such heteroaromatic rings include but are not limited to pyrrole, thiophene, furan, imidazole, pyrazole, triazole, oxazole, osoxazole, isothiazole, pyridine, pyrazine, triazine, tetrazine, quinoline, quinoxaline, chromene, benzoimidazole, indole, benzo[b]thiophene.

The term "halogen", as used herein, means fluorine, chlorine, bromine or iodine.

Compounds of the general formula I which contain one or several chiral centers can either be present in a racemic or in an optically active form. The racemates can be separated according to known methods into the enantiomers. Preferably, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et. al., Organic Process Research & Development 2000, 4, 427-435; or in Ansel, H., et. al., In: Pharmaceutical Dosage Forms and Drug Delivery Systems, 6th ed. (1995), pp. 196 and 1456-1457.

In a preferred embodiment according to the present invention, there is provided a compound of formula (I) as defined above, wherein:
X is —N—;
$R^1$ is hydrogen;
$R^2$ is selected from the group consisting of:
  hydrogen;
  $C_{1-6}$ alkyl, which is unsubstituted or substituted by morpholino;
  —$(CH_2)_k$-phenyl;
  —$(CH_2)_k$-pyridinyl;
  —$(CH_2)_k$-benzotriazolyl;
  —$(CH_2)_k$-cyclohexyl; and
  —$(CH_2)_k$-heterocyclyl, wherein said heterocyclyl is 6 membered and one or two ring atoms are, individually, oxygen, nitrogen or sulphur;
and wherein all of the aforementioned cyclic groups are unsubstituted or one or two times substituted by halogen, cyano, trifluoromethyl, trifluoromethoxy, $C_{1-6}$ alkyl or $C_{3-6}$ cycloalkyl; and
$R^3$ and $R^4$ are:
  each independently selected from the group consisting of:
    hydrogen;
    a 5 to 10 membered, mono- or bicyclic aryl, wherein the ring may be unsubstituted or one or two times substituted by hydroxyl, cyano, halogen, trifluoromethyl, trifluoromethoxy, cyclopropyl, $C_{1-4}$ alkyl, $C_{1-4}$ alkoxy, —$N(C_{1-4}$ alkyl$)_2$ or —$NH(C_{1-4}$alkyl);
    a 5 to 10 membered, mono- or bicyclic heteroaryl wherein 1 or 2 ring atoms are, individually, oxygen, nitrogen or sulphur, and wherein the ring may be unsubstituted or one or two times substituted by hydroxyl, cyano, halogen, trifluoromethyl, trifluoromethoxy, cyclopropyl, $C_{1-4}$ alkyl, $C_{1-4}$ alkoxy, —$N(C_{1-4}$ alkyl$)_2$ or —$NH(C_{1-4}$alkyl);
    a $C_{3-8}$ cycloalkyl; and
    a $C_{1-6}$ alkyl which is unsubstituted or substituted by —OH; —O—$C_{1-6}$ alkyl; —$N(C_{1-6}$ alkyl$)_2$; —NH$(C_{1-6}$ alkyl); —N—C(O)—$C_{1-6}$ alkyl; —C(O)-morpholino; —C(O)—$C_{1-6}$ alkyl; a 5 to 10 membered, mono- or bicyclic aryl which is optionally substituted with methyl or —C(O)—$CH_3$; a 5 to 10 membered, mono- or bicyclic heteroaryl wherein 1, 2 or 3 ring atoms are, individually, oxygen, nitrogen or sulphur, and which is optionally substituted with methyl or —C(O)—$CH_3$; a 3 to 8 membered; mono- or bicyclic cycloalkyl which is optionally substituted with methyl or —C(O)—$CH_3$; or a 3 to 8 membered, mono- or bicyclic heterocyclyl wherein 1, 2 or 3 ring atoms are, individually, oxygen, nitrogen or sulphur, and which is optionally substituted with methyl or —C(O)—$CH_3$; or
  $R^3$ and $R^4$, together with the nitrogen atom to which they are attached, form a 4- to 6-membered heterocyclyl wherein one ring atom, other than X, may be oxygen or nitrogen;
$R^5$ and $R^6$ are each hydrogen; and
k is 0, 1, 2 or 3;

and pharmaceutically acceptable salts of such a compound.

In another preferred embodiment according to the present invention, there is provided a compound of formula (I) as defined above, wherein:
X is —N—;
$R^1$, $R^5$ and $R^6$ are each hydrogen;
$R^2$ is phenyl or pyridinyl, which are either unsubstituted or one or two times substituted by a substituent selected from the group consisting of: halogen; cyano; trifluoromethyl; trifluoromethoxy; $C_{1-6}$ alkyl; and $C_{3-6}$ cycloalkyl; and
$R^3$ is hydrogen and $R^4$ is:
  phenyl, which is unsubstituted or substituted by halogen; or
  a $C_{1-6}$ alkyl, which is unsubstituted or once substituted by a substituent selected from the group consisting of:
    —$N(C_{1-6}$alkyl$)_2$;
    —$NH(C_{1-6}$ alkyl);
    —OH; and a 5 to 7 membered, mono- or bicyclic heterocyclyl, wherein one or two ring atoms are, individually, nitrogen, oxygen or sulphur; or $R^3$ and $R^4$, together with the nitrogen atom to which they are attached, form a 5- to 6-membered heterocyclyl wherein one ring atom, other than X, may be oxygen;

and pharmaceutically acceptable salts of such a compound.

The following specific compounds are especially preferred according to the present invention:

(E)-N-(2-Amino-phenyl)-3-{4-[(4-isopropyl-phenylcarbamoyl)-(2-morpholin-4-yl-propylamino)-methyl]-phenyl}-acrylamide, (E)-N-(2-Amino-phenyl)-3-{4-[(4-tert-butyl-phenylcarbamoyl)-(2-dimethylamino-ethylamino)-methyl]-phenyl}-acrylamide, (E)-N-(2-Amino-phenyl)-3-{4-[(1,1-dimethyl-2-piperidin-1-yl-ethylamino)-(4-trifluoromethyl-phenylcarbamoyl)-methyl]-phenyl}-acrylamide, (E)-N-(2-Amino-phenyl)-3-{4-[(2-morpholin-4-yl-ethoxy)-(4-trifluoromethyl-phenylcarbamoyl)-methyl]-phenyl}-acrylamide, (E)-N-(2-Amino-phenyl)-3-{4-[1-(2-morpholin-4-yl-ethylamino)-1-(4-trifluoromethyl-phenylcarbamoyl)-ethyl]-phenyl}-acrylamide, (E)-N-(2-Amino-5-fluoro-phenyl)-3-{4-[(2-morpholin-4-yl-ethylamino)-(4-trifluoromethyl-phenylcarbamoyl)-methyl]-phenyl}-acrylamide, (E)-N-(2-Amino-phenyl)-3-{4-[(2-morpholin-4-yl-ethylamino)-(4-trifluoromethyl-phenylcarbamoyl)-methyl]-phenyl}-acrylamide, (E)-N-(2-Amino-phenyl)-3-{4-[(2-dimethylamino-ethylamino)-(4-trifluoromethyl-phenylcarbamoyl)-methyl]-phenyl}-acrylamide, (E)-N-(2-Amino-phenyl)-3-{4-[(2-piperidin-1-yl-ethylamino)-(4-trifluoromethyl-phenylcarbamoyl)-methyl]-phenyl}-acrylamide, (E)-N-(2-Amino-phenyl)-3-{4-[(4-cyano-phenylcarbamoyl)-(2-morpholin-4-yl-ethylamino)-methyl]-phenyl}-acrylamide, (E)-N-(2-Amino-phenyl)-3-{4-[(2-morpholin-4-yl-ethylamino)-(4-trifluoromethoxy-phenylcarbamoyl)-methyl]-phenyl}-acrylamide, (E)-N-(2-Amino-phenyl)-3-{4-[(3-morpholin-4-yl-propylamino)-(4-trifluoromethyl-phenylcarbamoyl)-methyl]-phenyl}-acrylamide, (E)-N-(2-Amino-phenyl)-3-{4-[(2-dimethylamino-ethylamino)-(4-trifluoromethoxy-phenylcarbamoyl)-methyl]-phenyl}-acrylamide, (E)-N-(2-Amino-phenyl)-3-{4-[(4-cyano-phenylcarbamoyl)-(2-piperidin-1-yl-ethylamino)-methyl]-phenyl}-acrylamide, (E)-N-(2-Amino-phenyl)-3-{4-[(4-cyano-phenylcarbamoyl)-(2-dimethylamino-ethylamino)-methyl]-phenyl}-acrylamide, (E)-N-(2-Amino-phenyl)-3-(4-{(3-chloro-4-trifluoromethyl-phenylcarbamoyl)-[(1S,4S)-2-(2-oxa-5-aza-bicyclo[2.2.1]hept-5-yl)-ethylamino]-methyl}-phenyl)-acrylamide, (E)-N-(2-Amino-phenyl)-3-(4-{(4-cyclopropyl-phenylcarbamoyl)-[(1S,4S)-2-(2-oxa-5-aza-bicyclo[2.2.1]hept-5-yl)-ethylamino]-methyl}-phenyl)-acrylamide, (E)-N-(2-Amino-phenyl)-3-{4-[(3-chloro-4-trifluoromethyl-phenylcarbamoyl)-(2-piperidin-1-yl-ethylamino)-methyl]-phenyl}-acrylamide, (E)-N-(2-Amino-phenyl)-3-{4-[[(1S,4S)-2-(2-oxa-5-aza-bicyclo[2.2.1]hept-5-yl)-ethylamino]-(4-trifluoromethyl-phenylcarbamoyl)-methyl]-phenyl}-acrylamide, (E)-N-(2-Amino-phenyl)-3-{4-[(4-bromo-phenylcarbamoyl)-(2-thiomorpholin-4-yl-ethylamino)-methyl]-phenyl}-acrylamide, (E)-N-(2-Amino-phenyl)-3-{4-[(2-thiomorpholin-4-yl-ethylamino)-(4-trifluoromethyl-phenylcarbamoyl)-methyl]-phenyl}-acrylamide, (E)-N-(2-Amino-phenyl)-3-{4-[(4-cyclopropyl-phenylcarbamoyl)-(2-thiomorpholin-4-yl-ethylamino)-methyl]-phenyl}-acrylamide, (E)-N-(2-Amino-phenyl)-3-(4-{(2-fluoro-4-trifluoromethyl-phenylcarbamoyl)-[(1S,4S)-2-(2-oxa-5-aza-bicyclo[2.2.1]hept-5-yl)-ethylamino]-methyl}-phenyl)-acrylamide, (E)-N-(2-Amino-phenyl)-3-{4-[(2-dimethylamino-ethylamino)-(4-isopropyl-phenylcarbamoyl)-methyl]-phenyl}-acrylamide, (E)-N-(2-Amino-phenyl)-3-(4-{(4-cyano-phenylcarbamoyl)-[(1S,4S)-2-(2-oxa-5-aza-bicyclo[2.2.1]hept-5-yl)-ethylamino]-methyl}-phenyl)-acrylamide, (E)-N-(2-Amino-phenyl)-3-{4-[(2-piperidin-1-yl-ethylamino)-(5-trifluoromethyl-pyridin-2-ylcarbamoyl)-methyl]-phenyl}-acrylamide, (E)-N-(2-Amino-phenyl)-3-{4-[(2-thiomorpholin-4-yl-ethylamino)-(4-trifluoromethoxy-phenylcarbamoyl)-methyl]-phenyl}-acrylamide, (E)-N-(2-Amino-phenyl)-3-{4-[[(1S,4S)-2-(2-oxa-5-aza-bicyclo[2.2.1]hept-5-yl)-ethylamino]-(5-trifluoromethyl-pyridin-2-ylcarbamoyl)-methyl]-phenyl}-acrylamide, (E)-N-(2-Amino-phenyl)-3-{4-[(2-fluoro-4-trifluoromethyl-phenylcarbamoyl)-(2-morpholin-4-yl-ethylamino)-methyl]-phenyl}-acrylamide, (E)-N-(2-Amino-phenyl)-3-{4-[(4-tert-butyl-phenylcarbamoyl)-(2-morpholin-4-yl-ethylamino)-methyl]-phenyl}-acrylamide, (E)-N-(2-Amino-phenyl)-3-{4-[(2-dimethylamino-ethylamino)-(2-fluoro-4-trifluoromethyl-phenylcarbamoyl)-methyl]-phenyl}-acrylamide, (E)-N-(2-Amino-phenyl)-3-{4-[(4-cyclopropyl-phenylcarbamoyl)-(2-piperidin-1-yl-ethylamino)-methyl]-phenyl}-acrylamide, (E)-N-(2-Amino-phenyl)-3-{4-[(4-isopropyl-phenylcarbamoyl)-(2-thiomorpholin-4-yl-ethylamino)-methyl]-phenyl}-acrylamide, (E)-N-(2-Amino-phenyl)-3-{4-[[(1S,4S)-2-(2-oxa-5-aza-bicyclo[2.2.1]hept-5-yl)-ethylamino]-(4-trifluoromethoxy-phenylcarbamoyl)-methyl]-phenyl}-acrylamide, (E)-N-(2-Amino-phenyl)-3-{4-[(2-dimethylamino-ethylamino)-(5-trifluoromethyl-pyridin-2-ylcarbamoyl)-methyl]-phenyl}-acrylamide, (E)-N-(2-Amino-phenyl)-3-{4-[(3-chloro-4-trifluoromethyl-phenylcarbamoyl)-(2-morpholin-4-yl-ethylamino)-methyl]-phenyl}-acrylamide, (E)-N-(2-Amino-phenyl)-3-{4-[(2-fluoro-4-trifluoromethyl-phenylcarbamoyl)-(2-thiomorpholin-4-yl-ethylamino)-methyl]-phenyl}-acrylamide, (E)-N-(2-Amino-phenyl)-3-{4-[(4-bromo-phenylcarbamoyl)-(2-piperidin-1-yl-ethylamino)-methyl]-phenyl}-acrylamide, (E)-N-(2-Amino-phenyl)-3-{4-[(3-fluoro-4-trifluoromethyl-phenylcarbamoyl)-(2-thiomorpholin-4-yl-ethylamino)-methyl]-phenyl}-acrylamide, (E)-N-(2-Amino-phenyl)-3-{4-[(3-fluoro-4-trifluoromethyl-phenylcarbamoyl)-(2-piperidin-1-yl-ethylamino)-methyl]-phenyl}-acrylamide, (E)-N-(2-Amino-phenyl)-3-{4-[(4-isopropyl-phenylcarbamoyl)-(2-piperidin-1-yl-ethylamino)-methyl]-phenyl}-acrylamide,
(E)-N-(2-Amino-phenyl)-3-{4-[(2-fluoro-4-trifluoromethyl-phenylcarbamoyl)-(2-piperidin-1-yl-ethylamino)-methyl]-phenyl}-acrylamide,
(E)-N-(2-Amino-phenyl)-3-{4-[(3-fluoro-4-trifluoromethyl-phenylcarbamoyl)-(2-morpholin-4-yl-ethylamino)-methyl]-phenyl}-acrylamide,
(E)-N-(2-Amino-phenyl)-3-{4-[(4-isopropyl-phenylcarbamoyl)-(2-morpholin-4-yl-ethylamino)-methyl]-phenyl}-acrylamide,
(E)-N-(2-Amino-phenyl)-3-{4-[(2-thiomorpholin-4-yl-ethylamino)-(5-trifluoromethyl-pyridin-2-ylcarbamoyl)-methyl]-phenyl}-acrylamide,
(E)-N-(2-Amino-phenyl)-3-(4-{(3-fluoro-4-trifluoromethyl-phenylcarbamoyl)-[(1S,4S)-2-(2-oxa-5-aza-bicyclo[2.2.1]hept-5-yl)-ethylamino]-methyl}-phenyl)-acrylamide,
(E)-N-(2-Amino-phenyl)-3-{4-[[(1S,4S)-2-(2-oxa-5-aza-bicyclo[2.2.1]hept-5-yl)-ethylamino]-(6-trifluoromethyl-pyridin-3-ylcarbamoyl)-methyl]-phenyl}-acrylamide,
(E)-N-(2-Amino-phenyl)-3-{4-[(4-cyclopropyl-phenylcarbamoyl)-(3-morpholin-4-yl-propylamino)-methyl]-phenyl}-acrylamide,
(E)-N-(2-Amino-phenyl)-3-{4-[(4-tert-butyl-phenylcarbamoyl)-(2-piperidin-1-yl-ethylamino)-methyl]-phenyl}-acrylamide,
(E)-N-(2-Amino-phenyl)-3-{4-[(2-morpholin-4-yl-ethylamino)-(5-trifluoromethyl-pyridin-2-ylcarbamoyl)-methyl]-phenyl}-acrylamide,
(E)-N-(2-Amino-phenyl)-3-{4-[(3-morpholin-4-yl-propylamino)-(4-trifluoromethoxy-phenylcarbamoyl)-methyl]-phenyl}-acrylamide,
(E)-N-(2-Amino-phenyl)-3-{4-[(2-fluoro-4-trifluoromethyl-phenylcarbamoyl)-(3-morpholin-4-yl-propylamino)-methyl]-phenyl}-acrylamide,
(E)-N-(2-Amino-phenyl)-3-{4-[(4-isopropyl-phenylcarbamoyl)-(3-morpholin-4-yl-propylamino)-methyl]-phenyl}-acrylamide,
(E)-N-(2-Amino-phenyl)-3-{4-[(4-cyclopropyl-phenylcarbamoyl)-(2-morpholin-4-yl-ethylamino)-methyl]-phenyl}-acrylamide,
(E)-N-(2-Amino-phenyl)-3-{4-[(2-piperidin-1-yl-ethylamino)-(4-trifluoromethoxy-phenylcarbamoyl)-methyl]-phenyl}-acrylamide,
(E)-N-(2-Amino-phenyl)-3-{4-[(2-dimethylamino-ethylamino)-(3-fluoro-4-trifluoromethyl-phenylcarbamoyl)-methyl]-phenyl}-acrylamide,
(E)-N-(2-Amino-phenyl)-3-{4-[(4-cyclopropyl-phenylcarbamoyl)-(2-dimethylamino-ethylamino)-methyl]-phenyl}-acrylamide,
(E)-N-(2-Amino-phenyl)-3-{4-[(3-chloro-4-trifluoromethyl-phenylcarbamoyl)-(2-thiomorpholin-4-yl-ethylamino)-methyl]-phenyl}-acrylamide,
(E)-N-(2-Amino-phenyl)-3-{4-[(3-fluoro-4-trifluoromethyl-phenylcarbamoyl)-(3-morpholin-4-yl-propylamino)-methyl]-phenyl}-acrylamide,
(E)-N-(2-Amino-phenyl)-3-{4-[(2-cyano-4-trifluoromethyl-phenylcarbamoyl)-(2-piperidin-1-yl-ethylamino)-methyl]-phenyl}-acrylamide,
(E)-N-(2-Amino-phenyl)-3-{4-[(3-chloro-4-trifluoromethyl-phenylcarbamoyl)-(2-dimethylamino-ethylamino)-methyl]-phenyl}-acrylamide,
(E)-N-(2-Amino-phenyl)-3-{4-[(3-morpholin-4-yl-propylamino)-(5-trifluoromethyl-pyridin-2-ylcarbamoyl)-methyl]-phenyl}-acrylamide,
(E)-N-(2-Amino-phenyl)-3-{4-[(4-cyano-phenylcarbamoyl)-(3-morpholin-4-yl-propylamino)-methyl]-phenyl}-acrylamide,
(E)-N-(2-Amino-phenyl)-3-(4-{(4-isopropyl-phenylcarbamoyl)-[(1S,4S)-2-(2-oxa-5-aza-bicyclo[2.2.1]hept-5-yl)-ethylamino]-methyl}-phenyl)-acrylamide,
(E)-N-(2-Amino-phenyl)-3-{4-[(2-piperidin-1-yl-ethylamino)-(6-trifluoromethyl-pyridin-3-ylcarbamoyl)-methyl]-phenyl}-acrylamide,
(E)-N-(2-Amino-phenyl)-3-{4-[(2-morpholin-4-yl-ethylamino)-(6-trifluoromethyl-pyridin-3-ylcarbamoyl)-methyl]-phenyl}-acrylamide,
(E)-N-(2-Amino-phenyl)-3-{4-[(3-morpholin-4-yl-propylamino)-(6-trifluoromethyl-pyridin-3-ylcarbamoyl)-methyl]-phenyl}-acrylamide,
(E)-N-(2-Amino-phenyl)-3-{4-[(3-chloro-4-trifluoromethyl-phenylcarbamoyl)-(3-morpholin-4-yl-propylamino)-methyl]-phenyl}-acrylamide,
(E)-N-(2-Amino-phenyl)-3-{4-[(4-cyclopropyl-phenylcarbamoyl)-(2-hydroxy-ethylamino)-methyl]-phenyl}-acrylamide,
(E)-N-(2-Amino-phenyl)-3-{4-[(3-chloro-4-trifluoromethyl-phenylcarbamoyl)-(2-hydroxy-ethylamino)-methyl]-phenyl}-acrylamide,
(E)-N-(2-Amino-phenyl)-3-{4-[(4-bromo-phenylcarbamoyl)-(2-hydroxy-ethylamino)-methyl]-phenyl}-acrylamide,
(E)-N-(2-Amino-phenyl)-3-{4-[(2-hydroxy-ethylamino)-(4-isopropyl-phenylcarbamoyl)-methyl]-phenyl}-acrylamide,
(E)-N-(2-Amino-phenyl)-3-{4-[(2-hydroxy-ethylamino)-(4-trifluoromethoxy-phenylcarbamoyl)-methyl]-phenyl}-acrylamide,
(E)-N-(2-Amino-phenyl)-3-{4-[(4-cyano-phenylcarbamoyl)-(2-hydroxy-ethylamino)-methyl]-phenyl}-acrylamide,
(E)-N-(2-Amino-phenyl)-3-{4-[(4-tert-butyl-phenylcarbamoyl)-(2-hydroxy-ethylamino)-methyl]-phenyl}-acrylamide,
(E)-N-(2-Amino-phenyl)-3-{4-[(2-hydroxy-ethylamino)-(4-trifluoromethyl-phenylcarbamoyl)-methyl]-phenyl}-acrylamide,
(E)-N-(2-Amino-phenyl)-3-{4-[(2-fluoro-4-trifluoromethyl-phenylcarbamoyl)-(2-hydroxy-ethylamino)-methyl]-phenyl}-acrylamide,
(E)-N-(2-Amino-phenyl)-3-{4-[(2-hydroxy-ethylamino)-(5-trifluoromethyl-pyridin-2-ylcarbamoyl)-methyl]-phenyl}-acrylamide,
(E)-N-(2-Amino-phenyl)-3-{4-[(2-hydroxy-ethylamino)-(6-trifluoromethyl-pyridin-3-ylcarbamoyl)-methyl]-phenyl}-acrylamide,
(E)-N-(2-Amino-phenyl)-3-(4-{(4-cyano-phenylcarbamoyl)-[methyl-(2-morpholin-4-yl-ethyl)-amino]-methyl}-phenyl)-acrylamide,
(E)-N-(2-Amino-phenyl)-3-(4-{(4-methanesulfonyl-phenylcarbamoyl)-[methyl-(2-morpholin-4-yl-ethyl)-amino]-methyl}-phenyl)-acrylamide,
(E)-N-(2-Amino-phenyl)-3-(4-{(4-isopropyl-phenylcarbamoyl)-[methyl-(2-morpholin-4-yl-ethyl)-amino]-methyl}-phenyl)-acrylamide,
(E)-N-(2-Amino-phenyl)-3-(4-{(4-cyclopropyl-phenylcarbamoyl)-[methyl-(2-morpholin-4-yl-ethyl)-amino]-methyl}-phenyl)-acrylamide,
(E)-N-(2-Amino-phenyl)-3-(4-{(3-chloro-4-trifluoromethyl-phenylcarbamoyl)-[methyl-(2-morpholin-4-yl-ethyl)-amino]-methyl}-phenyl)-acrylamide, (E)-N-(2-Amino-phenyl)-3-(4-{(3-fluoro-4-trifluoromethyl-phenylcarbamoyl)-[methyl-(2-morpholin-4-yl-ethyl)-amino]-methyl}-phenyl)-acrylamide, (E)-N-(2-Amino-phenyl)-3-(4-{(2-fluoro-4-trifluoromethyl-phenylcarbamoyl)-[methyl-(2-morpholin-4-yl-ethyl)-amino]-methyl}-phenyl)-acrylamide, (E)-N-(2-Amino-phenyl)-3-{4-[[methyl-(2-morpholin-4-yl-ethyl)-amino]-(5-trifluoromethyl-pyridin-2-ylcarbamoyl)-methyl]-phenyl}-acrylamide, (E)-N-(2-Amino-phenyl)-3-{4-[(4-bromo-phenylcarbamoyl)-(2-morpholin-4-yl-ethylamino)-methyl]-phenyl}-acrylamide, (E)-N-(2-Amino-phenyl)-3-(4-{(4-tert-butyl-phenylcarbamoyl)-[(1S,4S)-2-(2-oxa-5-aza-bicyclo[2.2.1]hept-5-yl)-ethylamino]-methyl}-phenyl)-acrylamide, (E)-N-(2-Amino-phenyl)-3-{4-[(4-bromo-phenylcarbamoyl)-(2-dimethylamino-ethylamino)-methyl]-phenyl}-acrylamide, (E)-N-(2-Amino-phenyl)-3-{4-[(4-tert-butyl-phenylcarbamoyl)-(2-thiomorpholin-4-yl-ethylamino)-methyl]-phenyl}-acrylamide, (E)-N-(2-Amino-phenyl)-3-{4-[(4-tert-butyl-phenylcarbamoyl)-(2-morpholin-4-yl-2-oxo-ethylamino)-methyl]-phenyl}-acrylamide, (E)-N-(2-Amino-phenyl)-3-{4-[dimethylamino-(4-trifluoromethyl-phenylcarbamoyl)-methyl]-phenyl}-acrylamide, (E)-N-(2-Amino-phenyl)-3-{4-[piperazin-1-yl-(4-trifluoromethyl-phenylcarbamoyl)-methyl]-phenyl}-acrylamide, (E)-N-(2-Amino-phenyl)-3-{4-[(2-morpholin-4-yl-ethylcarbamoyl)-(4-trifluoromethyl-phenylamino)-methyl]-phenyl}-acrylamide, (E)-N-(2-Amino-phenyl)-3-{4-[(4-tert-butyl-phenylcarbamoyl)-(3-morpholin-4-yl-propylamino)-methyl]-phenyl}-acrylamide, (E)-N-(2-Amino-phenyl)-3-{4-[morpholin-4-yl-(4-trifluoromethyl-phenylcarbamoyl)-methyl]-phenyl}-acrylamide, (E)-N-(2-Amino-phenyl)-3-{4-[pyrrolidin-1-yl-(4-trifluoromethyl-phenylcarbamoyl)-methyl]-phenyl}-acrylamide, (E)-N-(2-Amino-phenyl)-3-{4-[(4-tert-butyl-phenylcarbamoyl)-pyrrolidin-1-yl-methyl]-phenyl}-acrylamide, (E)-N-(2-Amino-phenyl)-3-{4-[(4-tert-butyl-phenylcarbamoyl)-((R)-2-morpholin-4-yl-propylamino)-methyl]-phenyl}-acrylamide, (E)-N-(2-Amino-phenyl)-3-{4-[(4-bromo-phenylcarbamoyl)-(3-morpholin-4-yl-propylamino)-methyl]-phenyl}-acrylamide, (E)-N-(2-Amino-phenyl)-3-(4-{(4-tert-butyl-phenylcarbamoyl)-[methyl-(2-morpholin-4-yl-ethyl)-amino]-methyl}-phenyl)-acrylamide, (E)-N-(2-Amino-phenyl)-3-(4-{(4-tert-butyl-phenylcarbamoyl)-[2-(tetrahydro-pyran-4-yl)-ethylamino]-methyl}-phenyl)-acrylamide, (E)-N-(2-Amino-phenyl)-3-{4-[methylamino-(4-trifluoromethyl-phenylcarbamoyl)-methyl]-phenyl}-acrylamide, (E)-N-(2-Amino-phenyl)-3-{4-[[2-(tetrahydro-pyran-4-yl)-ethylamino]-(4-trifluoromethyl-phenylcarbamoyl)-methyl]-phenyl}-acrylamide, (E)-N-(2-Amino-phenyl)-3-{4-[[2-(tetrahydro-pyran-4-yl)-ethylamino]-(4-trifluoromethoxy-phenylcarbamoyl)-methyl]-phenyl}-acrylamide, (E)-N-(2-Amino-phenyl)-3-{4-[azetidin-1-yl-(4-trifluoromethyl-phenylcarbamoyl)-methyl]-phenyl}-acrylamide, (E)-N-(2-Amino-phenyl)-3-{4-[[methyl-(2-morpholin-4-yl-ethyl)-amino]-(4-trifluoromethyl-phenylcarbamoyl)-methyl]-phenyl}-acrylamide, (E)-3-{4-[[2-(4-Acetyl-piperazin-1-yl)-ethylamino]-(4-trifluoromethyl-phenylcarbamoyl)-methyl]-phenyl}-N-(2-amino-phenyl)-acrylamide, (E)-N-(2-Amino-phenyl)-3-{4-[[methyl-(2-morpholin-4-yl-ethyl)-amino]-(4-trifluoromethoxy-phenylcarbamoyl)-methyl]-phenyl}-acrylamide, (E)-3-{4-[[2-(4-Acetyl-piperazin-1-yl)-ethylamino]-(4-trifluoromethoxy-phenylcarbamoyl)-methyl]-phenyl}-N-(2-amino-phenyl)-acrylamide, (E)-N-(2-Amino-phenyl)-3-(4-{(4-bromo-phenylcarbamoyl)-[2-(tetrahydro-pyran-4-yl)-ethylamino]-methyl}-phenyl)-acrylamide, (E)-N-(2-Amino-phenyl)-3-{4-[(2-morpholin-4-yl-2-oxo-ethylamino)-(4-trifluoromethoxy-phenylcarbamoyl)-methyl]-phenyl}-acrylamide, (E)-N-(2-Amino-phenyl)-3-(4-{(4-bromo-phenylcarbamoyl)-[methyl-(2-morpholin-4-yl-ethyl)-amino]-methyl}-phenyl)-acrylamide, (E)-N-(2-Amino-phenyl)-3-{4-[[2-((2R,6S)-2,6-dimethyl-morpholin-4-yl)-ethylamino]-(4-trifluoromethyl-phenylcarbamoyl)-methyl]-phenyl}-acrylamide, (E)-N-(2-Amino-phenyl)-3-{4-[piperidin-1-yl-(4-trifluoromethyl-phenylcarbamoyl)-methyl]-phenyl}-acrylamide, (E)-N-(2-Amino-phenyl)-3-{4-[(2-morpholin-4-yl-2-oxo-ethylamino)-(4-trifluoromethyl-phenylcarbamoyl)-methyl]-phenyl}-acrylamide, (E)-N-(2-Amino-phenyl)-3-{4-[(4-bromo-phenylcarbamoyl)-(2-morpholin-4-yl-2-oxo-ethylamino)-methyl]-phenyl}-acrylamide, (E)-N-(2-Amino-phenyl)-3-{4-[amino-(4-trifluoromethyl-phenylcarbamoyl)-methyl]-phenyl}-acrylamide, (E)-N-(2-Amino-phenyl)-3-[4-(benzylcarbamoyl-phenylamino-methyl)-phenyl]-acrylamide, (E)-N-(2-Amino-phenyl)-3-(4-{isopropylcarbamoyl-[2-(1-methyl-pyrrolidin-2-yl)-ethylamino]-methyl}-phenyl)-acrylamide, (E)-N-(2-Amino-phenyl)-3-(4-{benzylcarbamoyl-[(thiophen-2-ylmethyl)-amino]-methyl}-phenyl)-acrylamide, (E)-N-(2-Amino-phenyl)-3-{4-[cyclohexylcarbamoyl-(4-methoxy-benzylamino)-methyl]-phenyl}-acrylamide, (E)-N-(2-Amino-phenyl)-3-[4-(isobutylamino-isopropylcarbamoyl-methyl)-phenyl]-acrylamide, (E)-N-(2-Amino-phenyl)-3-[4-(isopropylcarbamoyl-phenylamino-methyl)-phenyl]-acrylamide, (E)-N-(2-Amino-phenyl)-3-[4-(cyclohexylcarbamoyl-isopropylamino-methyl)-phenyl]-acrylamide, (E)-N-(2-Amino-phenyl)-3-{4-[benzylcarbamoyl-(quinolin-6-ylamino)-methyl]-phenyl}-acrylamide, (E)-N-(2-Amino-phenyl)-3-{4-[butylcarbamoyl-(quinolin-6-ylamino)-methyl]-phenyl}-acrylamide, (E)-3-{4-[(2-Acetylamino-ethylamino)-(4-chloro-phenylcarbamoyl)-methyl]-phenyl}-N-(2-amino-phenyl)-acrylamide, (E)-N-(2-Amino-phenyl)-3-[4-(cyclohexylcarbamoyl-phenylamino-methyl)-phenyl]-acrylamide, (E)-N-(2-Amino-phenyl)-3-{4-[(4-methoxy-phenylcarbamoyl)-phenylamino-methyl]-phenyl}-acrylamide, (E)-N-(2-Amino-phenyl)-3-{4-[((S)-1-phenyl-ethylcarbamoyl)-(quinolin-6-ylamino)-methyl]-phenyl}-acrylamide, (E)-N-(2-Amino-phenyl)-3-{4-[isopropylcarbamoyl-(naphthalen-2-ylamino)-methyl]-phenyl}-acrylamide, (E)-N-(2-Amino-phenyl)-3-[4-(isopropylamino-isopropyl-carbamoyl-methyl)-phenyl]-acrylamide,
(E)-N-(2-Amino-phenyl)-3-{4-[benzylcarbamoyl-(indan-2-ylamino)-methyl]-phenyl}-acrylamide,
(E)-N-(2-Amino-phenyl)-3-{4-[benzylcarbamoyl-(4-methoxy-phenylamino)-methyl]-phenyl}-acrylamide,
(E)-N-(2-Amino-phenyl)-3-{4-[benzylcarbamoyl-(4-methoxy-benzylamino)-methyl]-phenyl}-acrylamide,
(E)-N-(2-Amino-phenyl)-3-{4-[benzylcarbamoyl-(3-methoxy-benzylamino)-methyl]-phenyl}-acrylamide,
(E)-N-(2-Amino-phenyl)-3-{4-[(4-methoxy-phenylcarbamoyl)-(2-piperidin-1-yl-ethylamino)-methyl]-phenyl}-acrylamide,
(E)-N-(2-Amino-phenyl)-3-{4-[benzylcarbamoyl-(pyridin-3-ylamino)-methyl]-phenyl}-acrylamide,
(E)-N-(2-Amino-phenyl)-3-{4-[cyclohexylcarbamoyl-(4-methoxy-phenylamino)-methyl]-phenyl}-acrylamide,
(E)-N-(2-Amino-phenyl)-3-(4-{[(benzotriazol-1-ylmethyl)-carbamoyl]-[(thiophen-2-ylmethyl)-amino]-methyl}-phenyl)-acrylamide,
(E)-N-(2-Amino-phenyl)-3-[4-(benzylamino-cyclohexylcarbamoyl-methyl)-phenyl]-acrylamide,
(E)-N-(2-Amino-phenyl)-3-(4-{cyclohexylcarbamoyl-[(furan-2-ylmethyl)-amino]-methyl}-phenyl)-acrylamide,
(E)-N-(2-Amino-phenyl)-3-{4-[(4-methoxy-phenylcarbamoyl)-(2-morpholin-4-yl-ethylamino)-methyl]-phenyl}-acrylamide,
(E)-N-(2-Amino-phenyl)-3-[4-(cyclohexylcarbamoyl-isobutylamino-methyl)-phenyl]-acrylamide,
(E)-N-(2-Amino-phenyl)-3-{4-[cyclohexylcarbamoyl-(indan-2-ylamino)-methyl]-phenyl}-acrylamide,
(E)-N-(2-Amino-phenyl)-3-{4-[cyclohexylcarbamoyl-(quinolin-6-ylamino)-methyl]-phenyl}-acrylamide,
(E)-N-(2-Amino-phenyl)-3-{4-[isopropylcarbamoyl-(4-methoxy-phenylamino)-methyl]-phenyl}-acrylamide,
(E)-N-(2-Amino-phenyl)-3-{4-[(4-methoxy-phenylcarbamoyl)-(quinolin-6-ylamino)-methyl]-phenyl}-acrylamide,
(E)-N-(2-Amino-phenyl)-3-{4-[isopropylcarbamoyl-(3-methoxy-benzylamino)-methyl]-phenyl}-acrylamide,
(E)-N-(2-Amino-phenyl)-3-{4-[(4-chloro-phenylcarbamoyl)-(2-morpholin-4-yl-ethylamino)-methyl]-phenyl}-acrylamide,
(E)-N-(2-Amino-phenyl)-3-{4-[isopropylcarbamoyl-(4-isopropyl-phenylamino)-methyl]-phenyl}-acrylamide,
(E)-N-(2-Amino-phenyl)-3-(4-{(4-methoxy-phenylcarbamoyl)-[(thiophen-2-ylmethyl)-amino]-methyl}-phenyl)-acrylamide,
(E)-N-(2-Amino-phenyl)-3-[4-(benzylamino-benzylcarbamoyl-methyl)-phenyl]-acrylamide,
(E)-N-(2-Amino-phenyl)-3-{4-[cyclohexylcarbamoyl-(3-methoxy-benzylamino)-methyl]-phenyl}-acrylamide,
(E)-N-(2-Amino-phenyl)-3-[4-(benzylcarbamoyl-isobutylamino-methyl)-phenyl]-acrylamide,
(E)-N-(2-Amino-phenyl)-3-{4-[benzylcarbamoyl-(cyclohexylmethyl-amino)-methyl]-phenyl}-acrylamide,
(E)-N-(2-Amino-phenyl)-3-{4-[(3-methoxy-phenylcarbamoyl)-(quinolin-6-ylamino)-methyl]-phenyl}-acrylamide,
(E)-N-(2-Amino-phenyl)-3-(4-{[(benzotriazol-1-ylmethyl)-carbamoyl]-cyclopropylamino-methyl}-phenyl)-acrylamide,
(E)-N-(2-Amino-phenyl)-3-(4-{isopropylcarbamoyl-[(thiophen-2-ylmethyl)-amino]-methyl}-phenyl)-acrylamide,
(E)-N-(2-Amino-phenyl)-3-(4-{benzylcarbamoyl-[2-(1-methyl-pyrrolidin-2-yl)-ethylamino]-methyl}-phenyl)-acrylamide,
(E)-N-(2-Amino-phenyl)-3-{4-[(quinolin-6-ylamino)-p-tolylcarbamoyl-methyl]-phenyl}-acrylamide,
(E)-N-(2-Amino-phenyl)-3-{4-[(3-methoxy-phenylcarbamoyl)-(2-morpholin-4-yl-ethylamino)-methyl]-phenyl}-acrylamide,
(E)-N-(2-Amino-phenyl)-3-{4-[(2-morpholin-4-yl-ethylamino)-phenylcarbamoyl-methyl]-phenyl}-acrylamide,
(E)-N-(2-Amino-phenyl)-3-{4-[cyclohexylcarbamoyl-(2-methoxy-ethylamino)-methyl]-phenyl}-acrylamide,
(E)-N-(2-Amino-phenyl)-3-{4-[isopropylcarbamoyl-(quinolin-6-ylamino)-methyl]-phenyl}-acrylamide,
(E)-3-{4-[(Acetyl-quinolin-6-yl-amino)-cyclohexylcarbamoyl-methyl]-phenyl}-N-(2-amino-phenyl)-acrylamide,
(E)-N-(2-Amino-phenyl)-3-{4-[isopropylcarbamoyl-(4-methoxy-benzylamino)-methyl]-phenyl}-acrylamide,
(E)-N-(2-Amino-phenyl)-3-{4-[(4-chloro-phenylcarbamoyl)-(2-hydroxy-ethylamino)-methyl]-phenyl}-acrylamide,
(E)-N-(2-Amino-phenyl)-3-{4-[cyclohexylcarbamoyl-(2-morpholin-4-yl-ethylamino)-methyl]-phenyl}-acrylamide,
(E)-N-(2-Amino-phenyl)-3-[4-(cyclooctylamino-isopropylcarbamoyl-methyl)-phenyl]-acrylamide,
(E)-N-(2-Amino-phenyl)-3-{4-[(2-morpholin-4-yl-ethylamino)-p-tolylcarbamoyl-methyl]-phenyl}-acrylamide,
(E)-N-(2-Amino-phenyl)-3-{4-[(4-methoxy-phenylamino)-(4-methoxy-phenylcarbamoyl)-methyl]-phenyl}-acrylamide,
(E)-N-(2-Amino-phenyl)-3-[4-(benzylcarbamoyl-cyclopentylamino-methyl)-phenyl]-acrylamide,
(E)-N-(2-Amino-phenyl)-3-{4-[cyclohexylcarbamoyl-(cyclohexylmethyl-amino)-methyl]-phenyl}-acrylamide,
(E)-N-(2-Amino-phenyl)-3-{4-[(4-fluoro-phenylcarbamoyl)-(2-morpholin-4-yl-ethylamino)-methyl]-phenyl}-acrylamide,
(E)-N-(2-Amino-phenyl)-3-{4-[benzylcarbamoyl-(naphthalen-2-ylamino)-methyl]-phenyl}-acrylamide,
(E)-N-(2-Amino-phenyl)-3-{4-[benzylcarbamoyl-(3-methoxy-benzylamino)-methyl]-phenyl}-acrylamide,
(E)-N-(2-Amino-phenyl)-3-{4-[benzylamino-(4-methoxy-phenylcarbamoyl)-methyl]-phenyl}-acrylamide,
(E)-N-(2-Amino-phenyl)-3-(4-{benzylcarbamoyl-[(furan-2-ylmethyl)-amino]-methyl}-phenyl)-acrylamide,
(E)-N-(2-Amino-phenyl)-3-[4-(benzylcarbamoyl-cyclopropylamino-methyl)-phenyl]-acrylamide,
(E)-N-(2-Amino-phenyl)-3-(4-{cyclohexylcarbamoyl-[(thiophen-2-ylmethyl)-amino]-methyl}-phenyl)-acrylamide,
(E)-N-(2-Amino-phenyl)-3-{4-[(cyclohexylmethyl-amino)-isopropylcarbamoyl-methyl]-phenyl}-acrylamide,
(E)-N-(2-Amino-phenyl)-3-{4-[(3-chloro-phenylcarbamoyl)-(2-morpholin-4-yl-ethylamino)-methyl]-phenyl}-acrylamide,
(E)-N-(2-Amino-phenyl)-3-{4-[cyclohexylcarbamoyl-(pyridin-3-ylamino)-methyl]-phenyl}-acrylamide,
(E)-N-(2-Amino-phenyl)-3-(4-{cyclohexylcarbamoyl-[(pyridin-4-ylmethyl)-amino]-methyl}-phenyl)-acrylamide,
(E)-N-(2-Amino-phenyl)-3-{4-[cyclohexylcarbamoyl-(naphthalen-2-ylamino)-methyl]-phenyl}-acrylamide,
(E)-N-(2-Amino-phenyl)-3-[4-(cyclohexylcarbamoyl-cyclopropylamino-methyl)-phenyl]-acrylamide,
(E)-N-(2-Amino-phenyl)-3-{4-[(4-isopropyl-phenylamino)-(4-methoxy-phenylcarbamoyl)-methyl]-phenyl}-acrylamide, and
N-({4-[(E)-2-(2-Amino-phenylcarbamoyl)-vinyl]-phenyl}-cyclohexylcarbamoyl-methyl)-4-methoxy-N-(2-morpholin-4-yl-ethyl)-benzamide.

In another embodiment according to the present invention, there is provided a pharmaceutical composition comprising at least one compound as defined herein before together with pharmaceutically acceptable adjuvants.

In another embodiment according to the present invention, there is provided a compound as defined above for use as a medicament.

In still another embodiment according to the present invention, there is provided a compound as defined above for use in the treatment of cancer, in particular hematological malignancies and/or solid tumors, more particularly leukemia, lymphoma, colon, liver, or gastric cancer.

In yet another embodiment according to the present invention, there is provided the use of at least one compound as defined above for the manufacture of medicaments for the treatment of cancer, in particular hematological malignancies and/or solid tumors, more particularly leukemia, lymphoma, colon, liver, or gastric cancer.

Said medicaments, e.g. in the form of pharmaceutical preparations, can be administered orally, e.g. in the form of tablets, coated tablets, dragees, hard and soft gelatin capsules, solutions, emulsions or suspensions. The administration can, however, also be effected rectally, e.g. in the form of suppositories, or parenterally, e.g. in the form of injection solutions.

The above-mentioned pharmaceutical preparations can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage depends on various factors such as manner of administration, species, age and/or individual state of health. The doses to be administered daily are about 5-400 mg/kg, preferably about 10-100 mg/kg, and can be taken singly or distributed over several administrations.

In another preferred embodiment according to the present invention, there is provided a method of treating cancer in a patient comprising administering to said patient at least one compound according to the present invention.

In another preferred embodiment according to the present invention, there is provided a process for the manufacture of the present compounds of formula (I) comprising a reaction as described in any one of schemes 1 to 12 below.

The compounds according to the present invention can be synthesized according to the general reaction schemes 1 to 12, wherein unless explicitly otherwise stated all reactions, reaction conditions, abbreviations and symbols have the meanings well known to a person of ordinary skill in organic chemistry.

The synthetic routes demonstrate how to modify distinct substructural regions of the 3-phenyl-acrylamides. These regions are hereafter referred to as the "A", "B", "C", and "D" regions in the formula depicted in FIG. 1.

Figure 2:
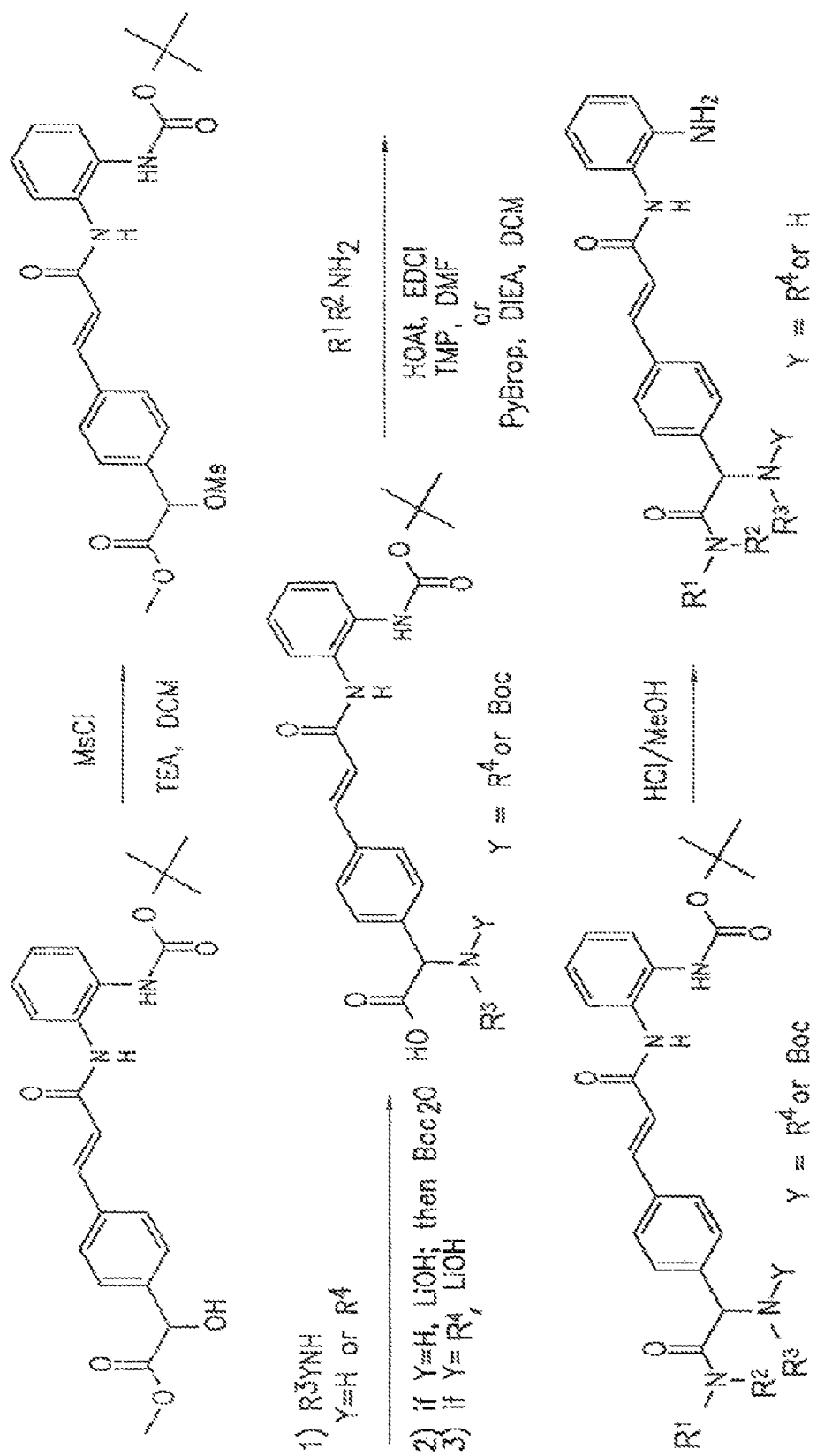
FIG. 2 depicts scheme 1 which is a synthetic route for variation of the A region.
Figure 3:
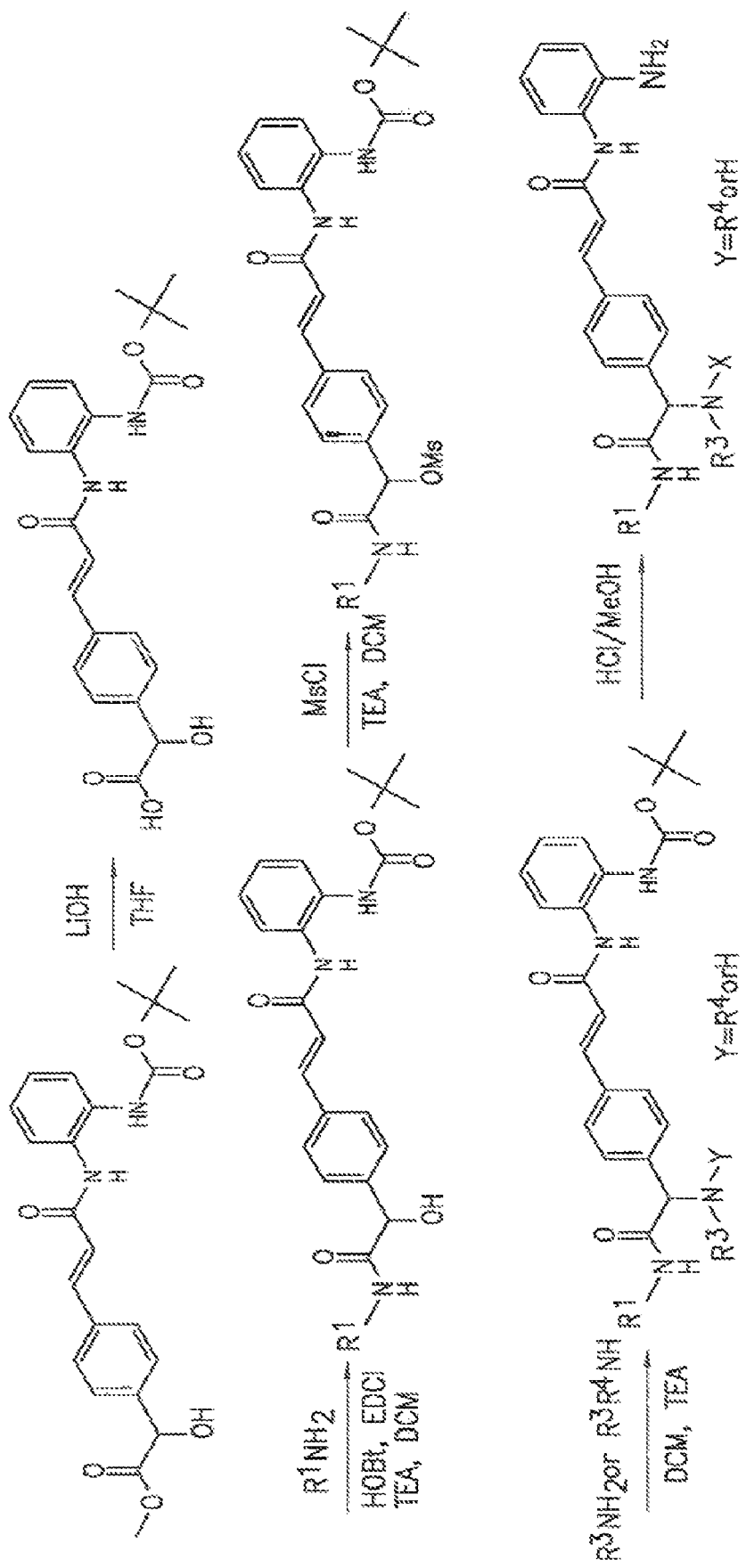
FIG. 3 depicts scheme 2 which is a synthetic route for the variation of the B region.
Figure 4:
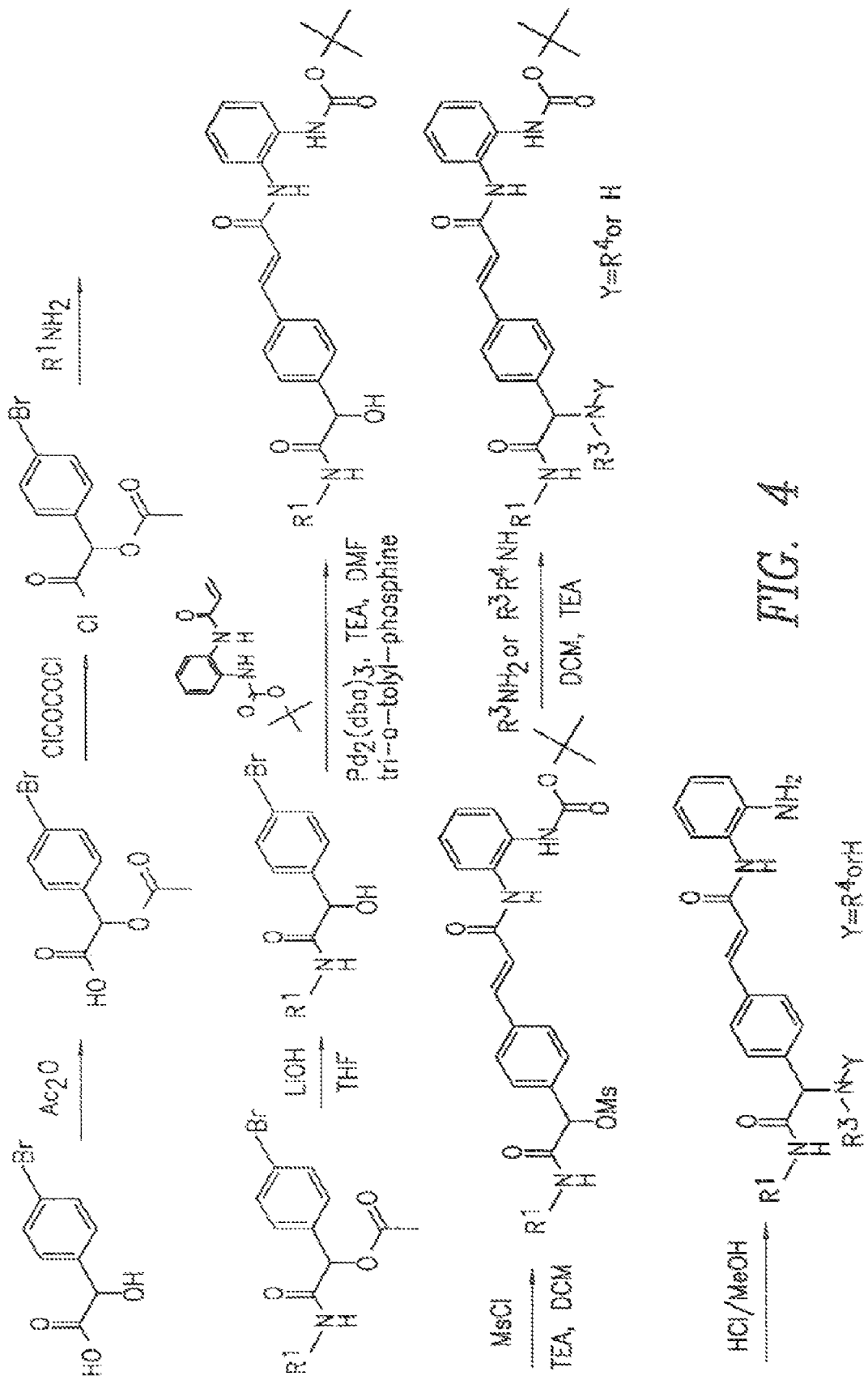
FIG. 4 depicts scheme 3 which is a synthetic route for the variation of the B region.
Figure 5:
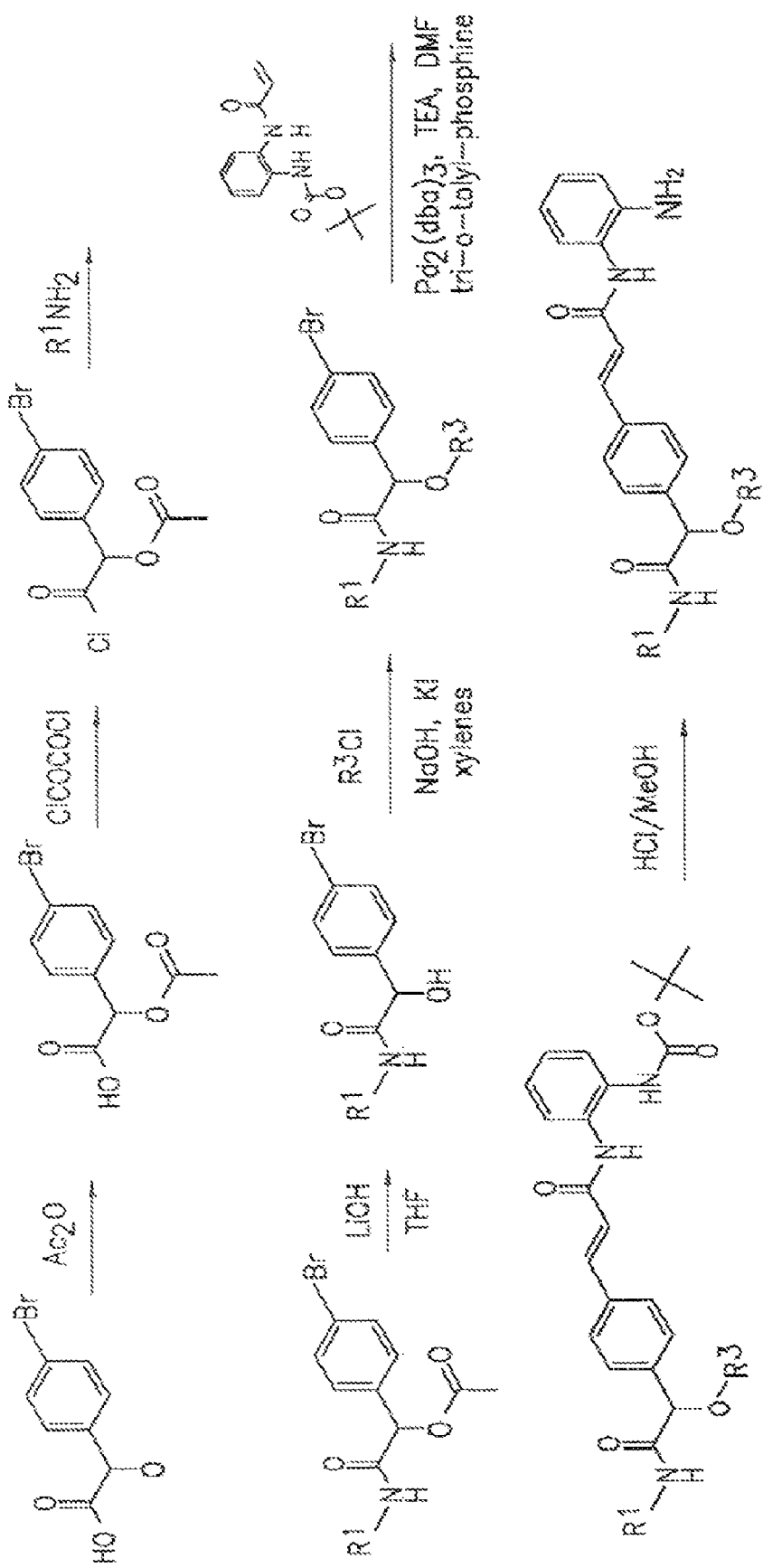
FIG. 5 depicts scheme 4 which is a synthetic route for the variation of the B region.
Figure 6:
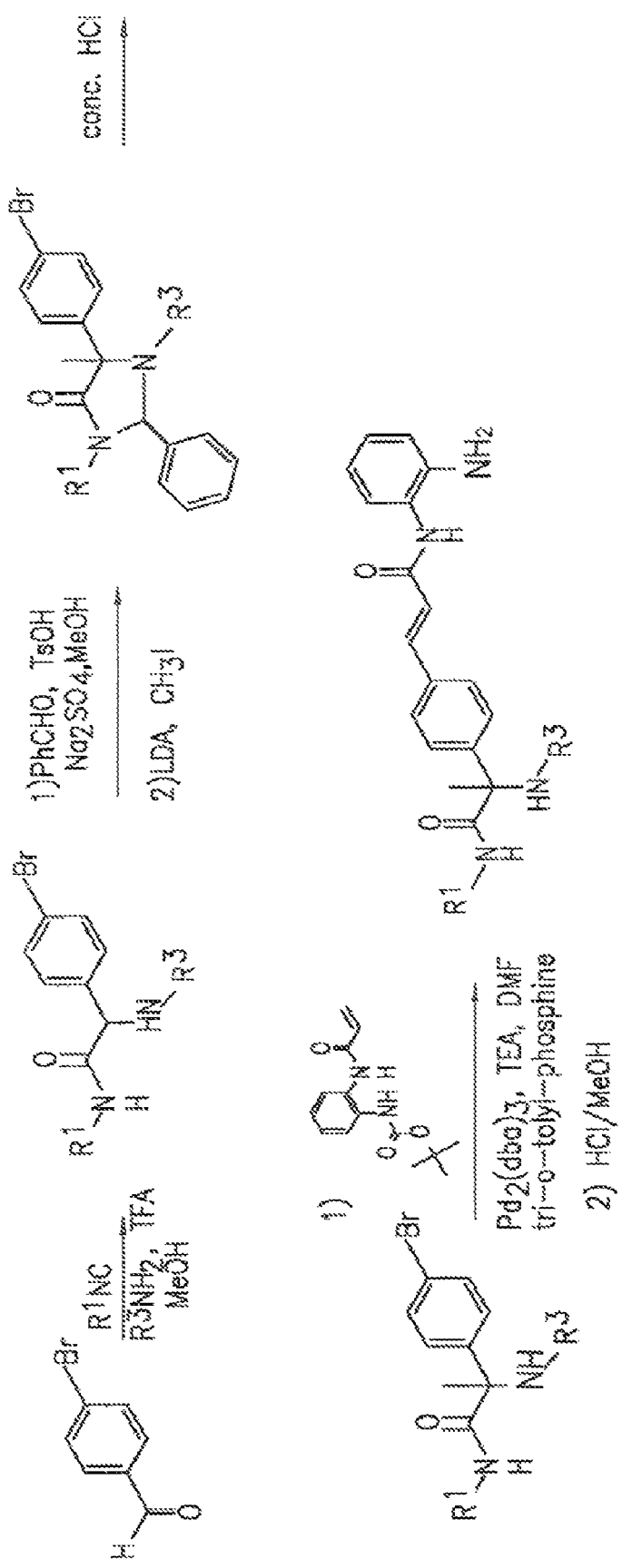
FIG. 6 depicts scheme 5 which is a synthetic route for variation of the C region.
Figure 7:
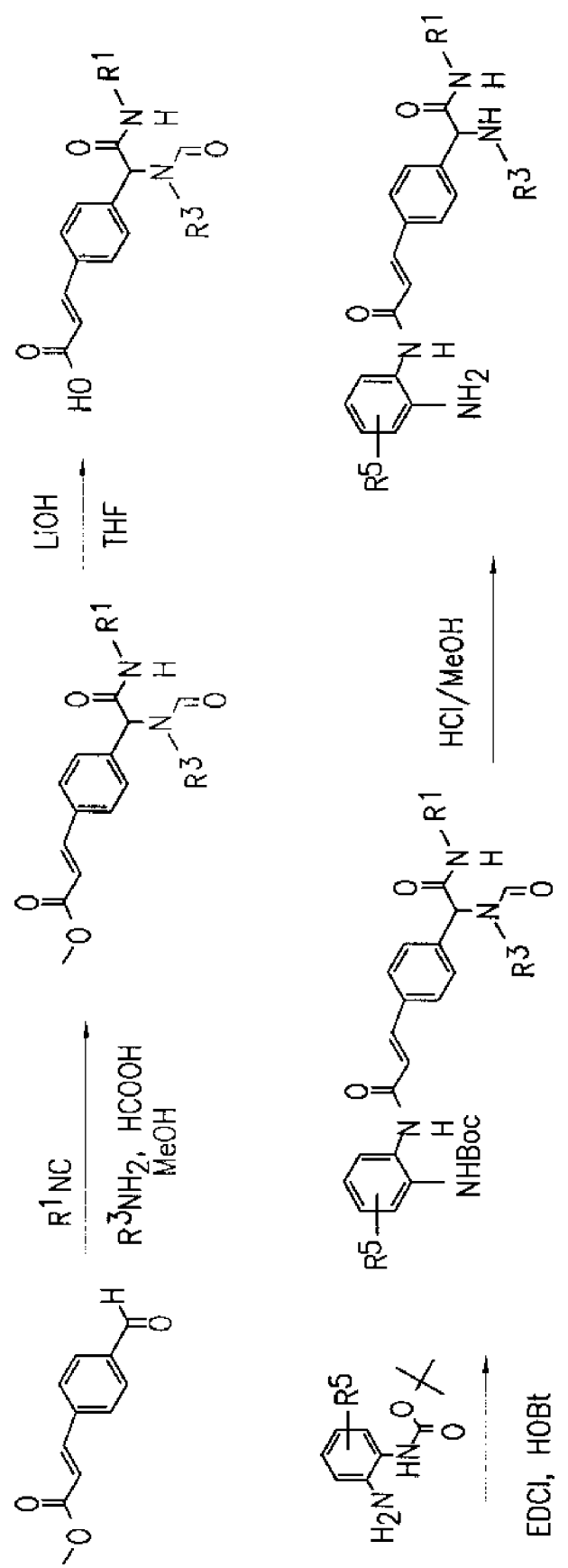
FIG. 7 depicts scheme 6 which is a synthetic route for variation of the D region.
Figure 8:
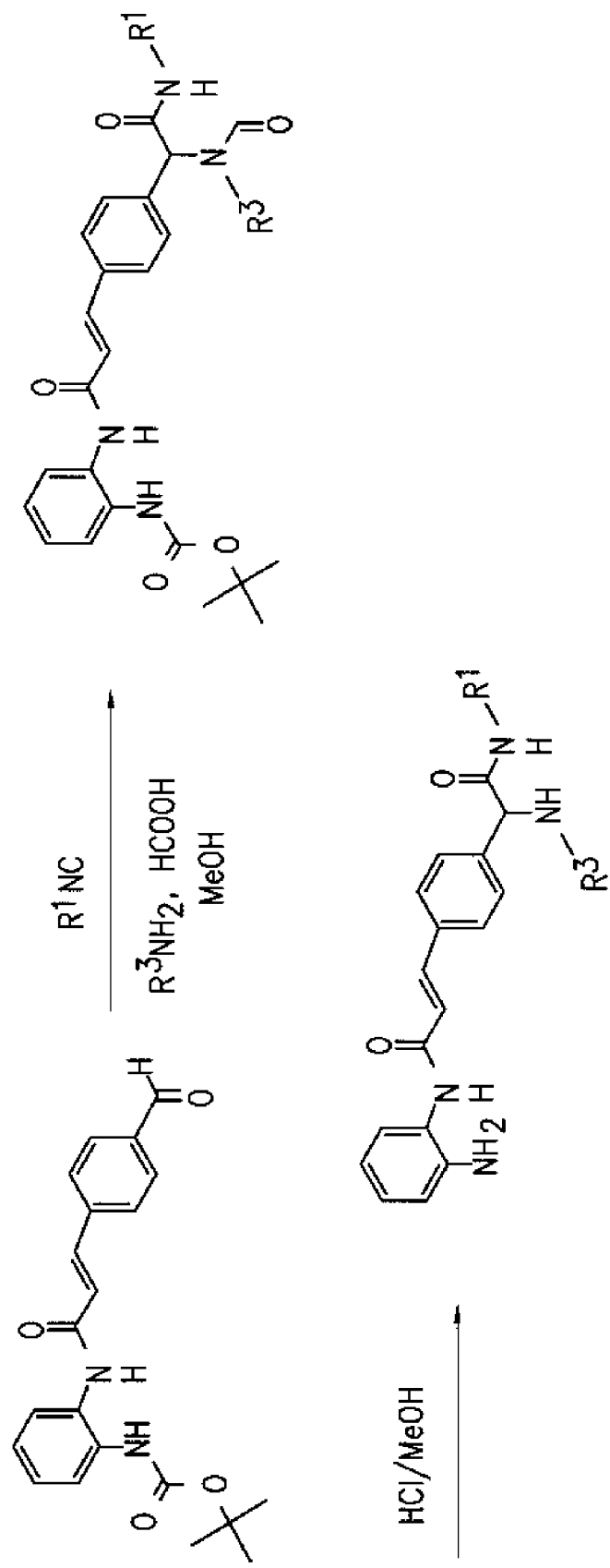
FIG. 8 depicts scheme 7 which is a synthetic route using Ugi chemistry for simultaneous A&B region variation.
Figure 9:
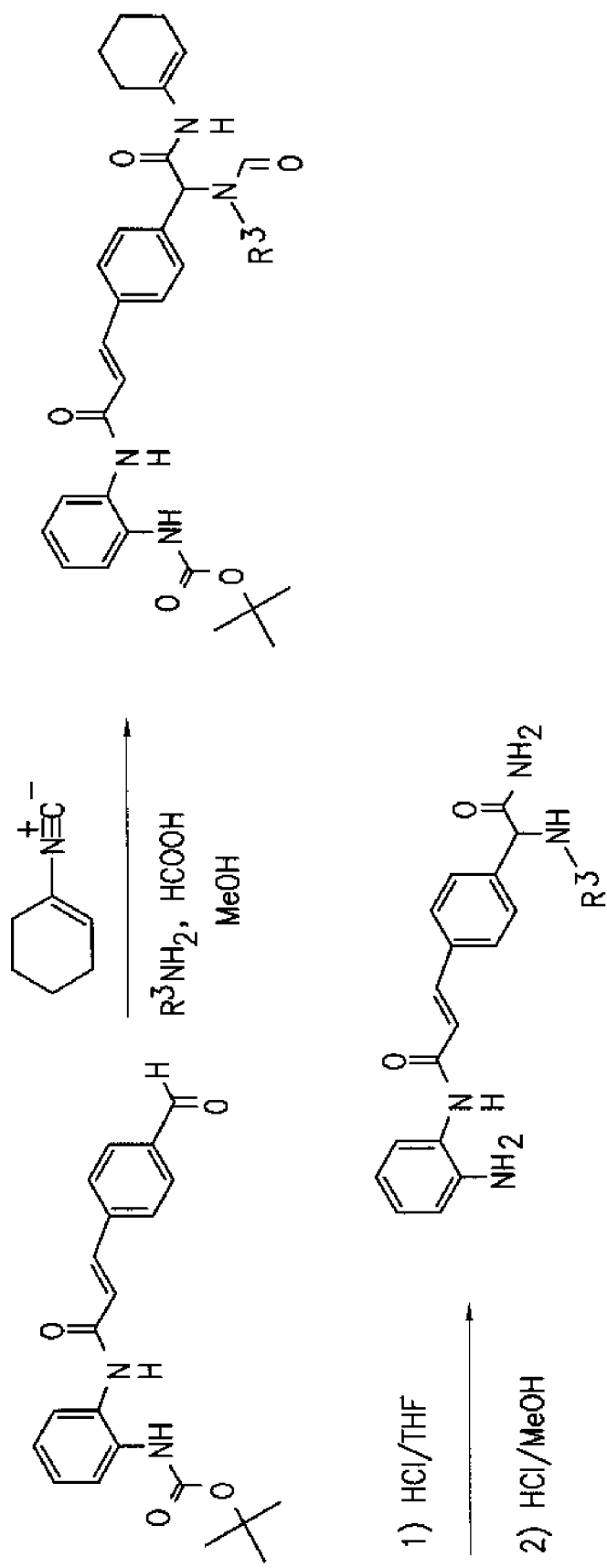
FIG. 9 depicts scheme 8 which is a synthetic route using Ugi chemistry for simultaneous A&B region variation.
Figure 10:
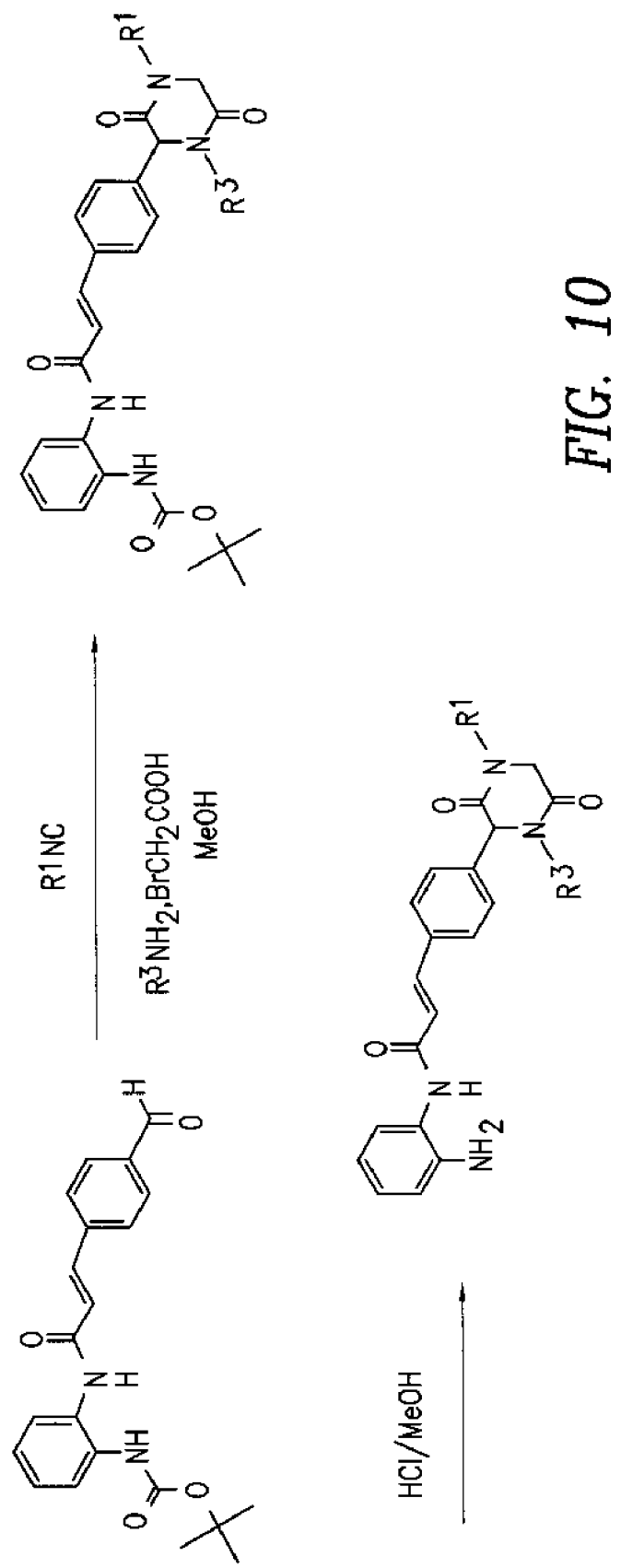
FIG. 10 depicts scheme 9 which is a synthetic route using Ugi chemistry for simultaneous A&B region variation.
Figure 11:
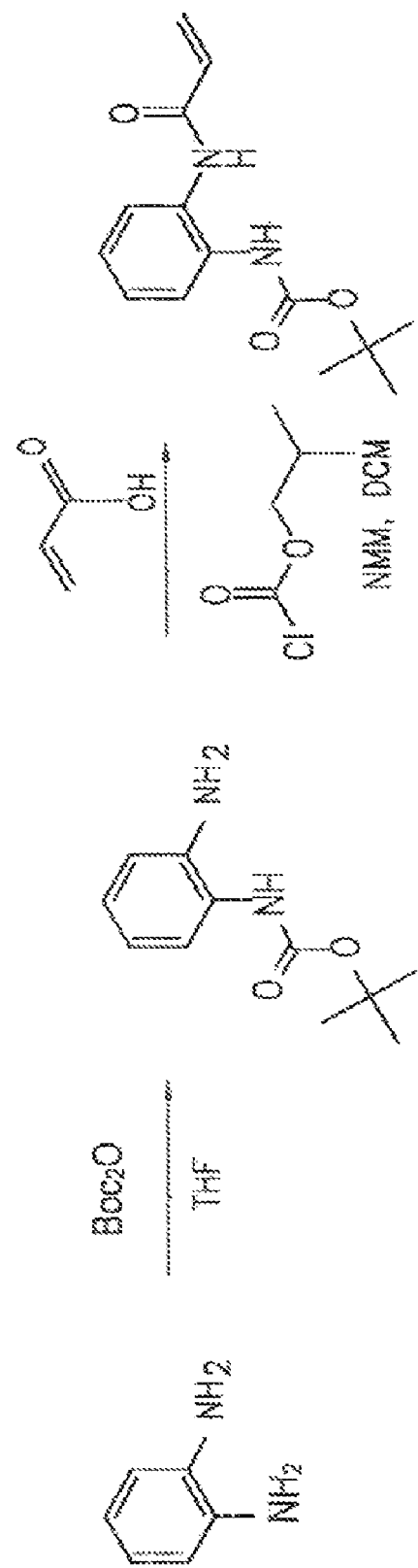
FIG. 11 depicts scheme 10 which is a synthetic route for the synthesis of (2-acryloylamino-phenyl)-carbamic acid tert-butyl ester.
Figure 12:
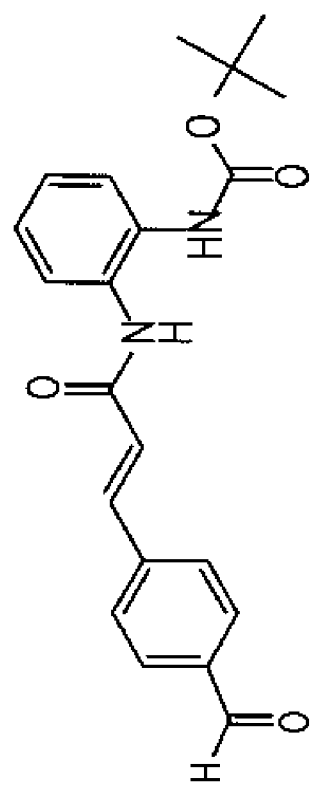
FIG. 12 depicts scheme 11 which is a synthetic route for the synthesis of (E)-{2-[3-(4-Formyl-phenyl)-acryloylamino]-phenyl}-carbamic acid tert-butyl ester.
Figure 12:
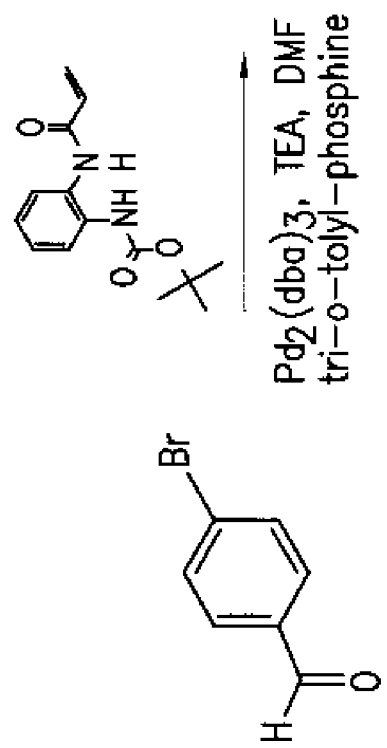
Figure 13:
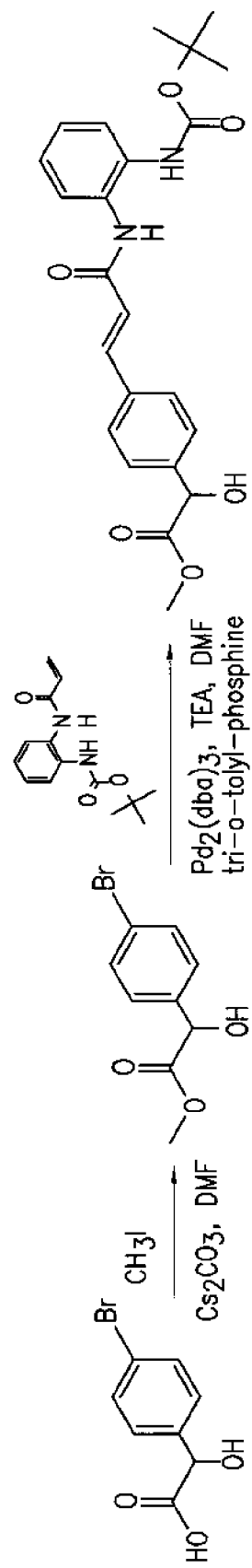
FIG. 13 depicts scheme 12 which is a synthetic route for the synthesis of (E)-{4-[2-(2-tert-Butoxycarbonylamino-phenylcarbamoyl)-vinyl]-phenyl}-hydroxy-acetic acid methyl ester.

Scheme 1 (depicted in FIG. 2) is a synthetic route for variation of the A region. Schemes 2, 3, and 4 (depicted in FIGS. 3, 4, and 5, respectively) are synthetic routes for variation of the B region. Scheme 5 (depicted in FIG. 6) is a synthetic route for variation of the C region. Scheme 6 (depicted in FIG. 7) is a synthetic route for variation of the D region. Schemes 7, 8, and 9 (depicted in FIGS. 8, 9, and 10, respectively) are synthetic routes using Ugi chemistry for simultaneous A&B region variation. Scheme 10 (depicted in FIG. 11) is a synthetic route for the synthesis of (2-acryloylamino-phenyl)-carbamic acid tert-butyl ester. Scheme 11 (depicted in FIG. 12) is a synthetic route for the synthesis of (E)-{2-[3-(4-Formyl-phenyl)-acryloylamino]-phenyl}-carbamic acid tert-butyl ester. Scheme 12 (depicted in FIG. 13) is a synthetic route for the synthesis of (E)-{4-[2-(2-tert-Butoxycarbonylamino-phenylcarbamoyl)-vinyl]-phenyl}-hydroxy-acetic acid methyl ester.

EXAMPLES

The following examples were prepared by the general methods outlined in the schemes above. They are intended to illustrate the meaning of the present invention but should by no means represent a limitation within the meaning of the present invention:

Example 1

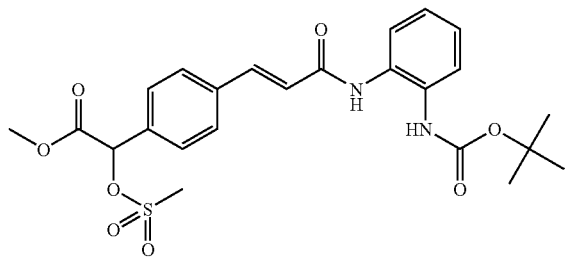

(E)-{4-[2-(2-tert-Butoxycarbonylamino-phenylcarbamoyl)-vinyl]-phenyl}-methanesulfonyloxy-acetic acid methyl ester To a solution of {4-[2-(2-tert-butoxycarbonylamino-phenylcarbamoyl)-vinyl]-phenyl}-hydroxy-acetic acid methyl ester (9.00 g, 21.1 mmol) and triethylamine (3.20 g, 31.6 mmol) in $CH_2Cl_2$ (135 mL) cooled to −5 degrees Celcius was added dropwise methanesulfonyl chloride (3.14 g, 27.4 mmol) under $N_2$ atmosphere. The reaction was stirred at 0 degrees Celcius until the starting material had been consumed according to TLC (about 1 hour). The mixture was washed with water (90 mL) and brine (90 mL), dried with $MgSO_4$, filtered, and evaporated in vacuo to obtain 11.2 g (quantitative yield) of light yellow crystal which was used without further purification. MS: calc'd 505 (MH+), exp 505 (MH+).

Example 2

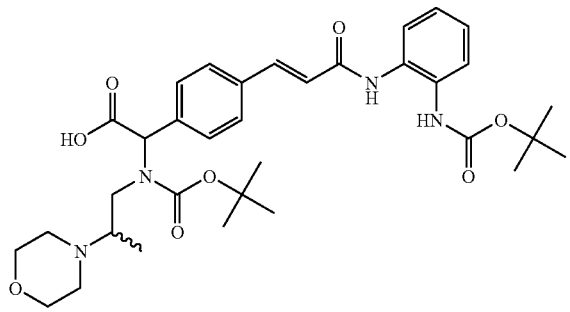

(E)-{4-[2-(2-tert-Butoxycarbonylamino-phenylcarbamoyl)-vinyl]-phenyl}-[tert-butoxycarbonyl-(2-morpholin-4-yl-propyl)-amino]-acetic acid To a solution of (E)-{4-[2-(2-tert-butoxycarbonylamino-phenylcarbamoyl)-vinyl]-phenyl}-methanesulfonyloxy-acetic acid methyl ester (11.40 g, 22.6 mmol) and $K_2CO_3$ (9.37 g, 67.8 mmol) in $CH_3CN$ (250 mL) was added 2-morpholin-4-yl-propylamine (4.08 g, 22.6 mmol) under $N_2$ atmosphere. This mixture was heated to 40 degrees Celcius overnight, cooled to room temperature, and then LiOH solution (1N, 45 mL) was added directly to the mixture. After stirring for about 5 h at room temperature, di-tert-butyl-dicarbonate (13.5 g, 61.9 mmol) was added to the mixture in one portion and stirred overnight. The reaction system was extracted with ethyl acetate (100 mL×4). The combined organic layer was washed with diluted aqueous $Na_2CO_3$ solution (pH~9). The combined aqueous layer was washed with ethyl acetate (50 mL×3) and then acidified with 2 N HCl to pH 6-7. The acidified aqueous layer was extracted with ethyl acetate (100 mL×3). The combined organic layer was washed with brine (50 mL×2), dried with $MgSO_4$, filtered, and evaporated to obtain a yellow solid which was further washed with $Et_2O$ (150 mL) to obtain 10.8 g (75%) of yellow solid product. MS: calc'd 639 (MH+), exp 639 (MH+). $^1$H NMR ($d_6$-DMSO, 400 MHz) δ 9.77 (s, 1H), 8.53 (s, 1H), 7.60 (m, 4H), 7.59 (d, 1H, J=15.6 Hz), 7.48 (m, 2H), 7.14 (m, 2H), 6.94 (d, 1H, J=15.6 Hz), 5.27 (s, 1H), 3.8-3.5 (m, 4H), 2.8 (m, 1H), 2.6-2.2 (m, 6H), 1.5 (broad s, 9H), 1.3 (broad s, 9H), 0.85 (d, 3H, J=6.8 Hz).

Example 3

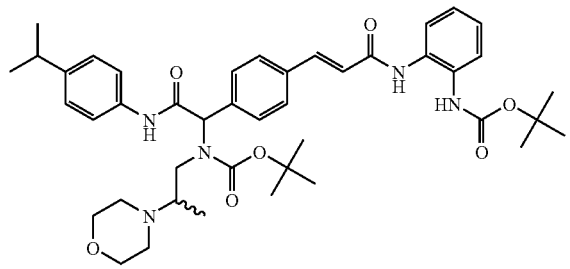

(E)-[2-(3-{4-[[tert-Butoxycarbonyl-(2-morpholin-4-yl-propyl)-amino]-(4-isopropyl-phenylcarbamoyl)-methyl]-phenyl}-acryloylamino)-phenyl]-carbamic acid tert-butyl ester To a solution of (E)-{4-[2-(2-tert-Butoxycarbonylamino-phenylcarbamoyl)-vinyl]-phenyl}-[tert-butoxycarbonyl-(2-morpholin-4-yl-propyl)-amino]-acetic acid (306 mg, 0.480 mmol) and bromo-tris-pyrrolidino-phosphoniumhexafluorophosphate (447 mg, 0.960 mmol) in anhydrous dichloromethane (5 mL) was added diisopropylethylamine (0.167 mL, 0.960 mmol) followed by 4-isopropylaniline (0.131 mL, 0.960 mmol). After stirring at room temperature overnight, the reaction was diluted to 15 mL with dichloromethane, washed with water and brine, dried over $Na_2SO_4$, filtered, and concentrated in vacuo to afford crude product. This material was used without further purification. MS: calc'd 756 (MH+), exp 756 (MH+).

Example 4

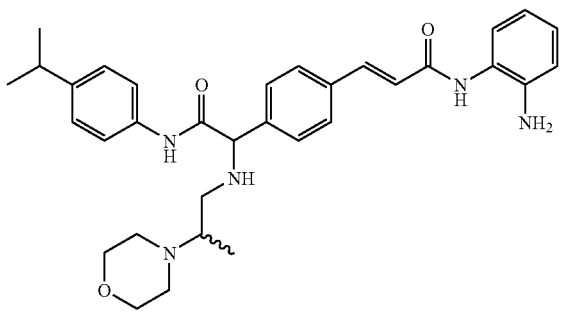

(E)-N-(2-Amino-phenyl)-3-{4-[(4-isopropyl-phenylcarbamoyl)-(2-morpholin-4-yl-propylamino)-methyl]-phenyl}-acrylamide (E)-[2-(3-{4-[[tert-Butoxycarbonyl-(2-morpholin-4-yl-propyl)-amino]-(4-isopropyl-phenylcarbamoyl)-methyl]-phenyl}-acryloylamino)-phenyl]-carbamic acid tert-butyl ester (crude product from Example 3) was dissolved in 1.25M HCl/MeOH (2.9 mL) and stirred at room temperature overnight. The reaction was quenched slowly with solid sodium bicarbonate until the pH was 6-7. The mixture was diluted in acetonitrile with a small amount of dimethylsulfoxide, passed through a 40 μm pipette filter, and then purified by preparative HPLC to obtain 150 mg desired product (56% over two steps). MS: calc'd 556 (MH+), exp 556 (MH+).

$^1$H NMR ($d_6$-DMSO, 400 MHz) δ 10.5 (s, 1H), 9.69 (s, 1H), 7.73 (d, 2H, J=8.0 Hz), 7.65 (d, 2H, J=8.0 Hz), 7.59 (d, 1H, J=15.6 Hz), 7.50 (d, 2H, J=8.4 Hz), 7.37 (d, 1H, J=7.6 Hz), 7.21 (d, 2H, J=8.4 Hz), 7.01 (t, 1H, J=8.0 Hz), 6.95 (d, 1H, J=15.6 Hz), 6.88 (d, 1H, J=8.0 Hz), 6.74 (t, 1H, J=7.2 Hz), 4.95 (s, 1H), 3.79 (broad s, 4H), 3.30 (broad s, 1H), 3.1-2.8 (m, 6H), 1.84 (m, 1H), 1.21 (d, 3H, J=5.6 Hz, major diastereomer), 1.17 (d, 6H, J=6.8 Hz), 1.12 (d, 3H, J=5.6 Hz, minor diastereomer).

The compounds described in the following table 1 were prepared by methods analogous to the synthetic methods described above, but using the appropriate starting materials.

TABLE 1

| Cmpd # | Structure | MW | MS (MH+) calc'd | MS (MH+) exp |
|---|---|---|---|---|
| 4-1 | 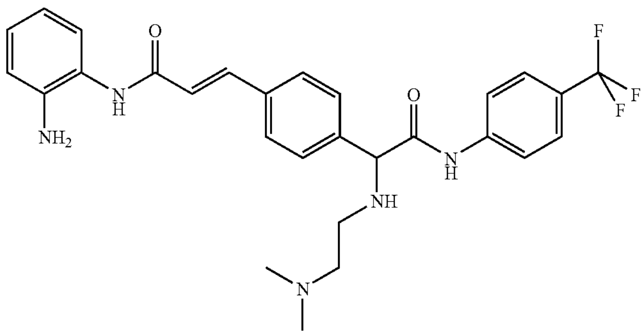 | 525.58 | 526 | 526 |
| 4-2 | 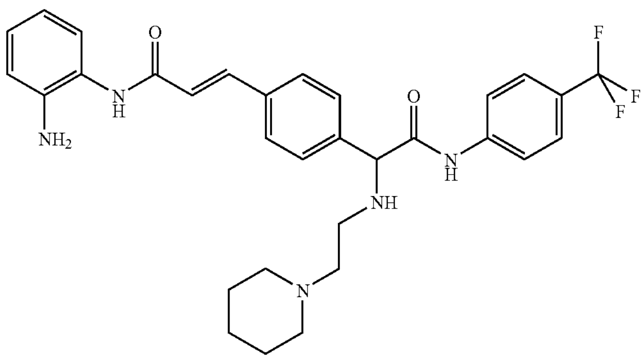 | 565.64 | 566 | 566 |
| 4-3 | 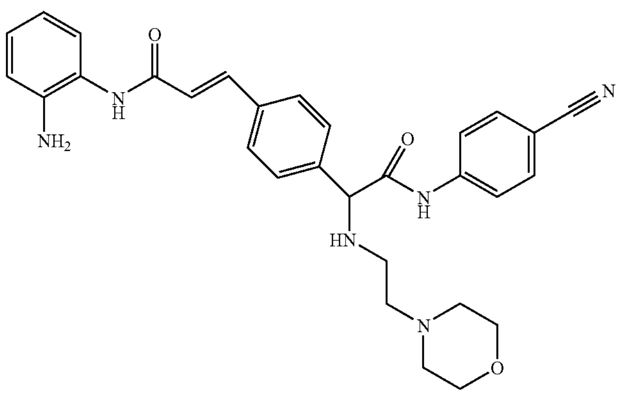 | 524.63 | 525 | 525 |
| 4-4 | 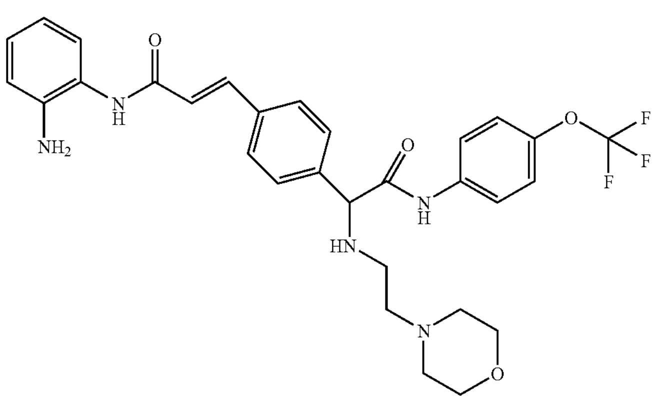 | 583.62 | 584 | 584 |

TABLE 1-continued

| Cmpd # | Structure | MW | MS (MH+) calc'd | MS (MH+) exp |
|---|---|---|---|---|
| 4-5 | 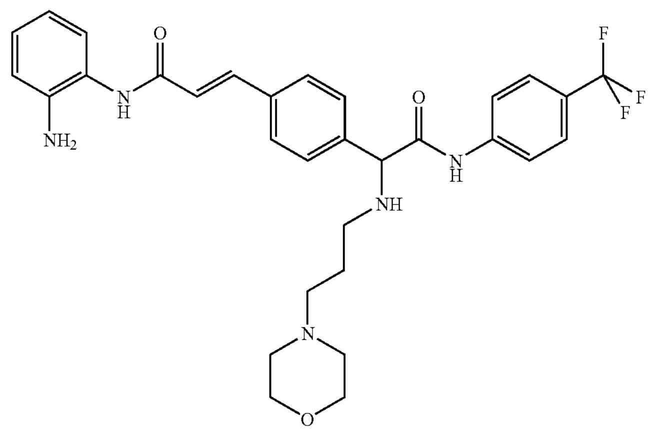 | 581.64 | 582 | 582 |
| 4-6 | 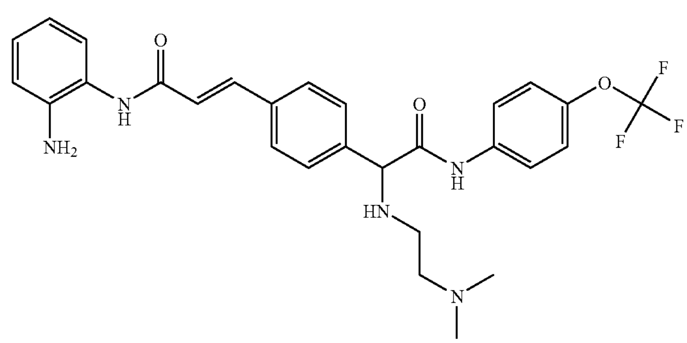 | 541.58 | 542 | 542 |
| 4-7 | 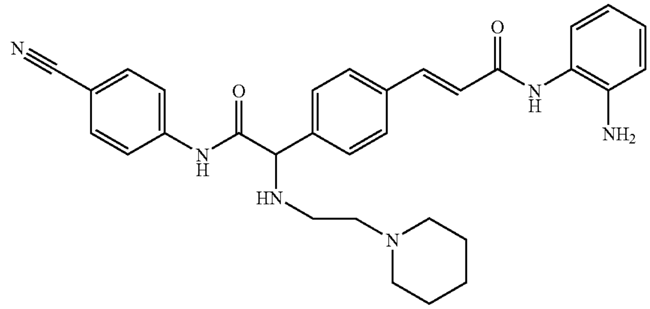 | 522.66 | 523 | 523 |
| 4-8 | 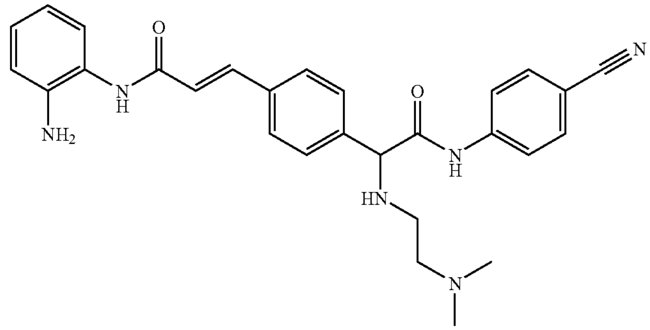 | 482.59 | 483 | 483 |

TABLE 1-continued

| Cmpd # | Structure | MW | MS (MH+) calc'd | MS (MH+) exp |
|---|---|---|---|---|
| 4-9 | 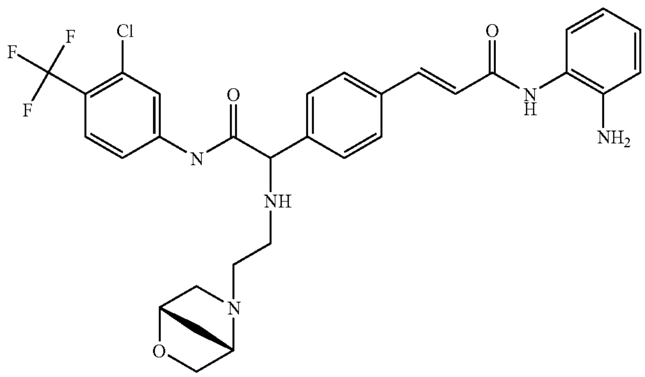 | 614.07 | 614 | 614 |
| 4-10 | 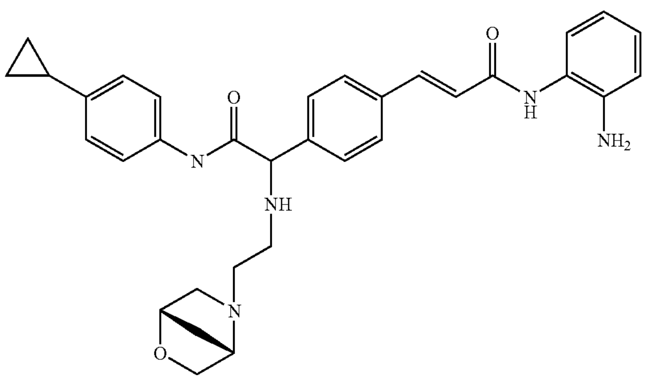 | 551.69 | 552 | 552 |
| 4-11 | 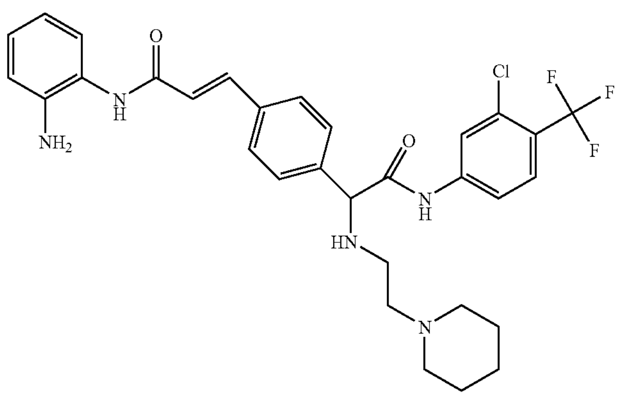 | 600.09 | 600 | 600 |
| 4-12 | 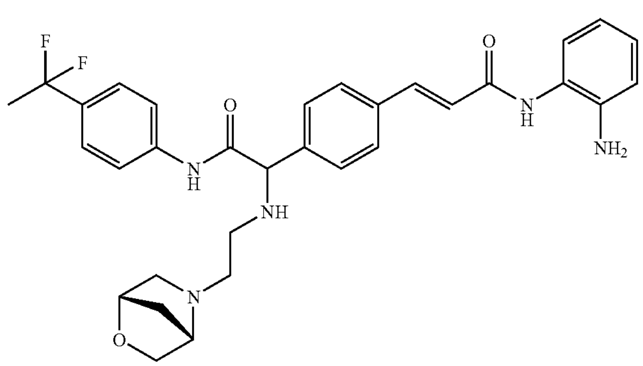 | 579.63 | 580 | 580 |

TABLE 1-continued

| Cmpd # | Structure | MW | MS (MH+) calc'd | MS (MH+) exp |
|---|---|---|---|---|
| 4-13 | 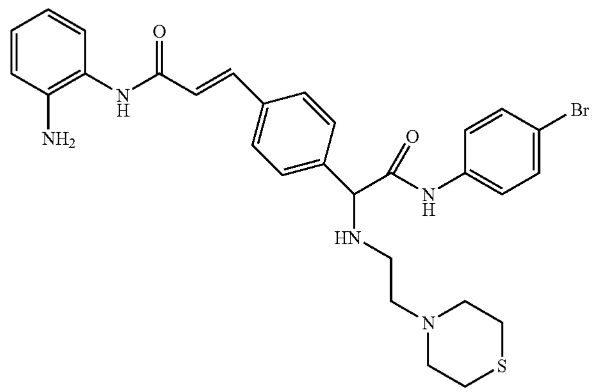 | 594.58 | 594 | 594 |
| 4-14 | 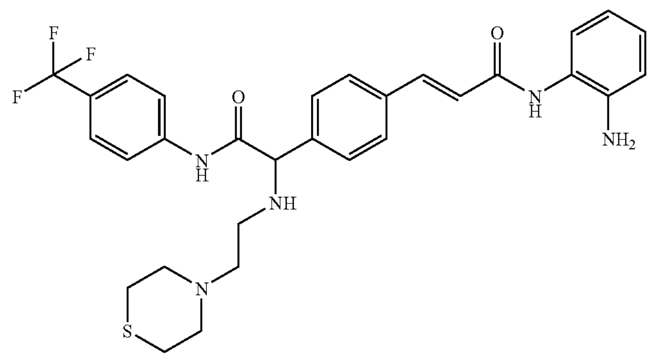 | 583.68 | 584 | 584 |
| 4-15 | 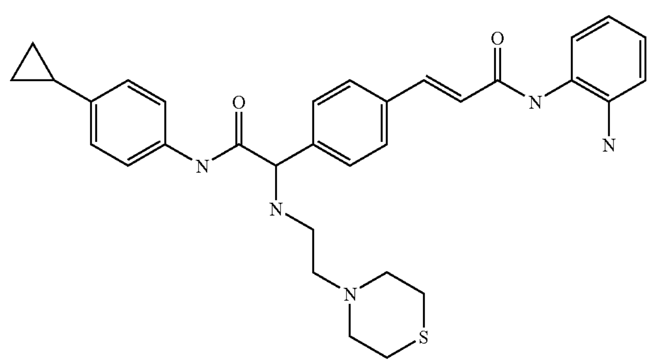 | 555.75 | 556 | 556 |
| 4-16 | 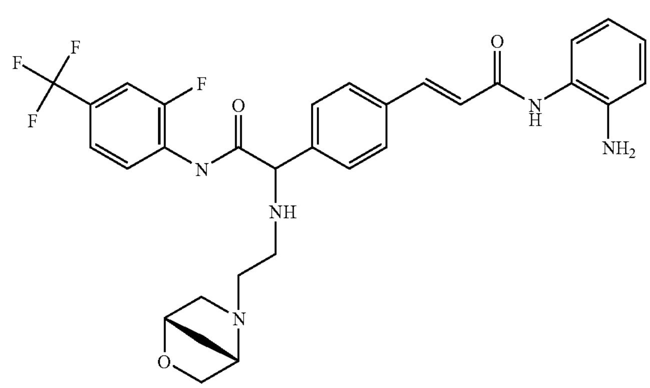 | 597.62 | 598 | 598 |

TABLE 1-continued

| Cmpd # | Structure | MW | MS (MH+) calc'd | MS (MH+) exp |
|---|---|---|---|---|
| 4-17 | 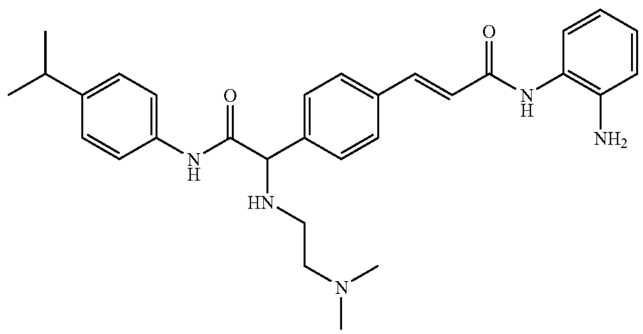 | 499.66 | 500 | 500 |
| 4-18 | 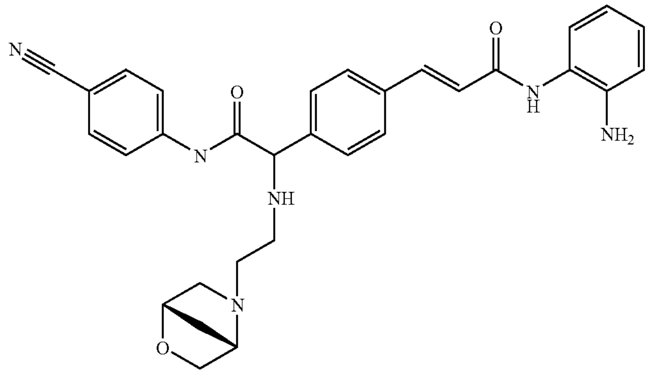 | 536.64 | 537 | 537 |
| 4-19 | 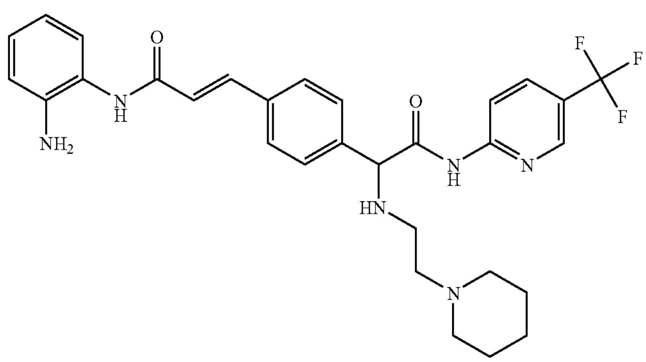 | 566.63 | 567 | 567 |
| 4-20 | 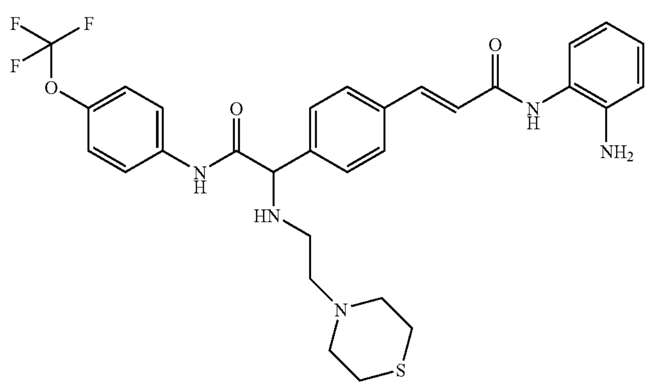 | 599.68 | 600 | 600 |

TABLE 1-continued

| Cmpd # | Structure | MW | MS (MH+) calc'd | MS (MH+) exp |
|---|---|---|---|---|
| 4-21 | 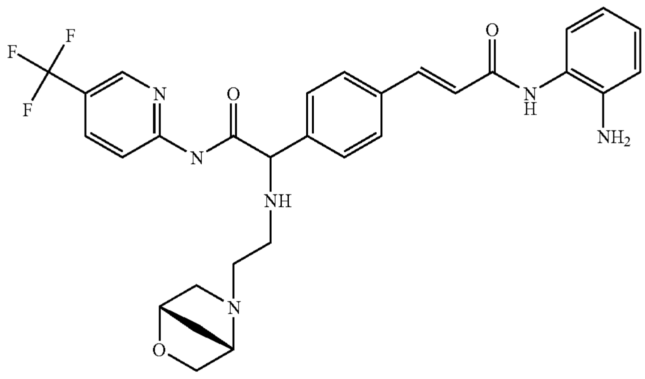 | 580.62 | 581 | 581 |
| 4-22 | 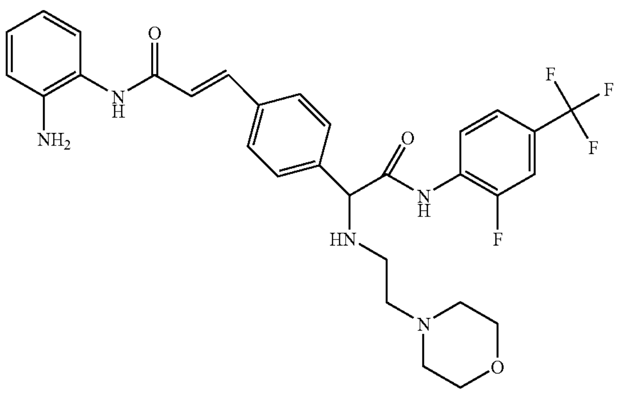 | 585.61 | 586 | 586 |
| 4-23 | 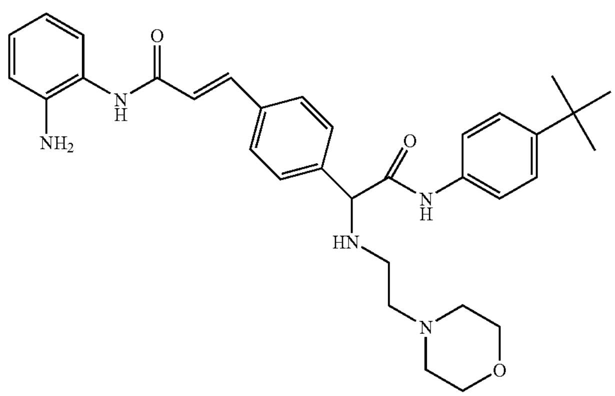 | 555.73 | 556 | 556 |
| 4-24 | 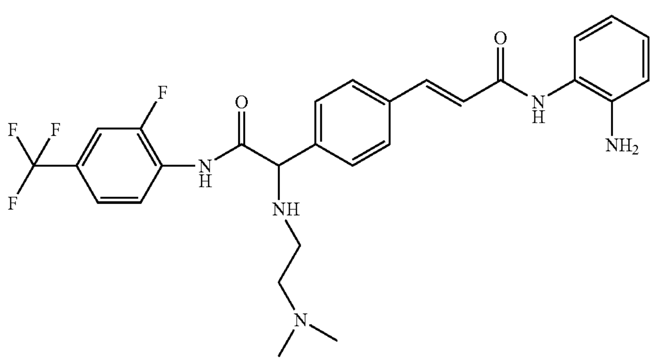 | 543.57 | 544 | 544 |

TABLE 1-continued

| Cmpd # | Structure | MW | MS (MH+) calc'd | MS (MH+) exp |
|---|---|---|---|---|
| 4-25 | 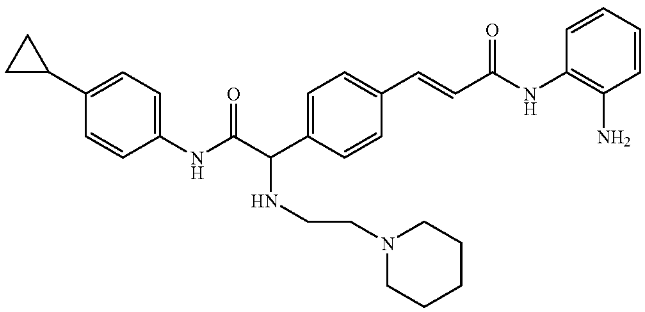 | 537.71 | 538 | 538 |
| 4-26 | 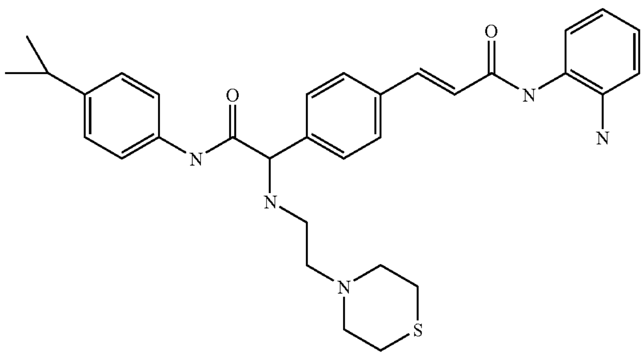 | 557.76 | 558 | 558 |
| 4-27 | 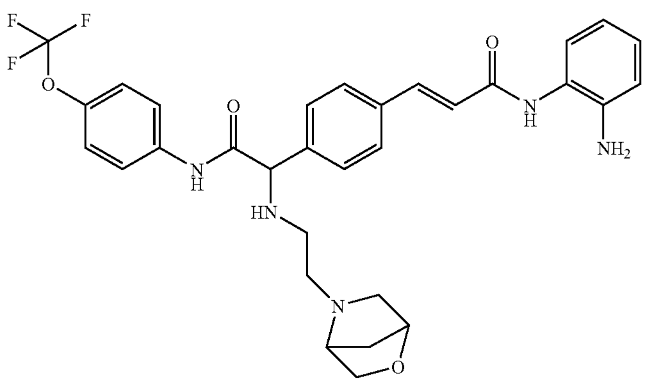 | 595.63 | 596 | 596 |
| 4-28 | 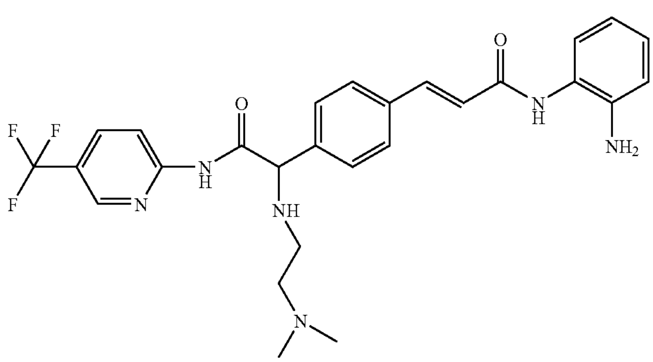 | 526.57 | 527 | 527 |

TABLE 1-continued

| Cmpd # | Structure | MW | MS (MH+) calc'd | MS (MH+) exp |
|---|---|---|---|---|
| 4-29 | 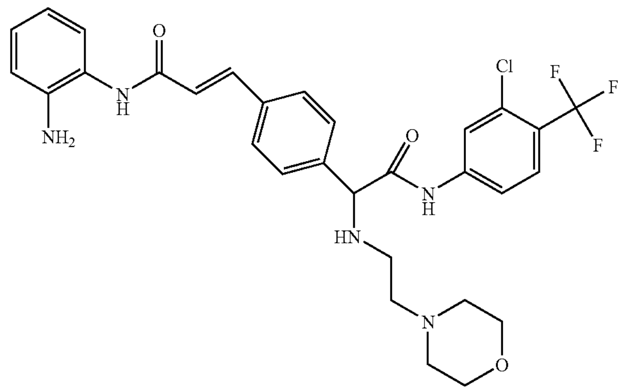 | 602.06 | 602 | 602 |
| 4-30 | 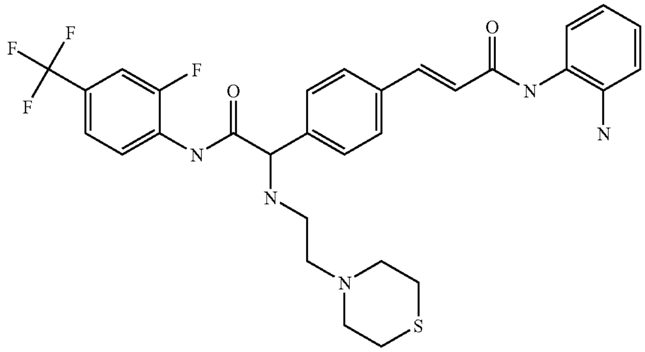 | 601.67 | 602 | 602 |
| 4-31 | 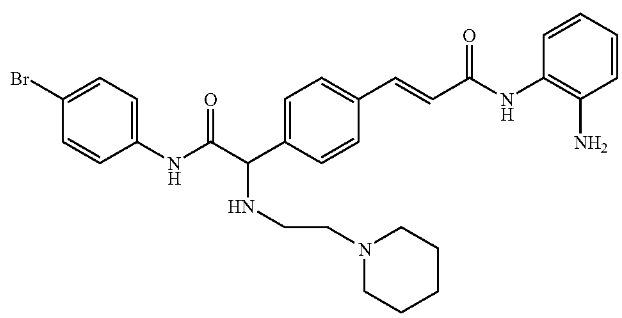 | 576.54 | 576 | 576 |
| 4-32 | 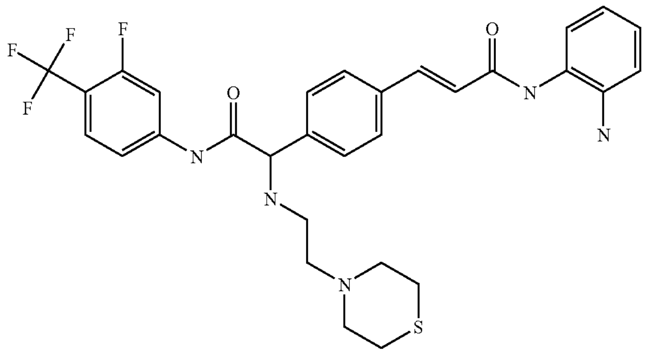 | 601.67 | 602 | 602 |

TABLE 1-continued

| Cmpd # | Structure | MW | MS (MH+) calc'd | MS (MH+) exp |
|---|---|---|---|---|
| 4-33 | 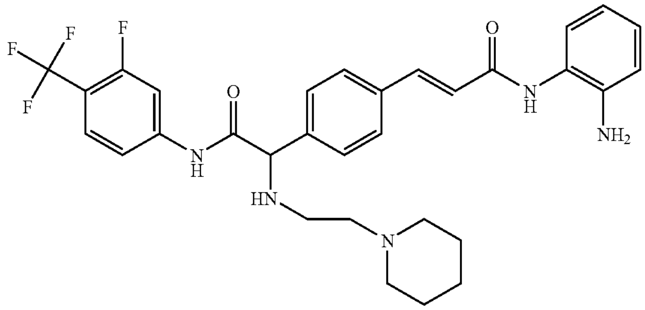 | 583.63 | 584 | 584 |
| 4-34 | 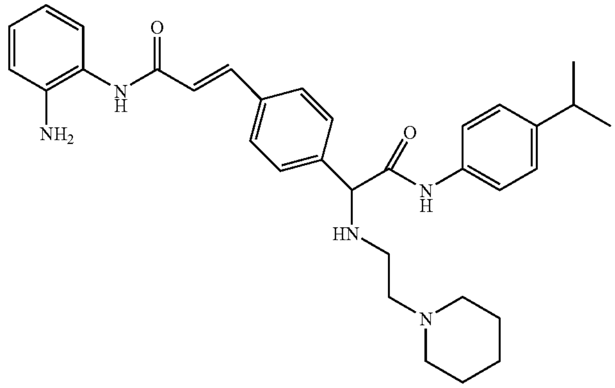 | 539.73 | 540 | 540 |
| 4-35 | 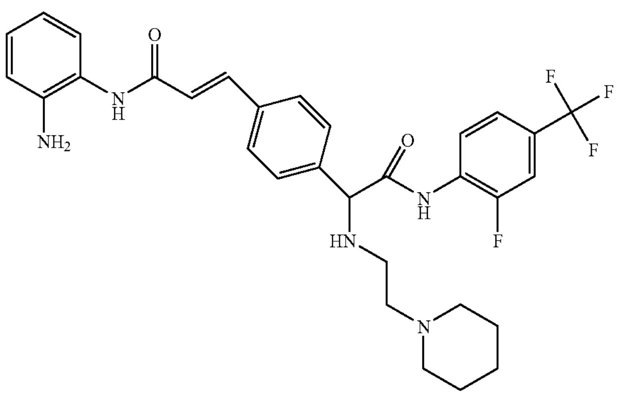 | 583.63 | 584 | 584 |
| 4-36 | 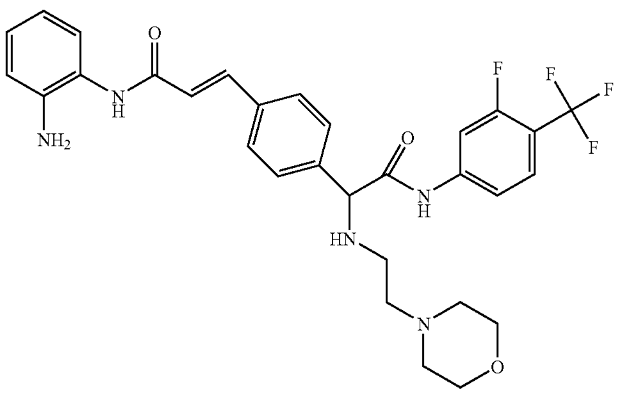 | 585.61 | 586 | 586 |

TABLE 1-continued

| Cmpd # | Structure | MW | MS (MH+) calc'd | MS (MH+) exp |
|---|---|---|---|---|
| 4-37 | 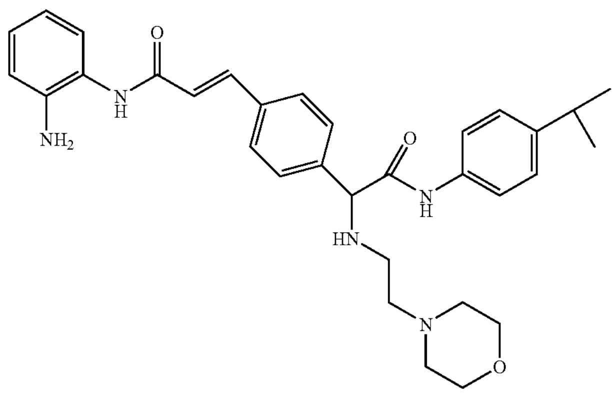 | 541.70 | 542 | 542 |
| 4-38 | 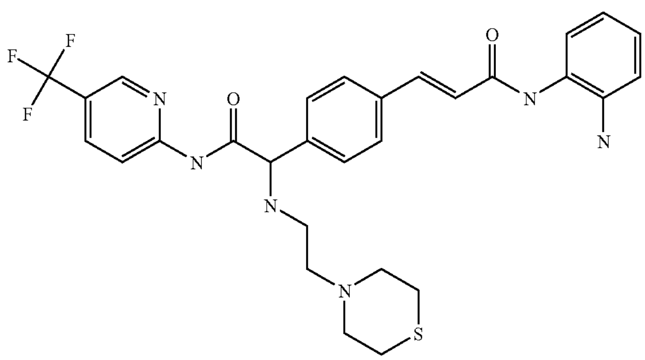 | 584.67 | 585 | 585 |
| 4-39 | 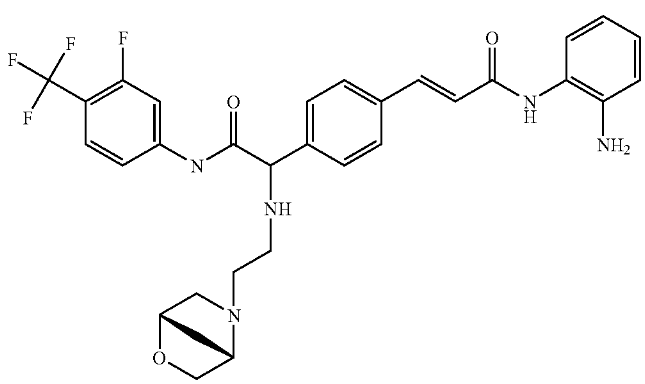 | 597.62 | 598 | 598 |
| 4-40 | 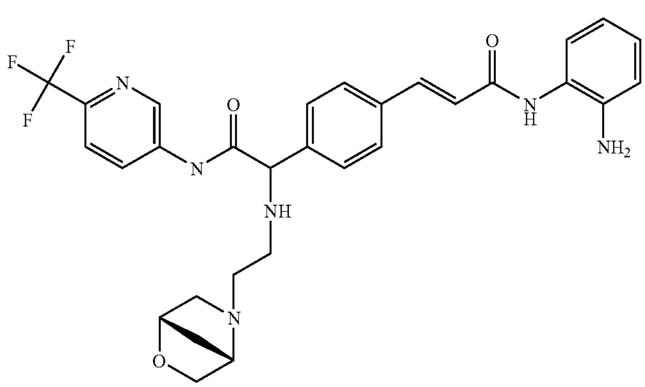 | 580.62 | 581 | 581 |

TABLE 1-continued

| Cmpd # | Structure | MW | MS (MH+) calc'd | MS (MH+) exp |
|---|---|---|---|---|
| 4-41 | 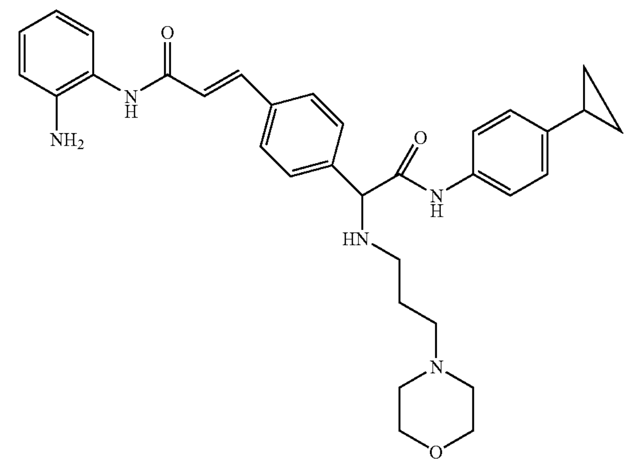 | 553.71 | 554 | 554 |
| 4-42 | 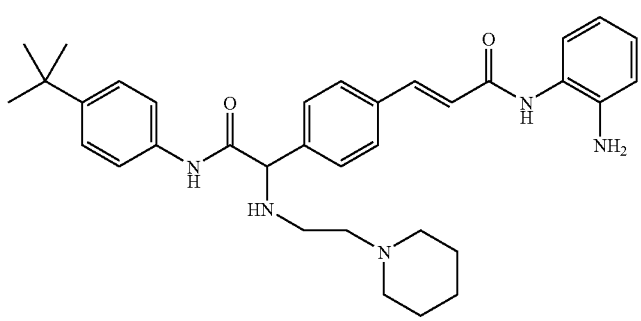 | 553.75 | 554 | 554 |
| 4-43 | 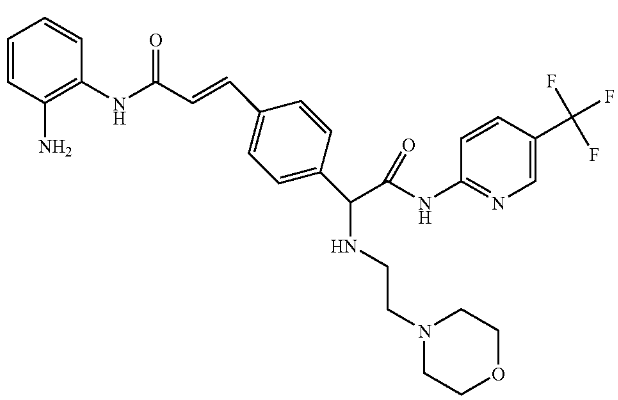 | 568.60 | 569 | 569 |

TABLE 1-continued

| Cmpd # | Structure | MW | MS (MH+) calc'd | MS (MH+) exp |
|---|---|---|---|---|
| 4-44 | 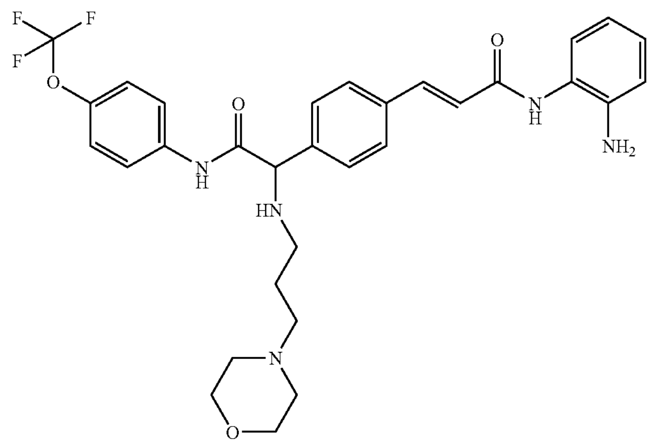 | 597.64 | 598 | 598 |
| 4-45 | 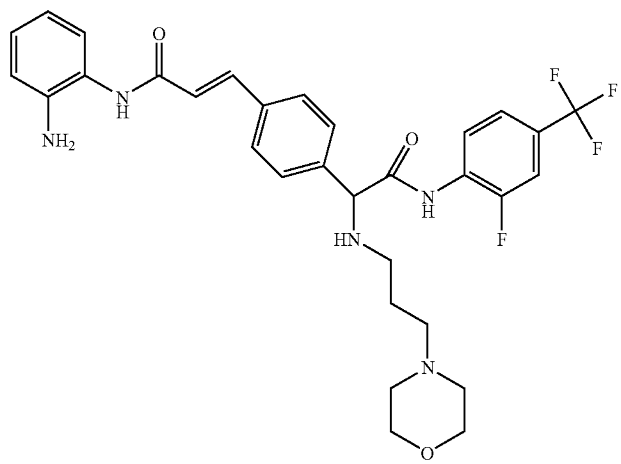 | 599.63 | 600 | 600 |
| 4-46 | 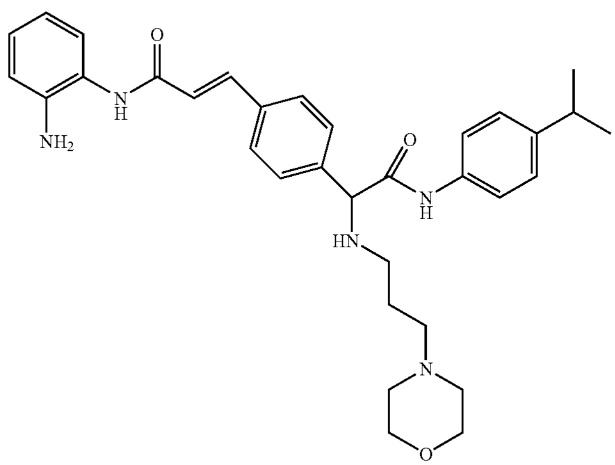 | 555.73 | 556 | 556 |

TABLE 1-continued

| Cmpd # | Structure | MW | MS (MH+) calc'd | MS (MH+) exp |
|---|---|---|---|---|
| 4-47 | 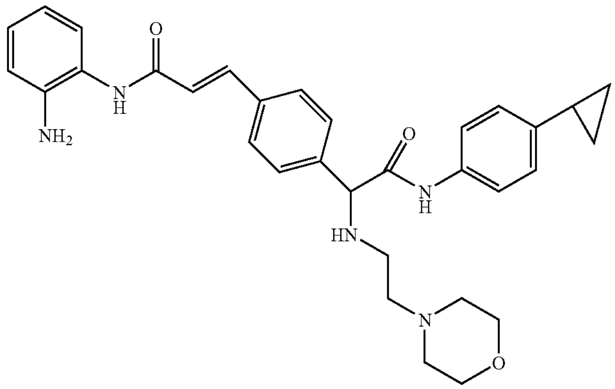 | 539.68 | 540 | 540 |
| 4-48 | 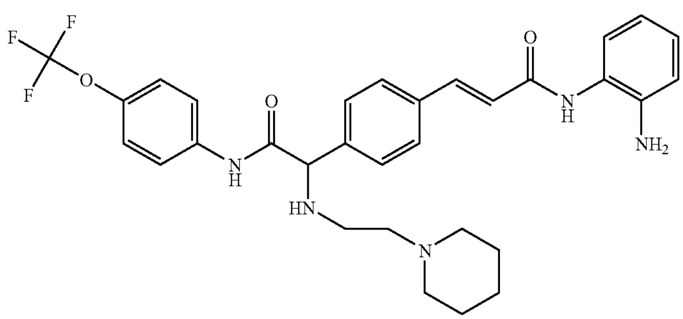 | 581.64 | 582 | 582 |
| 4-49 | 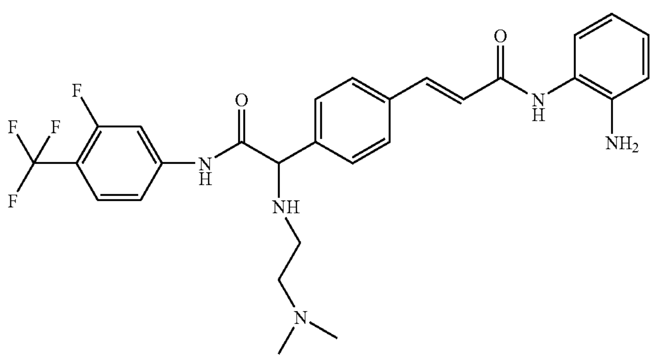 | 543.37 | 544 | 544 |
| 4-50 | 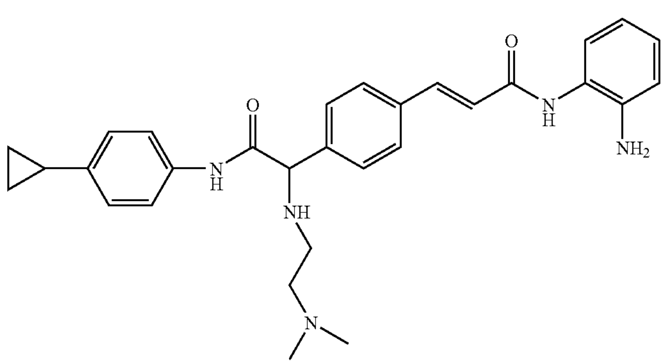 | 497.65 | 498 | 498 |

TABLE 1-continued

| Cmpd # | Structure | MW | MS (MH+) calc'd | MS (MH+) exp |
|---|---|---|---|---|
| 4-51 | 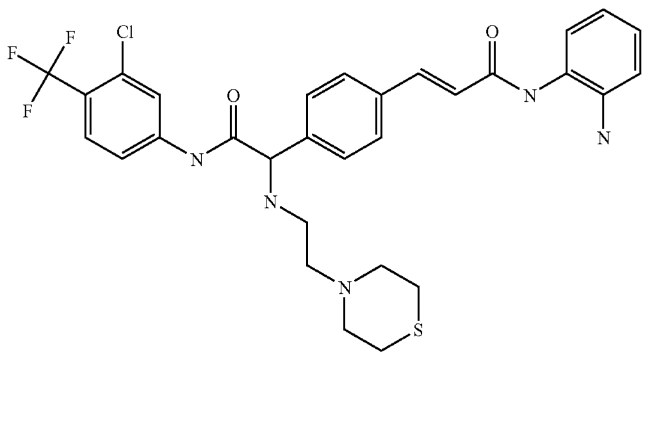 | 618.13 | 618 | 618 |
| 4-52 | 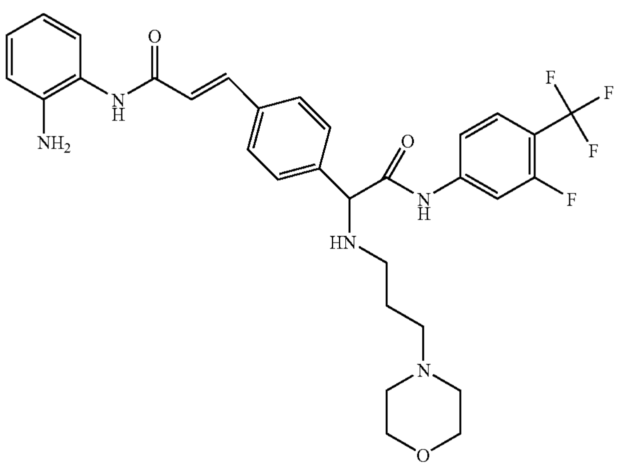 | 599.63 | 600 | 600 |
| 4-53 | 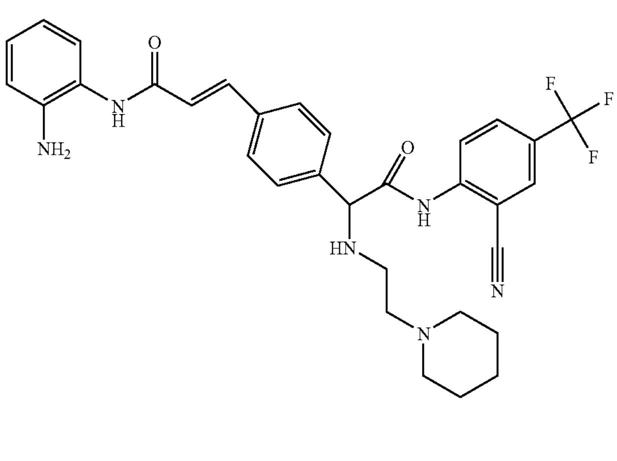 | 590.65 | 591 | 591 |

TABLE 1-continued

| Cmpd # | Structure | MW | MS (MH+) calc'd | MS (MH+) exp |
|---|---|---|---|---|
| 4-54 | 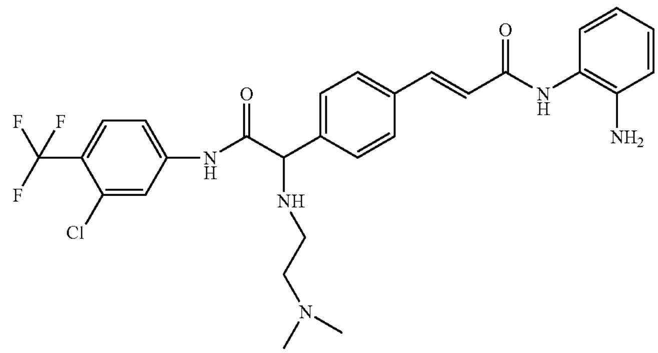 | 560.02 | 560 | 560 |
| 4-55 | 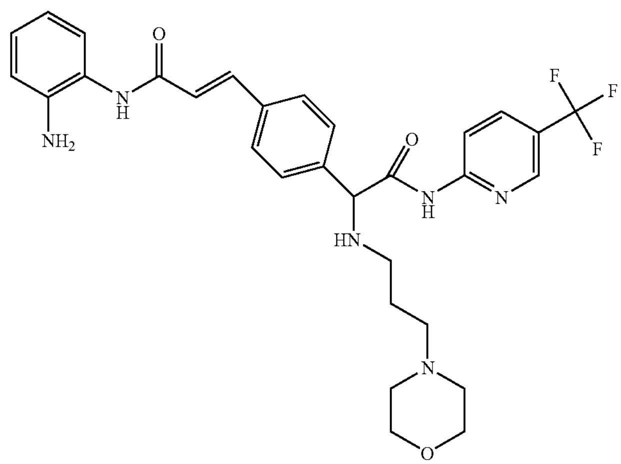 | 582.63 | 583 | 583 |
| 4-56 | 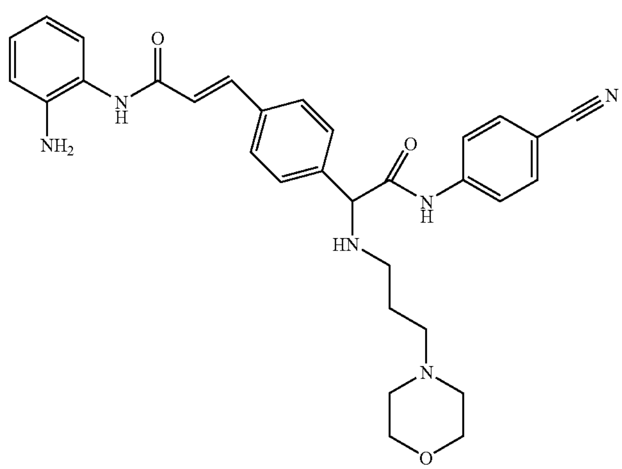 | 538.66 | 539 | 539 |

TABLE 1-continued

| Cmpd # | Structure | MW | MS (MH+) calc'd | MS (MH+) exp |
|---|---|---|---|---|
| 4-57 | 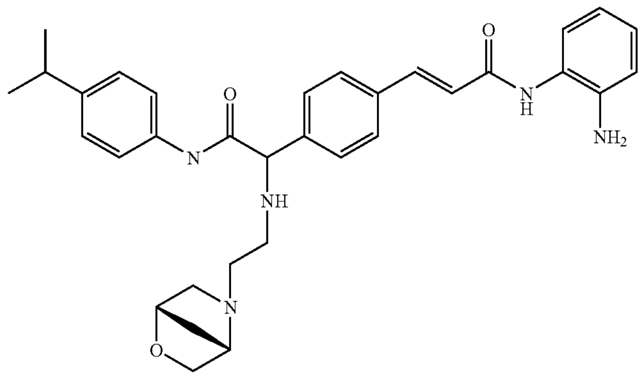 | 553.71 | 554 | 554 |
| 4-58 | 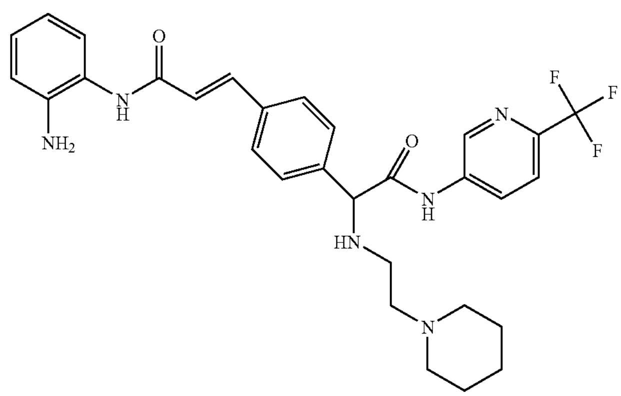 | 566.63 | 567 | 567 |
| 4-59 | 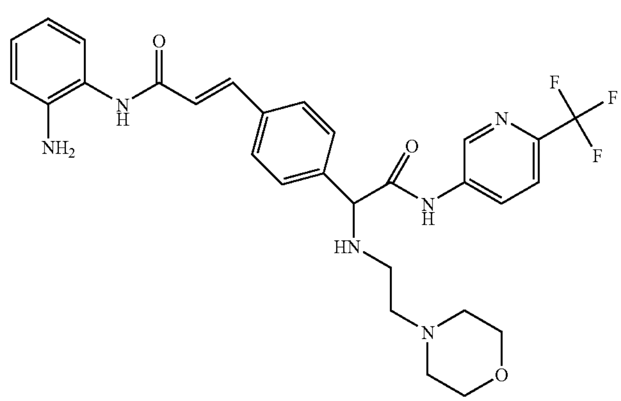 | 568.60 | 569 | 569 |

TABLE 1-continued

| Cmpd # | Structure | MW | MS (MH+) calc'd | MS (MH+) exp |
| --- | --- | --- | --- | --- |
| 4-60 | 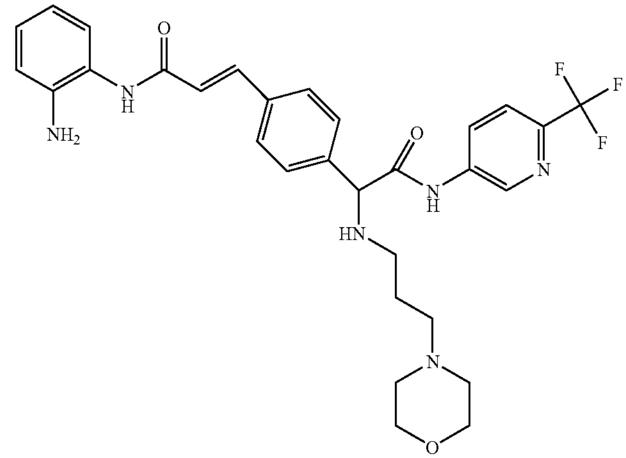 | 582.63 | 583 | 583 |
| 4-61 | 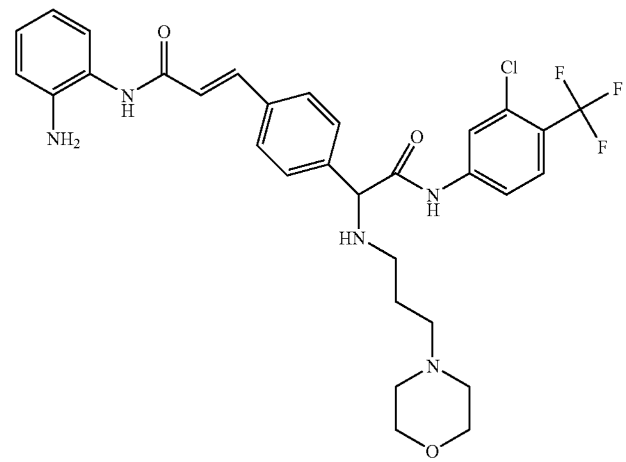 | 616.09 | 616 | 616 |
| 4-62 | 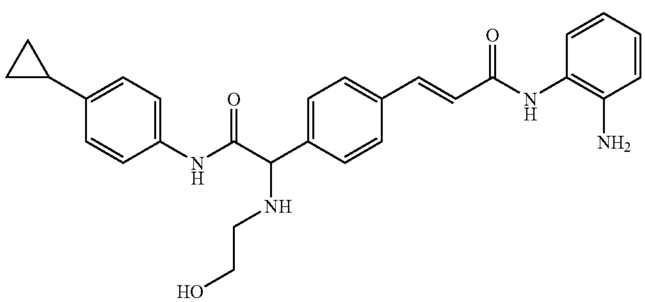 | 470.58 | 471 | 471 |
| 4-63 | 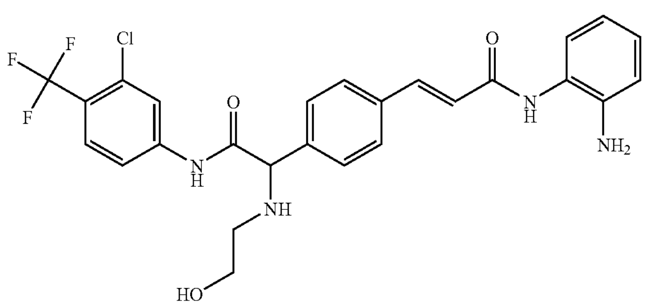 | 532.95 | 533 | 533 |

TABLE 1-continued

| Cmpd # | Structure | MW | MS (MH+) calc'd | MS (MH+) exp |
|---|---|---|---|---|
| 4-64 | 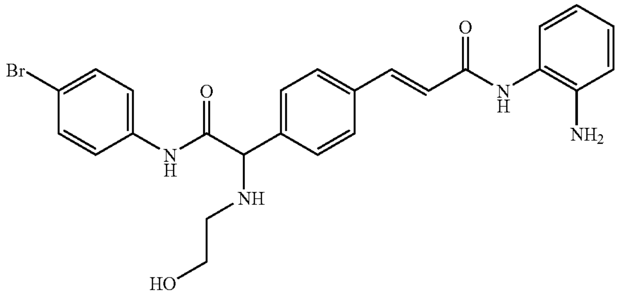 | 509.41 | 509 | 509 |
| 4-65 | 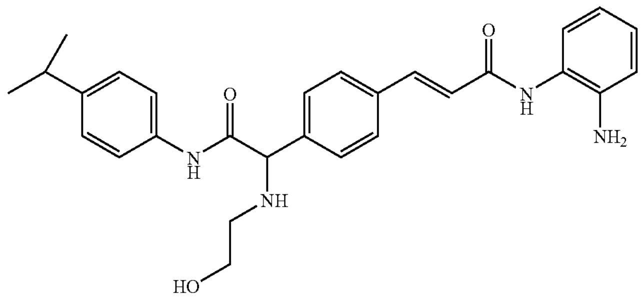 | 472.59 | 473 | 473 |
| 4-66 | 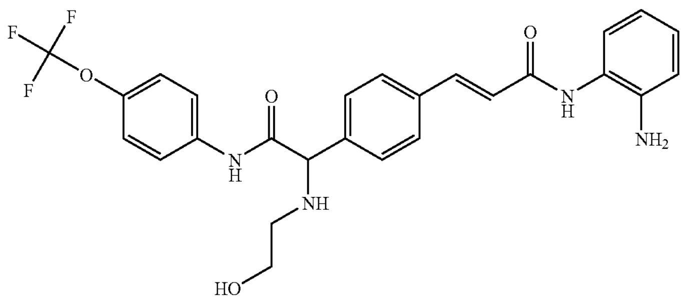 | 514.51 | 515 | 515 |
| 4-67 | 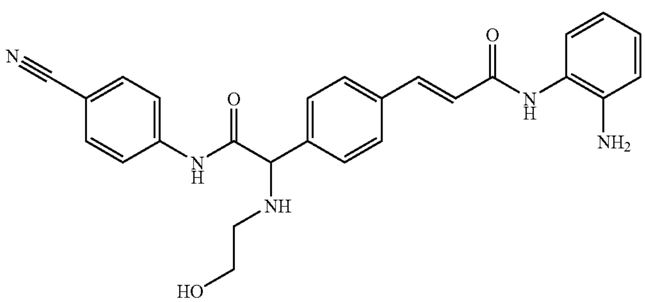 | 455.52 | 456 | 456 |
| 4-68 | 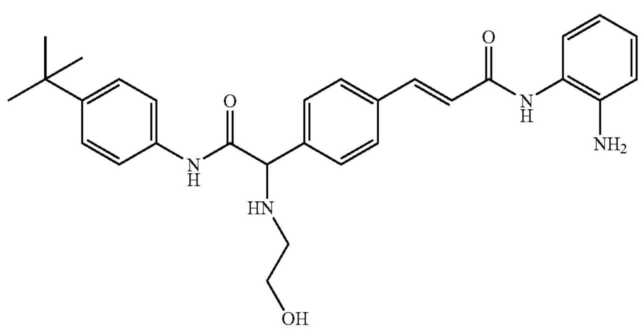 | 486.62 | 487 | 487 |

TABLE 1-continued

| Cmpd # | Structure | MW | MS (MH+) calc'd | MS (MH+) exp |
|---|---|---|---|---|
| 4-69 | 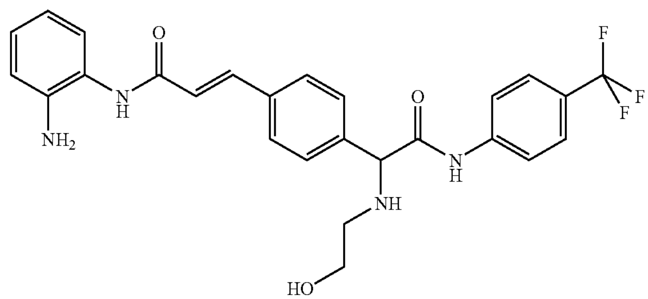 | 498.51 | 499 | 499 |
| 4-70 | 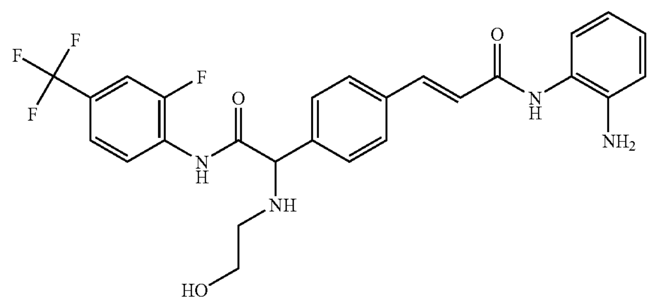 | 516.50 | 517 | 517 |
| 4-71 | 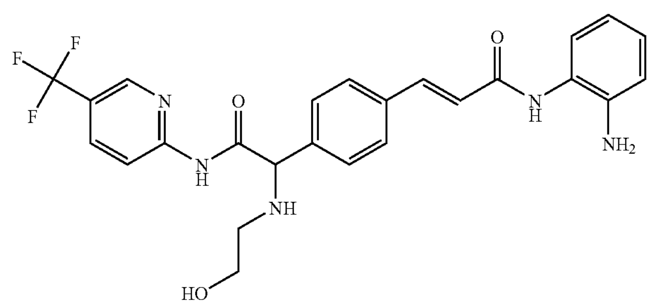 | 499.50 | 500 | 500 |
| 4-72 | 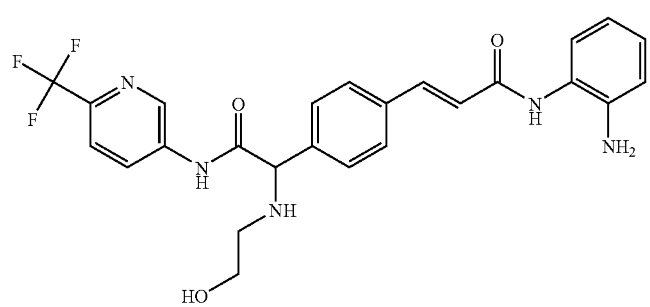 | 499.50 | 500 | 500 |

TABLE 1-continued

| Cmpd # | Structure | MW | MS (MH+) calc'd | MS (MH+) exp |
|---|---|---|---|---|
| 4-73 | 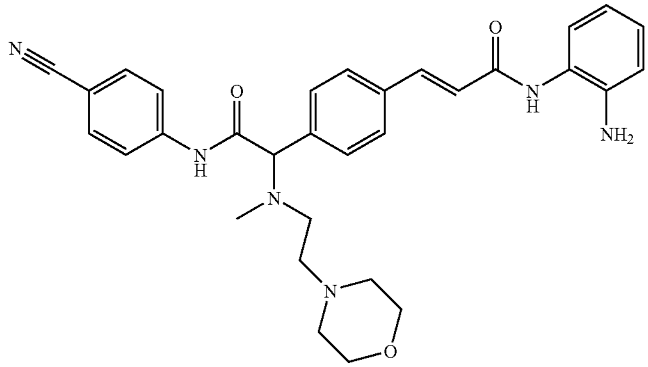 | 538.66 | 539 | 539 |
| 4-74 | 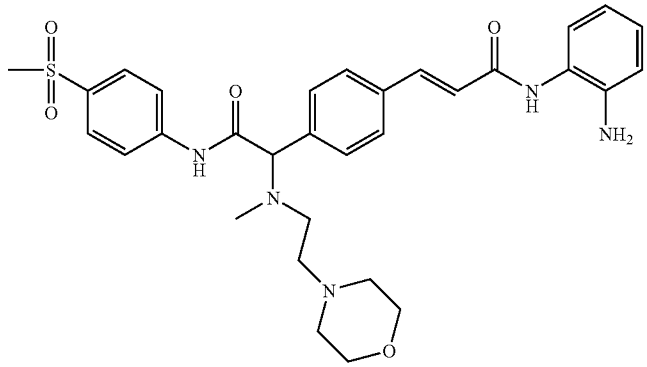 | 591.74 | 592 | 592 |
| 4-75 | 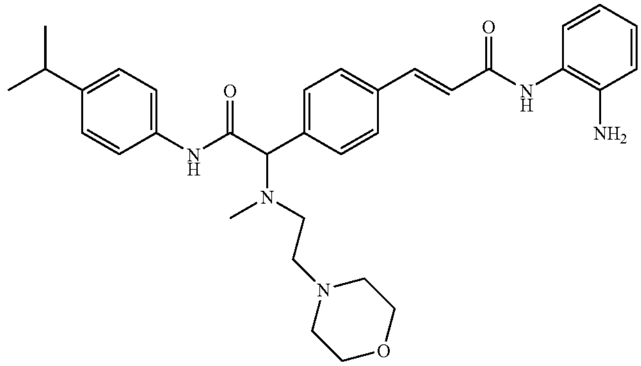 | 555.73 | 556 | 556 |
| 4-76 | 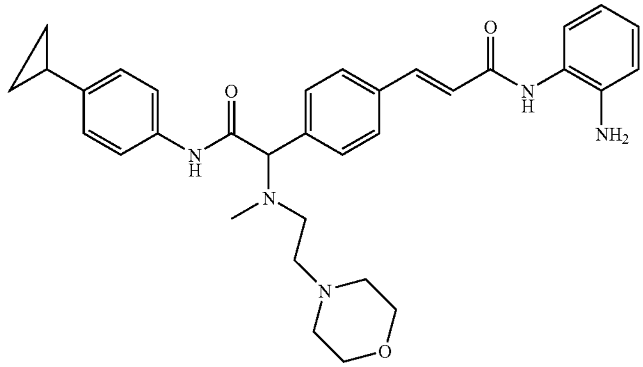 | 553.71 | 554 | 554 |

TABLE 1-continued

| Cmpd # | Structure | MW | MS (MH+) calc'd | MS (MH+) exp |
|---|---|---|---|---|
| 4-77 | 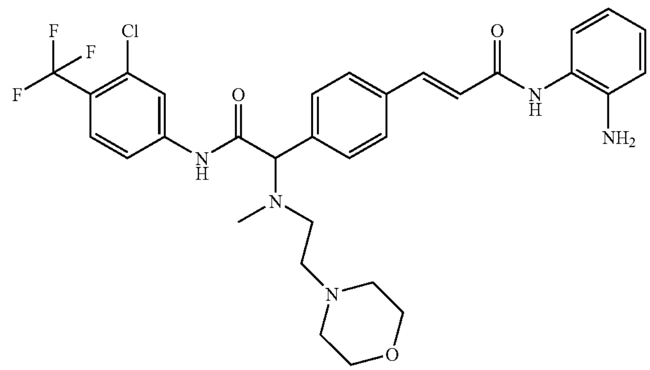 | 616.09 | 616 | 616 |
| 4-78 | 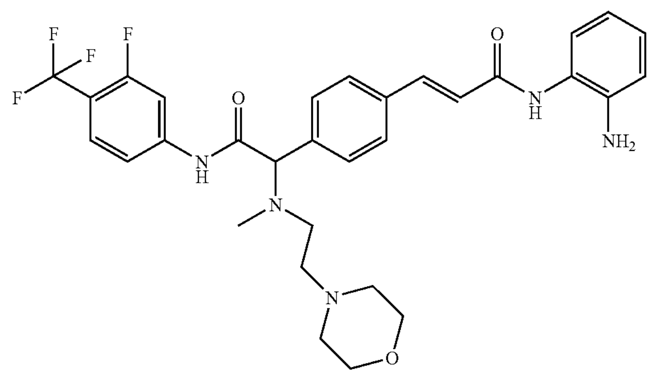 | 599.63 | 600 | 600 |
| 4-79 | 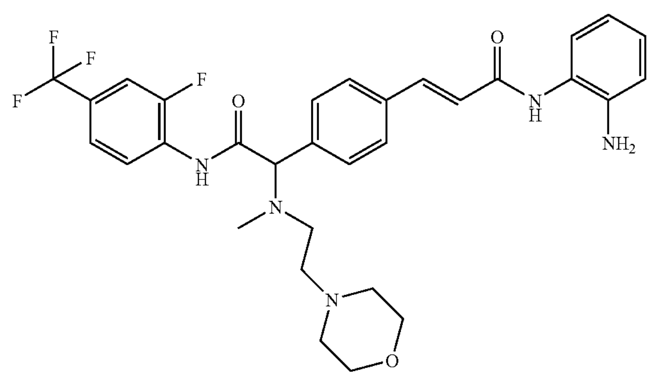 | 599.63 | 600 | 600 |
| 4-80 | 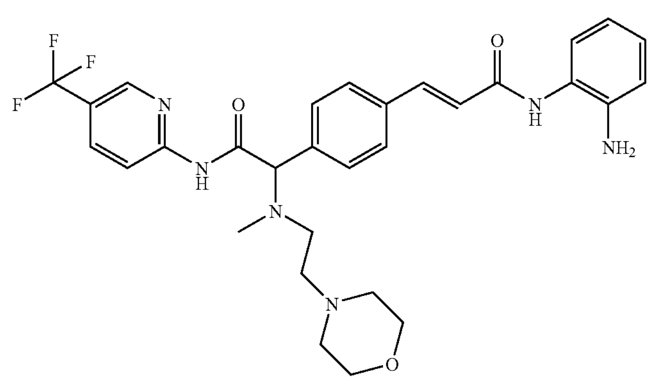 | 582.63 | 583 | 583 |

Example 5

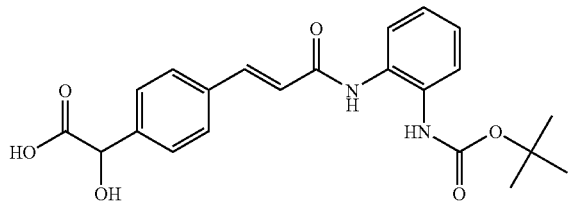

(E)-{4-[2-(2-tert-Butoxycarbonylamino-phenylcarbamoyl)-vinyl]-phenyl}-hydroxy-acetic acid To a solution of (E)-{4-[2-(2-tert-butoxycarbonylamino-phenylcarbamoyl)-vinyl]-phenyl}-hydroxy-acetic acid methyl ester (10.0 g, 23.5 mmol) in THF (100 mL) was added aqueous lithium hydroxide (1 M, 47 mL). After stirring at room temperature for 1 h, the pH was adjusted to 3 by addition of 0.5 N HCl. The resulting mixture was extracted with ethyl acetate (100 mL×2). The combined organics were washed with brine, dried over $Na_2SO_4$, and concentrated to afford the crude product as a pale-green solid (9.8 g, quantitative yield) which was used without further purification.

Example 6

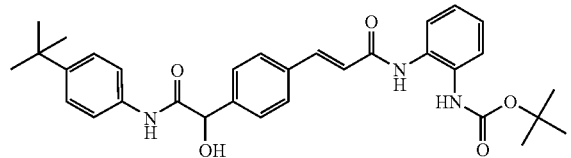

(E)-[2-(3-{4-[(4-tert-Butyl-phenylcarbamoyl)-hydroxy-methyl]-phenyl}-acryloylamino)-phenyl]-carbamic acid tert-butyl ester To a solution of (E)-N-(2-amino-phenyl)-3-{4-[1-(2-morpholin-4-yl-ethylamino)-2-(4-trifluoromethyl-phenoxy)-ethyl]-phenyl}-acrylamide (6.50 g, 15.8 mmol), HOBt (2.34 g, 17.3 mmol), and EDCI (3.32 g, 17.3 mmol) in dichloromethane (160 mL) under $N_2$ was added 4-tert-butylaniline (2.47 g, 16.6 mmol) followed by triethylamine (2.63 mL, 18.9 mmol). After stirring at room temperature overnight, the reaction mixture was washed with water (200 mL), then dried over $Na_2SO_4$, filtered, and concentrated in vacuo. The residue was purified by column chromatography (ethyl acetate/petroleum ether 1:4, 1:2, v:v) to afford the product as a yellow solid (3.2 g, 37%). MS: calc'd 544 (MH+), exp 544 (MH+). $^1$H NMR (d6-DMSO, 400 MHz) δ 9.88 (s, 1H), 9.71 (s, 1H), 8.48 (s, 1H), 7.62 (d, 2H, J=8.2 Hz), 7.61 (m, 4H), 7.59 (d, 1H, J=15.6 Hz), 7.58 (m, 1H), 7.31 (d, 2H, J=8.2 Hz), 7.13 (m, 2H), 6.91 (d, 1H, J=15.6 Hz), 6.49 (d, 1H, J=4.8 Hz), 5.14 (d, 1H, J=4.4 Hz), 1.46 (s, 9H), 1.25 (s, 9H).

Example 7

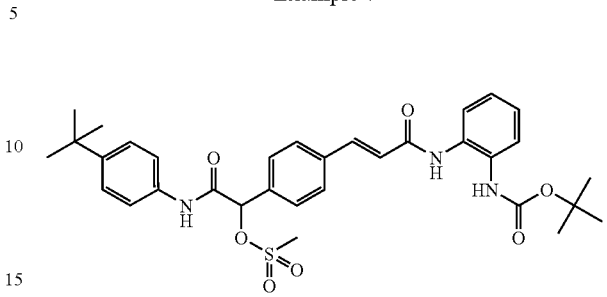

(E)-Methanesulfonic acid {4-[2-(2-tert-butoxycarbonylamino-phenylcarbamoyl)-vinyl]-phenyl}-(4-tert-butyl-phenylcarbamoyl)-methyl ester To a solution of (E)-[2-(3-{4-[(4-tert-butyl-phenylcarbamoyl)-hydroxy-methyl]-phenyl}-acryloylamino)-phenyl]-carbamic acid tert-butyl ester (5.20 g, 9.60 mmol) in dichloromethane (70 mL) was added triethylamine (2.0 mL, 14 mmol). After cooling the reaction to 0 degrees Celcius, methanesulfonyl chloride was added dropwise, and the reaction was further stirred at 0 degrees Celcius for 3 h. After solvent removal, the residue was diluted with ethyl acetate, washed with water, dried over $Na_2SO_4$, filtered, and concentrated to afford the product as a yellow solid (5.2 g, 93%) which was used without further purification. MS: calc'd 622 (MH+), exp 622 (MH+).

Example 8

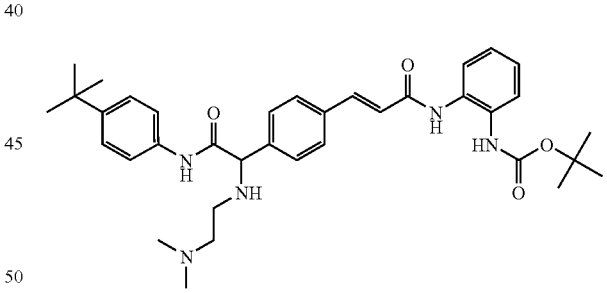

(E)-[2-(3-{4-[(4-tert-Butyl-phenylcarbamoyl)-(2-dimethylamino-ethylamino)-methyl]-phenyl}-acryloylamino)-phenyl]-carbamic acid tert-butyl ester (E)-Methanesulfonic acid {4-[2-(2-tert-butoxycarbonylamino-phenylcarbamoyl)-vinyl]-phenyl}-(4-tert-butyl-phenylcarbamoyl)-methyl ester (196 mg, 0.316 mmol), triethylamine (0.500 mL, 3.60 mmol), and N,N-dimethylethylenediamine (0.093 mL, 0.84 mmol) were dissolved in dichloromethane (2 mL) and heated to 60 degrees Celcius in a sealed tube for two hours. After cooling to room temperature, the reaction was diluted with dichloromethane and washed with water, brine, dried over $Na_2SO_4$, filtered, and concentrated to afford the crude product which was used without further purification.

Example 9

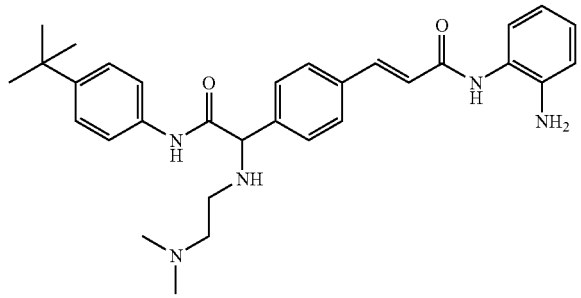

(E)-N-(2-Amino-phenyl)-3-{4-[(4-tert-butyl-phenyl-carbamoyl)-(2-dimethylamino-ethylamino)-methyl]-phenyl}-acrylamide (E)-[2-(3-{4-[(4-tert-Butyl-phenylcarbamoyl)-(2-dimethylamino-ethylamino)-methyl]-phenyl}-acryloylamino)-phenyl]-carbamic acid tert-butyl ester (crude material from Example 8) was treated with 1.25M HCl in methanol (2 mL) at room temperature for 2 hours. The reaction was quenched slowly with solid sodium bicarbonate until the pH was 6-7. The mixture was diluted in acetonitrile with a small amount of dimethylsulfoxide, passed through a 40 μm pipette filter, and then purified by preparative HPLC to obtain 16 mg desired product (24% over two steps). MS: calc'd 514 (MH+) exp 514 (MH+). $^1$H NMR (CD$_3$OD, 400 MHz) δ 7.79 (d, 1H, J=15.6 Hz), 7.74 (d, 2H, J=8.2 Hz), 7.68 (d, 2H, J=8.2 Hz), 7.49 (d, 2H, J=8.4 Hz), 7.37 (d, 2H, J=8.2 Hz), 7.36 (m, 4H), 6.93 (d, 1H, J=15.6 Hz), 3.40 (t, 2H, J=6.2 Hz), 3.23 (t, 2H, J=6.2 Hz), 2.95 (s, 6H), 1.31 (s, 9H).

The compounds described in the following table 2 were prepared by methods analogous to the synthetic methods described above, but using the appropriate starting materials.

TABLE 2

| Cmpd # | Structure | MW | MS (MH+) calc'd | MS (MH+) exp |
|---|---|---|---|---|
| 9-1 | 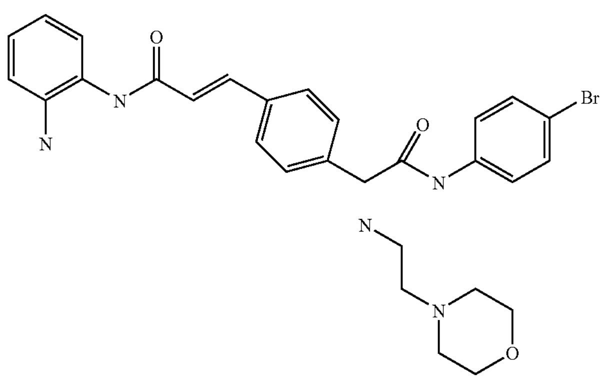 | 578.51 | 578 | 578 |
| 9-2 | 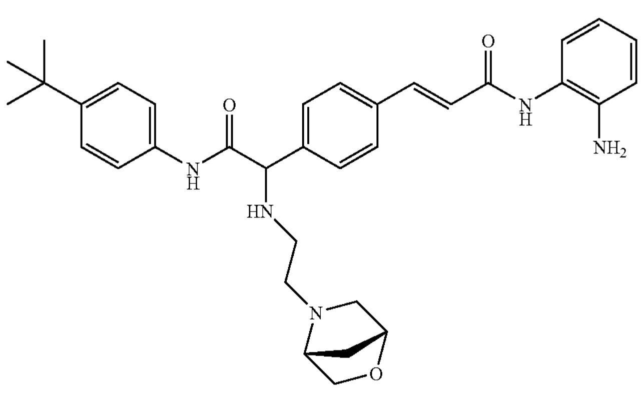 | 567.74 | 568 | 568 |

TABLE 2-continued

| Cmpd # | Structure | MW | MS (MH+) calc'd | MS (MH+) exp |
|---|---|---|---|---|
| 9-3 | 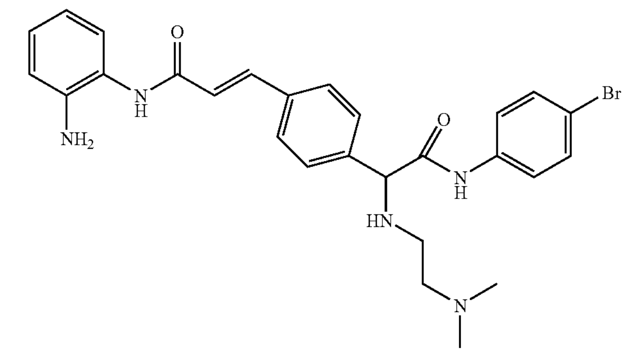 | 536.48 | 536 | 536 |
| 9-4 | 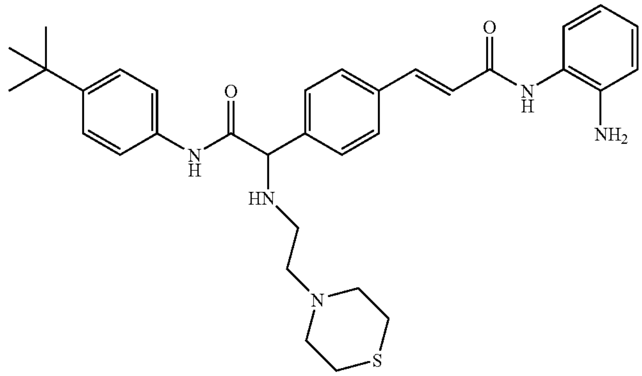 | 571.79 | 572 | 572 |
| 9-5 | 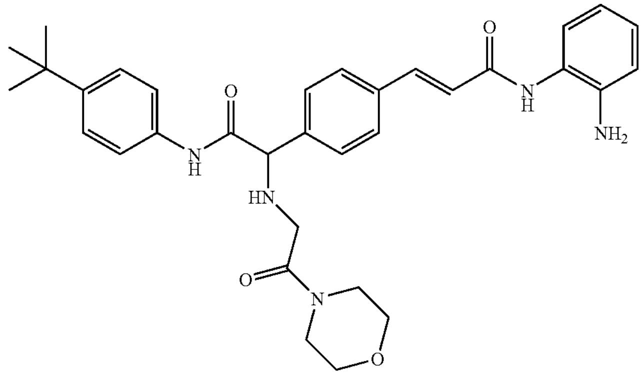 | 569.71 | 570 | 570 |
| 9-6 | 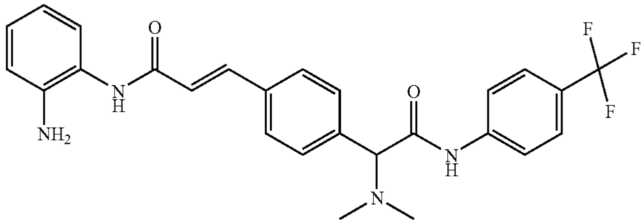 | 482.51 | 483 | 483 |

TABLE 2-continued

| Cmpd # | Structure | MW | MS (MH+) calc'd | MS (MH+) exp |
|---|---|---|---|---|
| 9-7 | 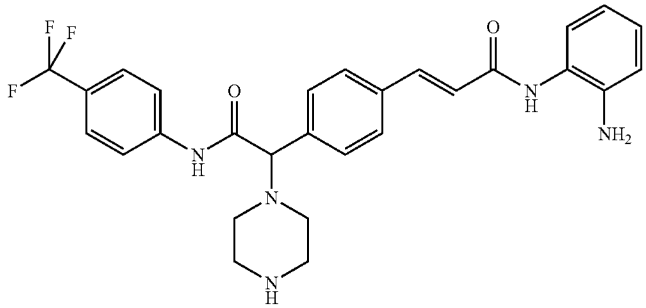 | 523.56 | 524 | 524 |
| 9-8 | 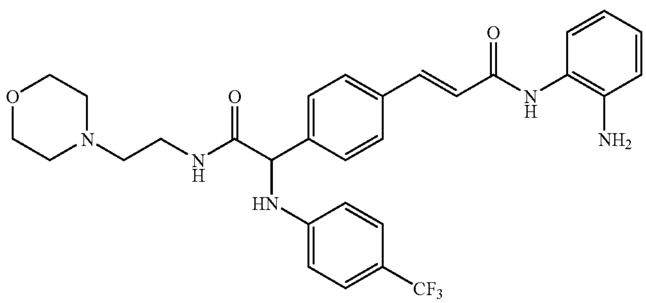 | 567.62 | 568 | 568 |
| 9-9 | 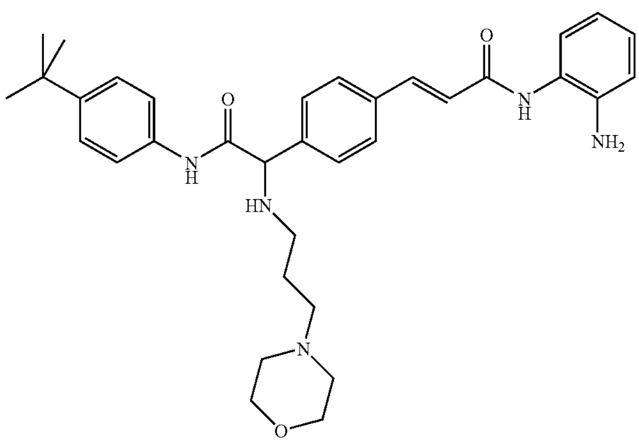 | 569.75 | 570 | 570 |
| 9-10 | 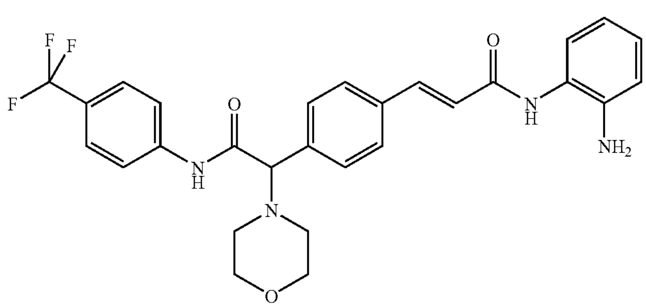 | 524.55 | 525 | 525 |

TABLE 2-continued
| Cmpd # | Structure | MW | MS (MH+) calc'd | MS (MH+) exp |
|---|---|---|---|---|
| 9-11 | 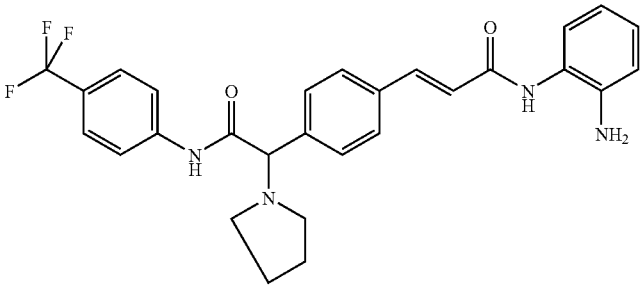 | 508.55 | 509 | 509 |
| 9-12 | 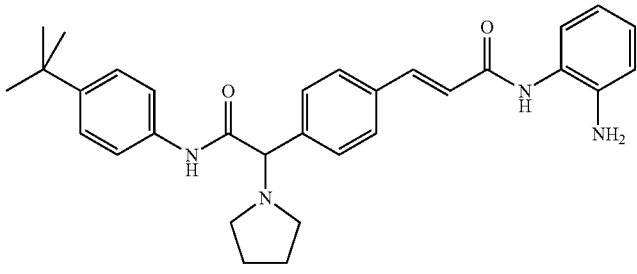 | 496.66 | 497 | 497 |
| 9-13 | 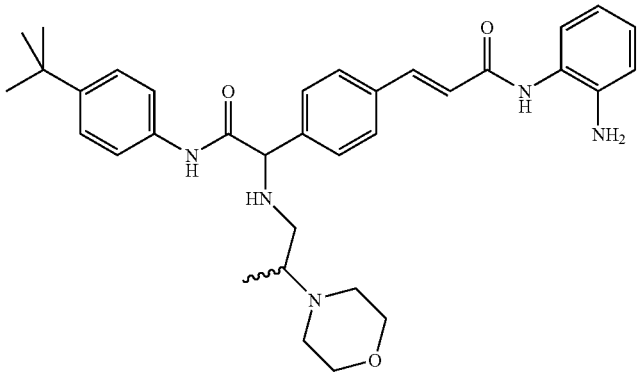 | 569.75 | 570 | 570 |
| 9-14 | 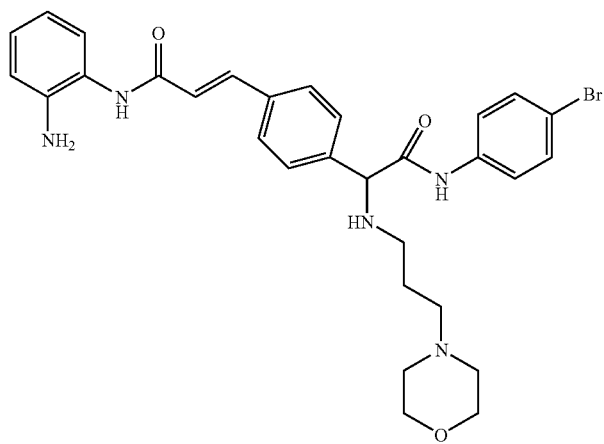 | 592.54 | 592 | 592 |

TABLE 2-continued

| Cmpd # | Structure | MW | MS (MH+) calc'd | MS (MH+) exp |
|---|---|---|---|---|
| 9-15 | 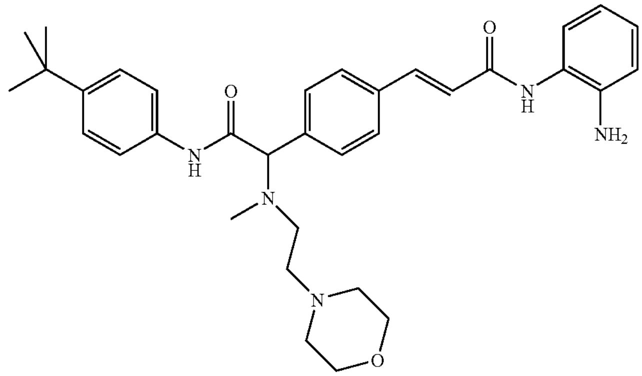 | 569.75 | 570 | 570 |
| 9-16 | 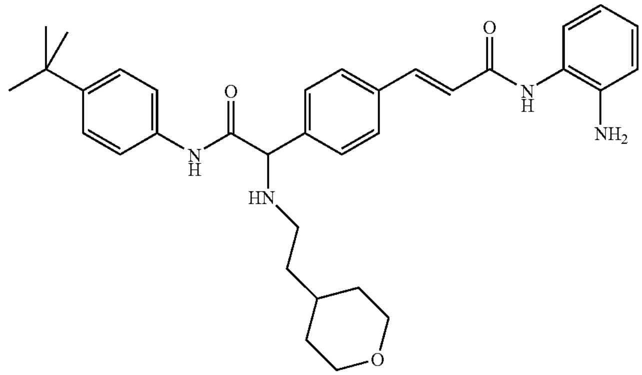 | 554.74 | 555 | 555 |
| 9-17 | 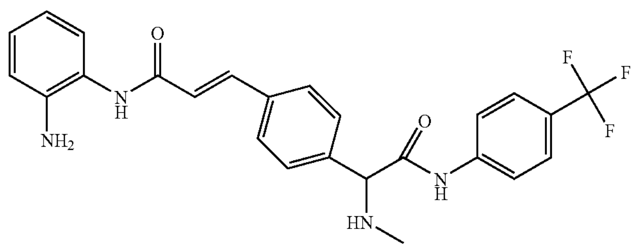 | 468.48 | 469 | 469 |
| 9-18 | 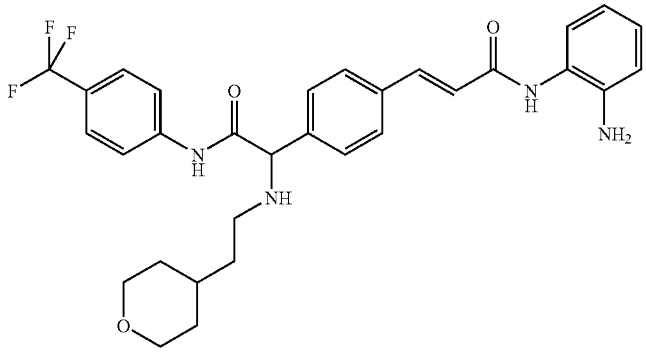 | 566.63 | 567 | 567 |

TABLE 2-continued

| Cmpd # | Structure | MW | MS (MH+) calc'd | MS (MH+) exp |
|---|---|---|---|---|
| 9-19 | 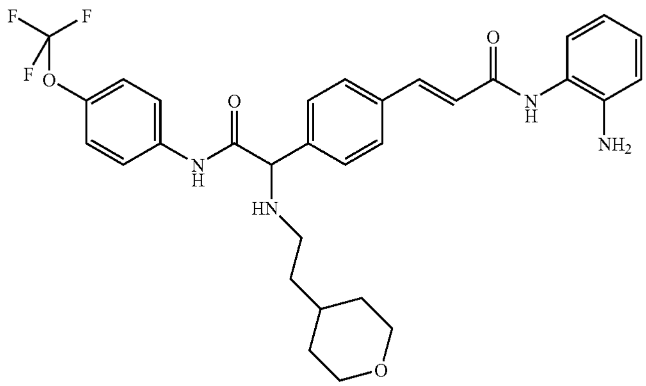 | 582.63 | 583 | 583 |
| 9-20 | 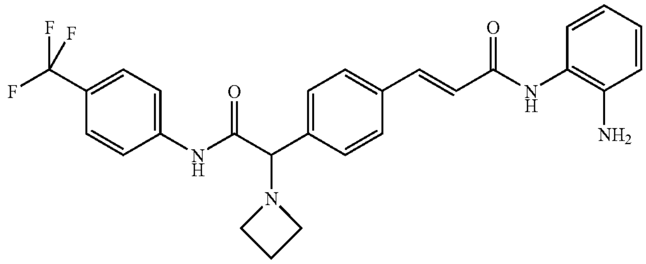 | 494.52 | 495 | 495 |
| 9-21 | 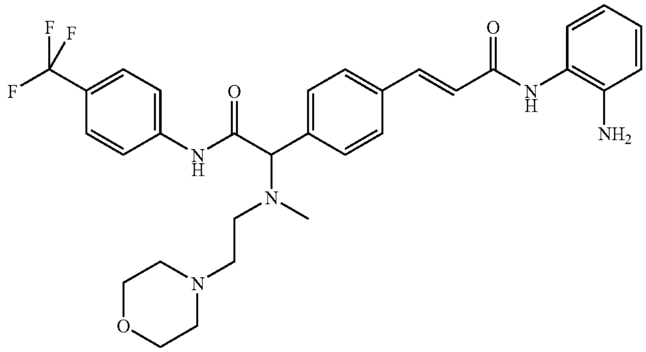 | 581.64 | 582 | 582 |
| 9-22 | 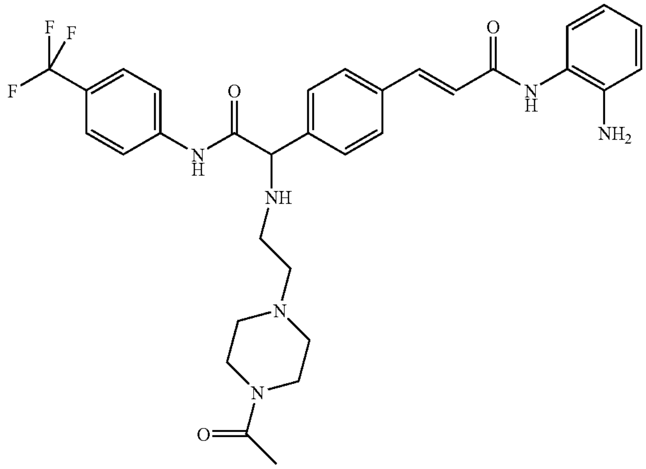 | 608.67 | 609 | 609 |

TABLE 2-continued
| Cmpd # | Structure | MW | MS (MH+) calc'd | MS (MH+) exp |
|---|---|---|---|---|
| 9-23 | 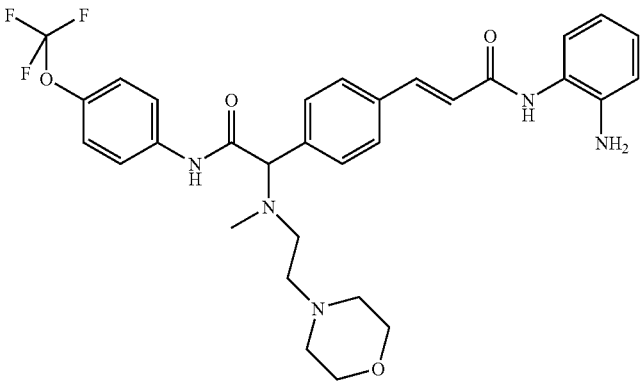 | 597.64 | 598 | 598 |
| 9-24 | 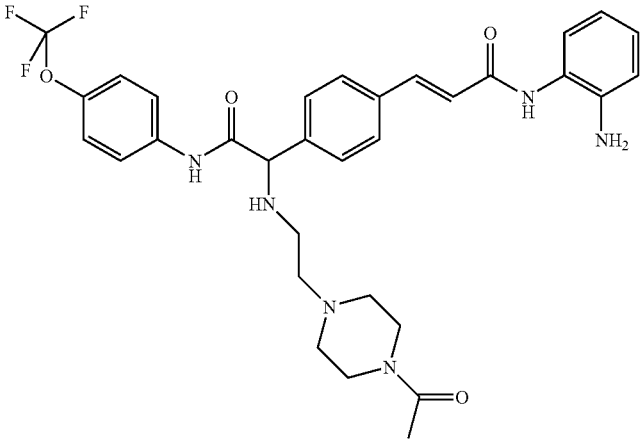 | 624.67 | 625 | 625 |
| 9-25 | 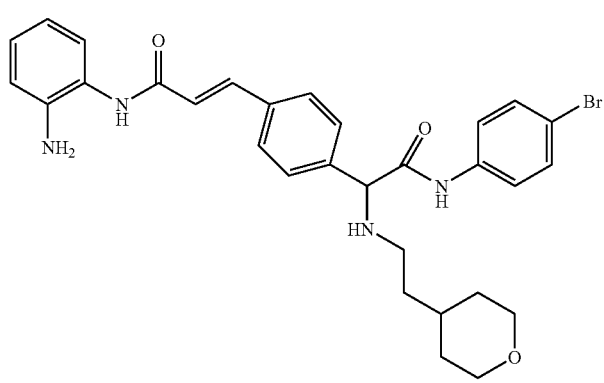 | 577.53 | 577 | 577 |

TABLE 2-continued

| Cmpd # | Structure | MW | MS (MH+) calc'd | MS (MH+) exp |
|---|---|---|---|---|
| 9-26 | 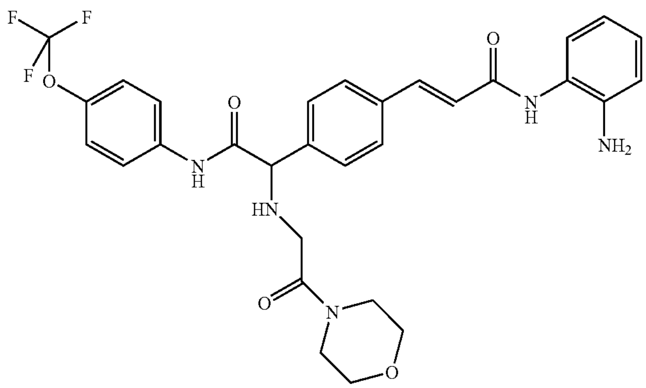 | 597.60 | 598 | 598 |
| 9-27 | 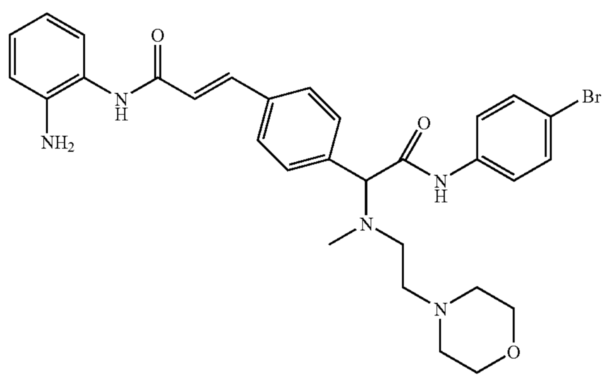 | 592.54 | 592 | 592 |
| 9-28 | 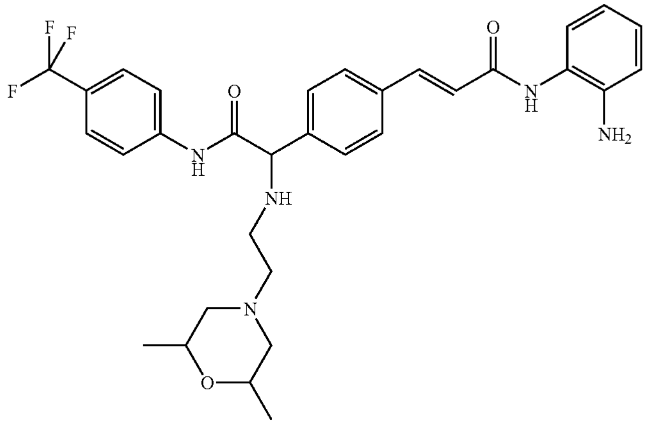 | 595.67 | 596 | 596 |
| 9-29 | 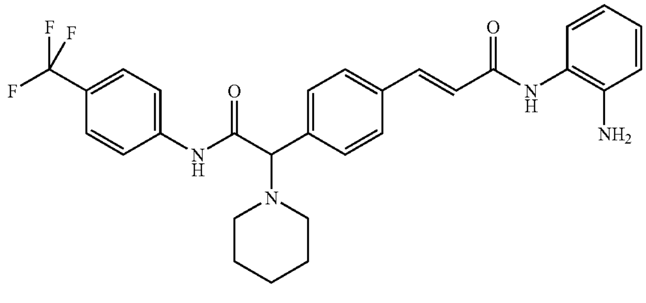 | 522.58 | 523 | 523 |

TABLE 2-continued

| Cmpd # | Structure | MW | MS (MH+) calc'd | MS (MH+) exp |
|---|---|---|---|---|
| 9-30 | 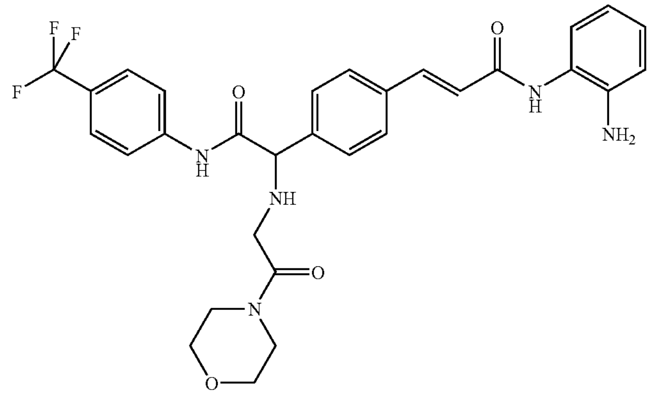 | 581.60 | 582 | 582 |
| 9-31 | 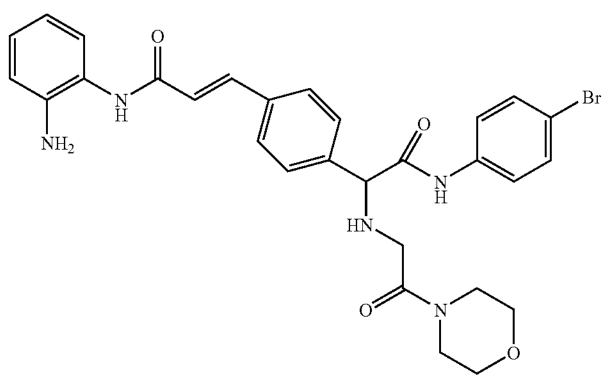 | 592.50 | 592 | 592 |
| 9-32 | 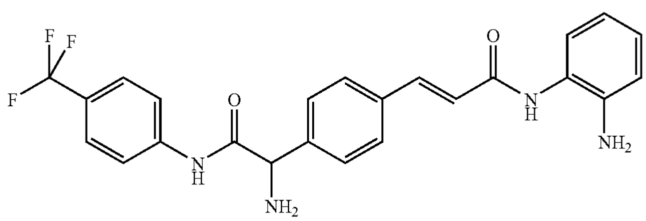 | 454.46 | 455 | 455 |

Example 10

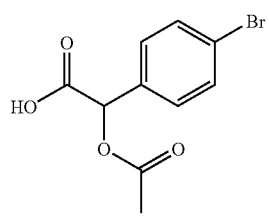

Acetoxy-(4-bromo-phenyl)-acetic acid

To a solution of 4-bromomandelic acid (20.6 g, 89.0 mmol) dissolved in pyridine (50 mL) was added acetic anhydride (10 g, 98 mmol) dropwise while cooling with an ice bath. After stirring overnight at room temperature, the solvent was removed and the resulting residue dissolved in ethyl acetate (150 mL). This was washed twice with 1N HCl, brine, and then concentrated in vacuo to obtain a white solid (18.2 g, 75%) which was used without further purification.

Example 11

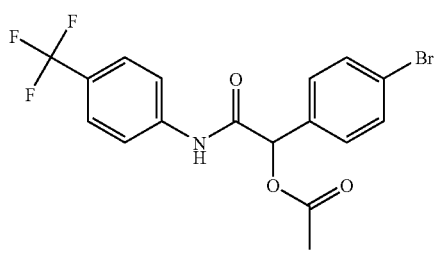

Acetic acid (4-bromo-phenyl)-(4-trifluoromethyl-phenylcarbamoyl)-methyl ester

To a cooled solution (0 degrees Celcius) of acetoxy-(4-bromo-phenyl)-acetic acid (6.1 g, 22 mmol) in dichloromethane (30 mL) was added oxalyl chloride (4.2 g, 33 mmol) dropwise. After stirring for an additional 1 hour at room temperature, the reaction mixture was concentrated in vacuo and dried under vacuum. The acid chloride intermediate was dissolved in dichloromethane (20 mL) and then added over 1 hr to a solution of 4-trifluoromethylaniline (4.0 g, 25 mmol) and triethylamine (3.6 mL, 25 mmol) in dichloromethane (10 mL) at 0 degrees Celcius. The reaction was then allowed to warm to room temperature and stirred for 30 minutes. The reaction was diluted with dichloromethane and then washed twice with 1N HCl, twice with saturated sodium bicarbonate, and twice with brine. The organic layer was then dried over magnesium sulfate, filtered, and concentrated in vacuo to furnish a yellow solid. The solid was washed with ether to obtain a white solid (5.7 g, 61%).

Example 12

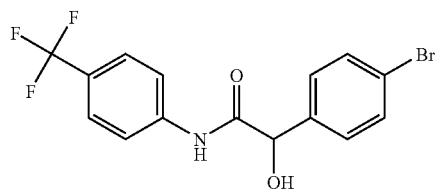

2-(4-Bromo-phenyl)-2-hydroxy-N-(4-trifluoromethyl-phenyl)-acetamide

To a solution of acetic acid (4-bromo-phenyl)-(4-trifluoromethyl-phenylcarbamoyl)-methyl ester (5.7 g, 13.7 mmol) in THF (20 mL) was added LiOH monohydrate (0.863 g, 20.5 mmol) in water (12 mL) dropwise at room temperature. After stirring an additional hour at room temperature, the mixture was extracted with ethyl acetate. The ethyl acetate layer was dried over sodium sulfate, filtered, and concentrated in vacuo to obtain white solid (5.04 g, 98.8%).

Example 13

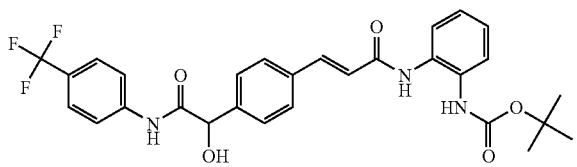

(E)-[2-(3-{4-[Hydroxy-(4-trifluoromethyl-phenylcarbamoyl)-methyl]-phenyl}-acryloylamino)-phenyl]-carbamic acid tert-butyl ester A mixture of 2-(4-Bromo-phenyl)-2-hydroxy-N-(4-trifluoromethyl-phenyl)-acetamide (8.0 g, 21.4 mmol), (2-acryloylamino-phenyl)-carbamic acid tert-butyl ester (6.2 g, 23.6 mmol), tri-o-tolyl-phosphine (1.0 g, 3.3 mmol), triethylamine (12 mL, 86 mmol), and Pd$_2$(dba)$_3$ (1.5 g, 1.6 mmol) in DMF (160 mL) was heated at 90 degrees Celcius overnight under nitrogen atmosphere. The mixture was poured into saturated ammonium chloride solution (300 mL) and extracted with ethyl acetate three times. The organic layer was washed with brine, dried over sodium sulfate, filtered, concentrated, and purified by flash column chromatography (ethyl acetate/petroleum ether 1:2) to obtain a white solid (5.8 g, 49%).

Example 14

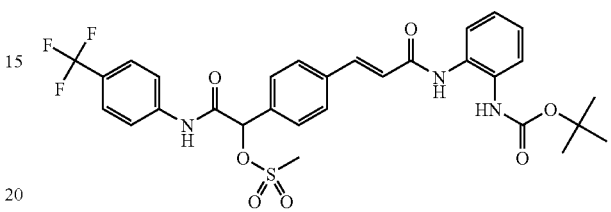

(E)-Methanesulfonic acid {4-[2-(2-tert-butoxycarbonylamino-phenylcarbamoyl)-vinyl]-phenyl}-(4-trifluoromethyl-phenylcarbamoyl)-methyl ester To a cooled solution (0 degrees Celcius) of (E)-[2-(3-{4-[hydroxy-(4-trifluoromethyl-phenylcarbamoyl)-methyl]-phenyl}-acryloylamino)-phenyl]-carbamic acid tert-butyl ester (5.80 g, 10.4 mmol) and triethylamine (2.2 mL, 15.8 mmol) in anhydrous dichloromethane (100 mL) was added dropwise methanesulfonyl chloride (1.6 g, 14 mmol). After stirring for about 1.5 hours at 0 degrees Celcius, the reaction mixture was washed three times with ice water, then brine, dried over sodium sulfate, filtered, and concentrated to obtain a yellow solid (6.3 g, 96%) which was used without further purification. MS: calc'd 634 (MH+), exp 634 (MH+). $^1$H NMR (d$_6$-DMSO, 400 MHz) δ 10.3 (s, 1H), 9.69 (s, 1H), 8.45 (s, 1H), 7.94 (d, 2H, J=8.8 Hz), 7.67 (d, 2H, J=8.8 Hz), 7.65 (d, 2H, J=8.2 Hz), 7.60 (d, 2H, J=8.2 Hz), 7.58 (d, 1H, J=15.6 Hz), 7.57 (m, 1H), 7.14 (m, 2H), 6.91 (d, 1H, J=15.6 Hz), 6.60 (broad s, 1H), 5.21 (s, 1H), 3.34 (s, 3H, overlapped with DMSO solvent residual peak), 1.46 (s, 9H).

Example 15

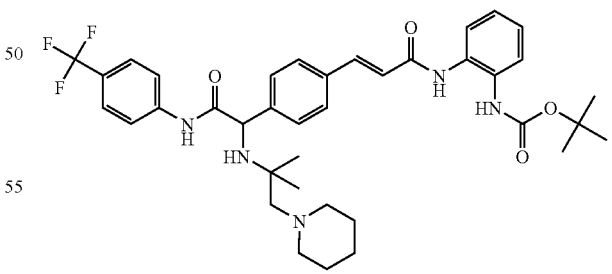

(E)-[2-(3-{4-[(1,1-Dimethyl-2-piperidin-1-yl-ethylamino)-(4-trifluoromethyl-phenylcarbamoyl)-methyl]-phenyl}-acryloylamino)-phenyl]-carbamic acid tert-butyl ester (E)-Methanesulfonic acid {4-[2-(2-tert-butoxycarbonylamino-phenylcarbamoyl)-vinyl]-phenyl}-(4-trifluoromethyl-phenylcarbamoyl)-methyl ester (200 mg, 0.316 mmol), triethylamine (0.500 mL, 3.60 mmol), and 2-methyl-1-piperidino-2-propanamine (131 mg, 0.84 mmol) were dissolved in dichloromethane (2 mL) and heated to 60 degrees Celcius in a sealed tube for two hours. After cooling to room temperature, the reaction was diluted with dichloromethane and washed with water, brine, dried over Na$_2$SO$_4$, filtered, and concentrated to afford the crude product which was used without further purification.

Example 16

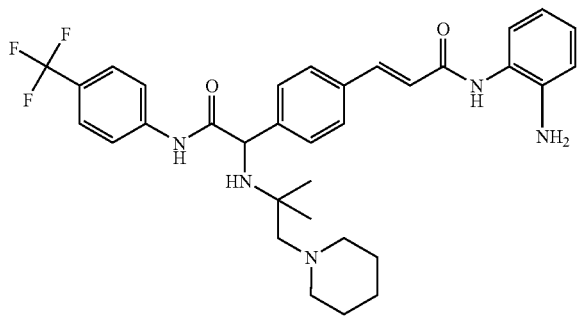

(E)-N-(2-Amino-phenyl)-3-{4-[(1,1-dimethyl-2-piperidin-1-yl-ethylamino)-(4-trifluoromethyl-phenylcarbamoyl)-methyl]-phenyl}-acrylamide (E)-[2-(3-{4-[(1,1-Dimethyl-2-piperidin-1-yl-ethylamino)-(4-trifluoromethyl-phenylcarbamoyl)-methyl]-phenyl}-acryloylamino)-phenyl]-carbamic acid tert-butyl ester (crude material from Example 15) was treated with 1.25M HCl in methanol (2 mL) at room temperature for 2 hours. The reaction was quenched slowly with solid sodium bicarbonate until the pH was 6-7. The mixture was diluted in acetonitrile with a small amount of dimethylsulfoxide, passed through a 40 μm pipette filter, and then purified by preparative HPLC to obtain 8 mg desired product (12% over two steps). MS: calc'd 594 (MH+) exp 594 (MH+). $^1$H NMR (CD$_3$OD, 400 MHz) δ 7.81 (d, 2H, J=10.6 Hz), 7.78 (d, 1H, J=15.6 Hz), 7.71 (d, 2H, J=8.2 Hz), 7.64 (d, 2H, J=10.6 Hz), 7.62 (d, 2H, J=8.2 Hz), 7.32 (m, 4H), 6.90 (d, 1H, J=16 Hz), 4.90 (s, 1H), 3.55 (broad m, 2H), 3.17 (broad m, 2H), 3.16 (d, 1H, J=13.6 Hz), 3.01 (d, 1H, J=13.6 Hz), 2.2-1.8 (m, 6H), 1.33 (s, 3H), 1.32 (s, 3H).

Example 17

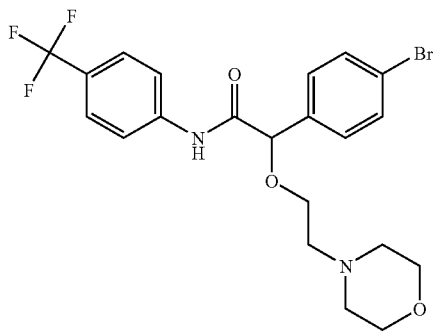

2-(4-Bromo-phenyl)-2-(2-morpholin-4-yl-ethoxy)-N-(4-trifluoromethyl-phenyl)-acetamide A mixture of 2-(4-bromo-phenyl)-2-hydroxy-N-(4-trifluoromethyl-phenyl)-acetamide (374 mg, 1.00 mmol), 4-(2-chloroethyl)morpholine hydrochloride (233 mg, 1.20 mmol), potassium iodide (166 mg, 1.00 mmol) and NaOH (100 mg, 2.50 mmol) in xylene (2 mL) was heated at 130 degrees Celcius for 3 hr. After cooling to room temperature, ethyl acetate (10 mL) and water (10 mL) were added and then the mixture was extracted with ethyl acetate. The organic layer was dried over Na$_2$SO$_4$, filtered, concentrated in vacuo and purified by flash column chromatography (ethyl acetate/petroleum ether 1:5; 1:4; 1:2; v:v) to obtain an oil (300 mg). To the oil was added diluted hydrochloric acid and ether. This mixture was stirred to obtain some solid, then concentrated. Ether was added to the residue, and stirred until the liquid solidified into a yellow solid (436 mg; 83.4%).

Example 18

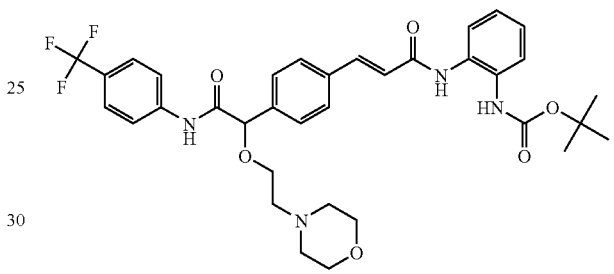

(E)-[2-(3-{4-[(2-Morpholin-4-yl-ethoxy)-(4-trifluoromethyl-phenylcarbamoyl)-methyl]-phenyl}-acryloylamino)-phenyl]-carbamic acid tert-butyl ester A mixture of 2-(4-bromo-phenyl)-2-(2-morpholin-4-yl-ethoxy)-N-(4-trifluoromethyl-phenyl)-acetamide (481 mg, 0.720 mmol), (2-acryloylamino-phenyl)-carbamic acid tert-butyl ester (240 mg, 0.920 mmol), tri-o-tolyl-phosphine (51 mg, 0.17 mmol), triethylamine (421 mg, 4.16 mmol) and Pd$_2$(dba)$_3$ (76 mg, 0.08 mmol) in DMF (4 mL) was heated at 105 degrees Celcius for 1 hr under N$_2$ atmosphere, and then at 95 degrees Celcius overnight. After cooling to room temperature, the mixture was poured into a saturated aqueous solution of NH$_4$Cl and extracted with ethyl acetate four times. The organic layer was washed with brine, dried over Na$_2$SO$_4$, filtered, concentrated in vacuo, and purified by flash column chromatography (dichloromethane/methanol 500:1-100:1) to obtain a brown solid (118 mg, 24.6%). MS: calc'd 669 (MH+), exp 669 (MH+).

Example 19

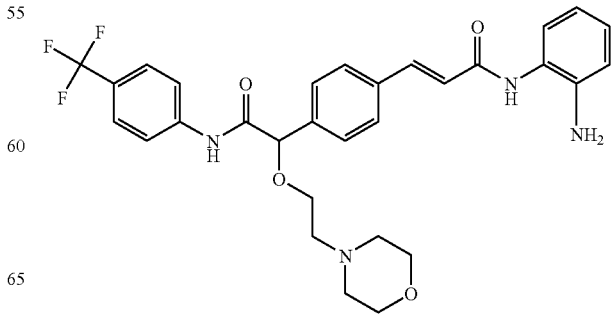

(E)-N-(2-Amino-phenyl)-3-{4-[(2-morpholin-4-yl-ethoxy)-(4-trifluoromethyl-phenylcarbamoyl)-methyl]-phenyl}-acrylamide (E)-[2-(3-{4-[(2-Morpholin-4-yl-ethoxy)-(4-trifluoromethyl-phenylcarbamoyl)-methyl]-phenyl}-acryloylamino)-phenyl]-carbamic acid tert-butyl ester (118 mg, 0.177 mmol) was treated with 1.25M HCl in methanol (1 mL) at room temperature for 2 hours. The reaction was quenched slowly with solid sodium bicarbonate until the pH was 6-7. The mixture was diluted in acetonitrile with a small amount of dimethylsulfoxide, passed through a 40 μm pipette filter, and then purified by preparative HPLC to obtain 17 mg desired product (17%). MS: calc'd 569 (MH+) exp 569 (MH+). $^1$H NMR (d$_6$-DMSO, 400 MHz) δ 10.6 (s, 1H, rotamer a), 10.4 (s, 1H, rotamer b), 9.43 (s, 1H), 7.91 (d, 2H, J=8.0 Hz), 7.70 (d, 2H, J=8.8 Hz), 7.65 (d, 2H, J=8.0 Hz), 7.58 (d, 2H, J=8.8 Hz), 7.55 (d, 1H, J=15.6 Hz), 7.34 (d, 1H, J=6.4 Hz), 6.92 (d, 1H, J=15.6 Hz), 6.91 (t, 1H, J=6.4 Hz), 6.75 (d, 1H, J=7.4 Hz), 6.57 (t, 1H, J=7.4 Hz), 5.11 (s, 1H), 4.96 (s, 2H), 3.70 (broad m, 4H), 3.55 (broad m, 2H), 2.70-2.35 (broad m, 6H).

Example 20

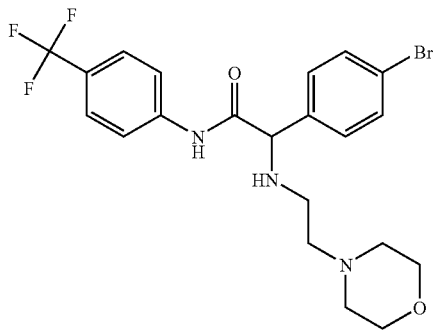

2-(4-Bromo-phenyl)-2-(2-morpholin-4-yl-ethylamino)-N-(4-trifluoromethyl-phenyl)-acetamide To a solution of 4-bromobenzaldehyde (3.09 g, 16.7 mmol) in anhydrous MeOH (10 mL) was added N-aminoethyl-morpholine (2.17 g, 16.7 mmol) followed by trifluoroacetic acid (1.90 g, 16.7 mmol) under N$_2$ atmosphere. After stirring the reaction mixture for 5 minutes, 4-trifluoromethylphenylisocyanide (2.85 g, 16.7 mmol) was added and the reaction then heated to 80 degrees Celcius for 2 h. Anhydrous potassium carbonate (4.60 g, 33.3 mmol) was then added and the reaction stirred at 80 degrees Celcius for an additional 2 h. After solvent removal, the residue was diluted with dichloromethane (100 mL) and water (100 mL). The aqueous layer was extracted with dichloromethane (50 mL x2). The combined organic layers were washed with brine, dried over sodium sulfate, filtered, and concentrated in vacuo. The residue was purified by flash column chromatography eluting with ethyl acetate: petroleum ether gradient (10%-50%) to afford the product as a yellow solid (2.9 g, 35%).

Example 21

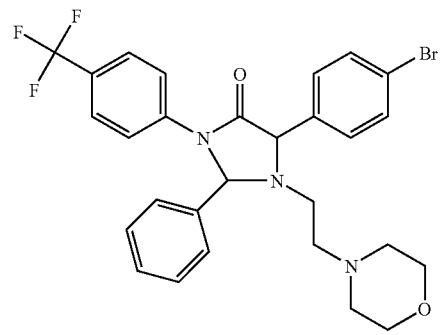

5-(4-Bromo-phenyl)-1-(2-morpholin-4-yl-ethyl)-2-phenyl-3-(4-trifluoromethyl-phenyl)-imidazolidin-4-one To a solution of 2-(4-bromo-phenyl)-2-(2-morpholin-4-yl-ethylamino)-N-(4-trifluoromethyl-phenyl)-acetamide (2.90 g, 6.00 mmol) in anhydrous MeOH (20 mL) was added benzaldehyde (633 mg, 6.00 mmol), followed by para-toluenesulfonic acid (229 mg, 1.20 mmol) and sodium sulfate (8.98 g, 63.2 mmol). The reaction was refluxed overnight, filtered, and directly purified by flash column chromatography eluting with ethyl acetate: petroleum ether gradient (10%-25%) to afford the product as a yellow solid (2.38 g, 69.2%).

Example 22

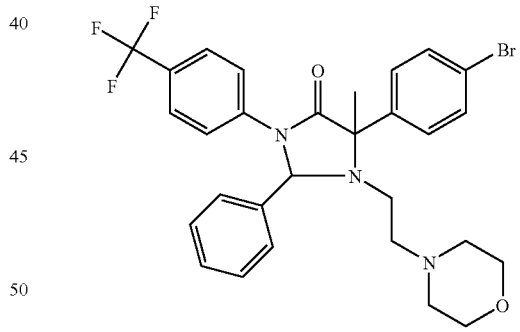

5-(4-Bromo-phenyl)-5-methyl-1-(2-morpholin-4-yl-ethyl)-2-phenyl-3-(4-trifluoromethyl-phenyl)-imidazolidin-4-one To a solution of 5-(4-bromo-phenyl)-1-(2-morpholin-4-yl-ethyl)-2-phenyl-3-(4-trifluoromethyl-phenyl)-imidazolidin-4-one (2.30 g, 4.00 mmol) in anhydrous THF (40 mL) at −78 degrees Celcius was added lithium diisopropylamide (5.3 mL, 1.5M solution of LDA in cyclohexane) and this stirred for 1 h. Methyl iodide (1.13 g, 8.00 mmol) was then added at −78 degrees Celcius and the reaction allowed to warm to room temperature over 2 hours. The reaction was then quenched with 2 equivalents of formic acid followed by NH₃.H₂O to basify the solution, diluted with ethyl acetate, washed with water and brine, and then dried over Na₂SO₄. After filtering and concentrating in vacuo, the crude product was purified by flash column chromatography eluting with ethyl acetate:petroleum ether gradient (10%-50%) to afford the product as a pale yellow solid (1.0 g, 43%).

Example 23

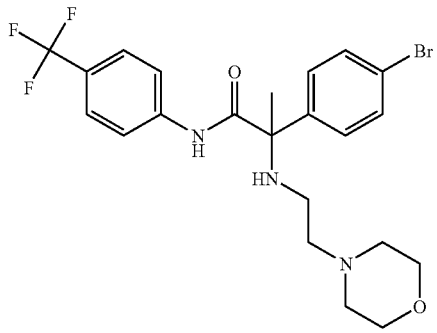

2-(4-Bromo-phenyl)-2-(2-morpholin-4-yl-ethylamino)-N-(4-trifluoromethyl-phenyl)-propionamide The 5-(4-bromo-phenyl)-5-methyl-1-(2-morpholin-4-yl-ethyl)-2-phenyl-3-(4-trifluoromethyl-phenyl)-imidazolidin-4-one (1.0 g, 1.7 mmol) was stirred vigorously in a solution of dichloromethane:conc. HCl (10 mL: 50 mL, v:v) overnight at 80 degrees Celcius. The resulting mixture was cooled to room temperature and the aqueous portion was extracted with dichloromethane. The aqueous portion was then basified to pH 11 with aqueous NaOH. The aqueous layer was then extracted with dichloromethane, washed with water and brine, dried over sodium sulfate, filtered, and concentrated in vacuo. The crude product was purified by flash column chromatography eluting with dichloromethane:methanol gradient (500:1 to 100:1, v/v) to afford the product as a pale yellow solid (233 mg, 27%). MS: calc'd 500 (MH+), exp 500 (MH+).

Example 24

(E)-[2-(3-{4-[1-(2-Morpholin-4-yl-ethylamino)-1-(4-trifluoromethyl-phenylcarbamoyl)-ethyl]-phenyl}-acryloylamino)-phenyl]-carbamic acid tert-butyl ester A mixture of (E)-2-(4-bromo-phenyl)-2-(2-morpholin-4-yl-ethylamino)-N-(4-trifluoromethyl-phenyl)-propionamide (233 mg, 0.466 mmol), (2-acryloylamino-phenyl)-carbamic acid tert-butyl ester (155 mg, 0.594 mmol), tri-o-tolyl-phosphine (33 mg, 0.110 mmol), triethylamine (272 mg, 2.69 mmol) and Pd₂(dba)₃ (49 mg, 0.052 mmol) in DMF (3 mL) was heated at 105 degrees Celcius for 1 hr under N₂ atmosphere, and then at 95 degrees Celcius overnight. After cooling to room temperature, the mixture was poured into a saturated aqueous solution of NH₄Cl and extracted with ethyl acetate four times. The organic layer was washed with brine, dried over Na₂SO₄, filtered, and concentrated in vacuo to obtain the crude product which was used without further purification.

Example 25

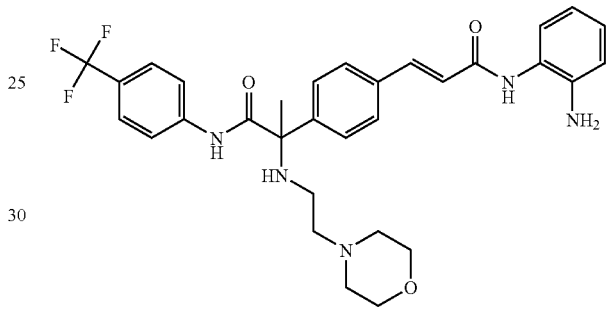

(E)-N-(2-Amino-phenyl)-3-{4-[1-(2-morpholin-4-yl-ethylamino)-1-(4-trifluoromethyl-phenylcarbamoyl)-ethyl]-phenyl}-acrylamide (E)-[2-(3-{4-[1-(2-Morpholin-4-yl-ethylamino)-1-(4-trifluoromethyl-phenylcarbamoyl)-ethyl]-phenyl}-acryloylamino)-phenyl]-carbamic acid tert-butyl ester (crude material from Example 24) was treated with 1.25M HCl in methanol (2.8 mL) at room temperature for 2 hours. The reaction was quenched slowly with solid sodium bicarbonate until the pH was 6-7. The mixture was diluted in acetonitrile with a small amount of dimethylsulfoxide, passed through a 40 µm pipette filter, and then purified by preparative HPLC to

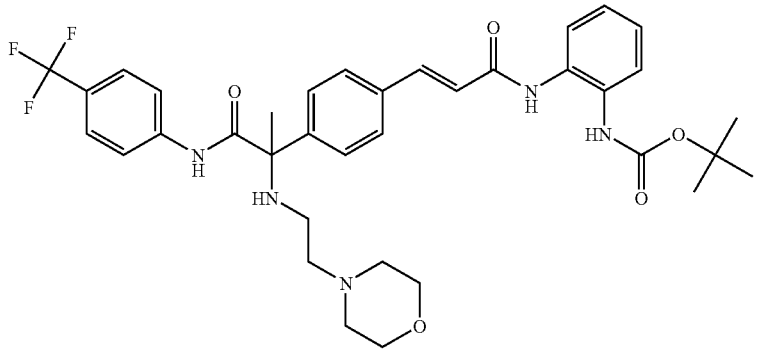

obtain the desired product (35 mg, 13%). MS: calc'd 582 (MH+), exp 582 (MH+). ¹H NMR (d₆-DMSO, 400 MHz) δ 10.5 (broad s, 1H), 9.39 (s, 1H), 7.88 (d, 2H, J=8.8 Hz), 7.68 (d, 2H, J=8.8 Hz), 7.62 (d, 2H, J=8.4 Hz), 7.57 (d, 2H, J=8.4 Hz), 7.54 (d, 1H, J=15.6 Hz), 7.35 (d, 1H, J=7.6 Hz), 6.92 (t, 1H, J=7.6 Hz), 6.90 (d, 1H, J=15.6 Hz), 6.75 (dd, 1H, J=8.0 Hz, 1.2 Hz), 6.57 (td, 1H, J=8.0 Hz, 1.2 Hz), 4.93 (s, 2H), 3.53 (m, 4H), 3.33 (m, 2H, overlapped with DMSO solvent residual peak), 2.55 (m, 2H), 2.30 (m, 4H), 1.65 (s, 3H).

Example 26

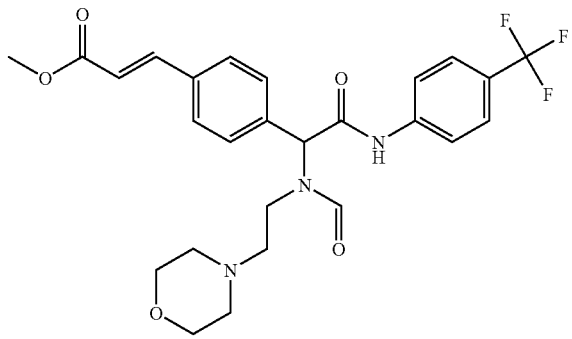

(E)-3-{4-[[Formyl-(2-morpholin-4-yl-ethyl)-amino]-(4-trifluoromethyl-phenylcarbamoyl)-methyl]-phenyl}-acrylic acid methyl ester A solution of 4-formylcinnamic acid methyl ester (3.66 g, 19.2 mmol), 4-(trifluoromethyl)-phenyl isocyanide (3.32 g, 19.2 mmol), 2-morpholinoethylamine (2.50 g, 19.2 mmol) and formic acid solution in methanol (12.9 mL, 1.5M) in methanol (9 mL) was stirred at 80 degrees Celcius for 8 hours. After solvent removal, the crude product was directly purified by flash column chromatography over silica gel (dichloromethane/methanol, 100:1 to 20:1, v:v) to yield the desired product (5 g, 50.2%). MS: calc'd 520 (MH+) exp 520 (MH+).

Example 27

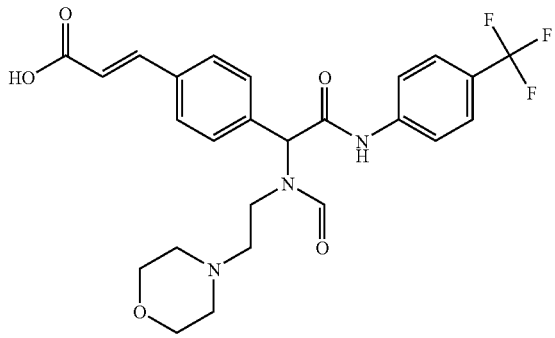

(E)-3-{4-[[Formyl-(2-morpholin-4-yl-ethyl)-amino]-(4-trifluoromethyl-phenylcarbamoyl)-methyl]-phenyl}-acrylic acid To a solution of (E)-3-{4-[[formyl-(2-morpholin-4-yl-ethyl)-amino]-(4-trifluoromethyl-phenylcarbamoyl)-methyl]-phenyl}-acrylic acid methyl ester (540 mg, 1.04 mmol) in THF (10 mL) was added aqueous 2M NaOH (3 ml) dropwise at 0 degrees Celcius, then this was stirred at room temperature overnight. The reaction was neutralized with dilute HCl solution, and the resulting precipitate filtered, and dried to obtain the desired product (216 mg, 41%). MS: calc'd 506 (MH+) exp 506 (MH+).

Example 28

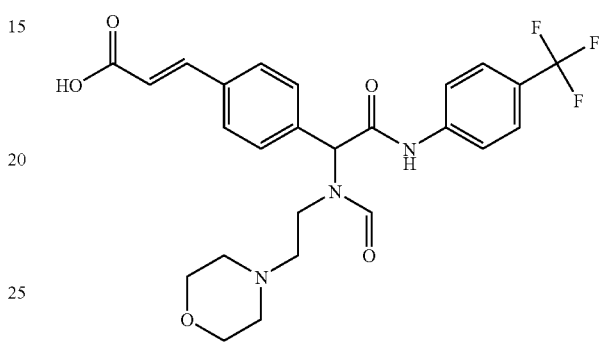

(E)-N-(2-Amino-5-fluoro-phenyl)-3-{4-[(2-morpholin-4-yl-ethylamino)-(4-trifluoromethyl-phenylcarbamoyl)-methyl]-phenyl}-acrylamide Step A: To a suspension of (E)-3-{4-[[formyl-(2-morpholin-4-yl-ethyl)-amino]-(4-trifluoromethyl-phenylcarbamoyl)-methyl]-phenyl}-acrylic acid (216 mg, 0.428 mmol) and 4-fluoro-1,2-phenylene diamine (59.3 mg, 0.471 mmol) in dichloromethane (5 mL) were added EDCI (114.2 mg, 0.471 mmol) and HOBt (63.6 mg, 0.471 mmol) successively. This reaction mixture was stirred at room temperature overnight. More dichloromethane was added, then this organic mixture was washed with water and brine, dried over anhydrous sodium sulfate, filtered, and concentrated under vacuum. The resulting residue was purified by flash column chromatography to yield the N-formylated intermediate (243 mg, 92.7%). MS: calc'd 614 (MH+) exp 614 (MH+).

Step B: The intermediate (243 mg, 0.396 mmol) from Step A was treated with 1.25M HCl in methanol (2.4 mL) at room temperature overnight. The reaction was quenched slowly with solid sodium bicarbonate until the pH was 6-7. The mixture was diluted in acetonitrile with a small amount of dimethylsulfoxide, passed through a 40 μm pipette filter, and then purified by preparative HPLC to obtain the desired product (63 mg, 27%). MS: calc'd 586 (MH+) exp 586 (MH+). ¹H NMR (d₆-DMSO, 400 MHz) δ10.5 (broad s, 1H), 9.32 (s, 1H), 7.85 (d, 2H, J=8.4 Hz), 7.68 (d, 2H, J=8.4 Hz), 7.60 (d, 2H, J=8.0 Hz), 7.54 (d, 1H, J=15.6 Hz), 7.53 (d, 2H, J=8.0 Hz), 7.28 (d, 1H, J=7.6 Hz), 6.85 (d, 1H, J=15.6 Hz), 6.52 (dd, 1H, J=11 Hz, 2.6 Hz), 6.35 (td, 1H, J=8.4 Hz, 2.6 Hz), 5.24 (s, 2H), 4.46 (s, 1H), 3.57 (m, 4H), 2.63 (m, 2H), 2.46 (m, 2H), 2.35 (m, 4H).

Example 29

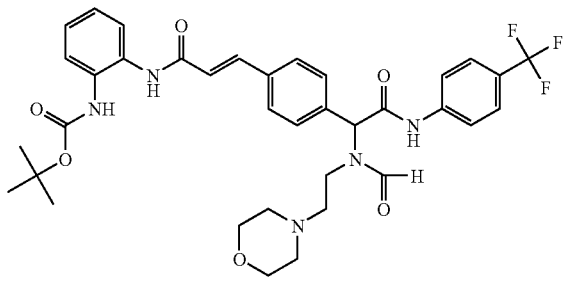

(E)-[2-(3-{4-[[Formyl-(2-morpholin-4-yl-ethyl)-amino]-(4-trifluoromethyl-phenylcarbamoyl)-methyl]-phenyl}-acryloylamino)-phenyl]-carbamic acid tert-butyl ester A solution of (E)-{2-[3-(4-formyl-phenyl)-acryloylamino]-phenyl}-carbamic acid tert-butyl ester (1.10 g, 3.00 mmol), 4-(trifluoromethyl)-phenyl isocyanide (520 mg, 3.00 mmol), 2-morpholinoethylamine (391 mg, 3.00 mmol) and formic acid solution in methanol (2.0 mL, 1.5M) in methanol (1.0 mL) was stirred at 80 degrees Celcius for 4 hours. After solvent removal, the crude product was directly purified by flash column chromatography over silica gel (dichloromethane/methanol, 100:1 to 10:1, v:v) to yield the desired product (730 mg, 35%). MS: calc'd 696 (MH+) exp 696 (MH+).

Example 30

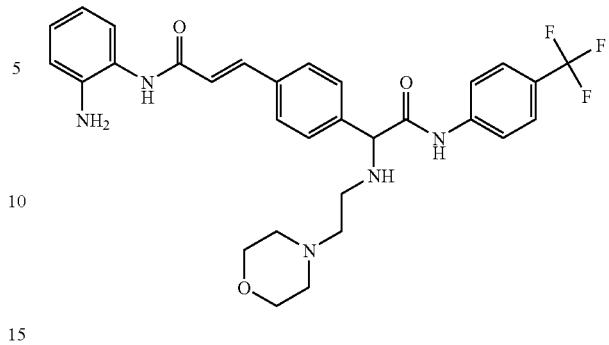

(E)-N-(2-Amino-phenyl)-3-{4-[(2-morpholin-4-yl-ethylamino)-(4-trifluoromethyl-phenylcarbamoyl)-methyl]-phenyl}-acrylamide (E)-[2-(3-{4-[[Formyl-(2-morpholin-4-yl-ethyl)-amino]-(4-trifluoromethyl-phenylcarbamoyl)-methyl]-phenyl}-acryloylamino)-phenyl]-carbamic acid tert-butyl ester (300 mg, 0.432 mmol) was treated with 1.25M HCl in methanol (2.6 mL) at room temperature overnight. The reaction was quenched slowly with solid sodium bicarbonate until the pH was 6-7. The mixture was diluted in acetonitrile with a small amount of dimethylsulfoxide, passed through a 40 μm pipette filter, and then purified by preparative HPLC to obtain the desired product (58 mg, 24%). MS: calc'd 568 (MH+) exp 568 (MH+). $^1$H NMR ($d_6$-DMSO, 400 MHz) δ 10.6 (broad s, 1H), 9.40 (s, 1H), 7.84 (d, 2H, J=8.4 Hz), 7.69 (d, 2H, J=8.4 Hz), 7.62 (d, 2H, J=8.0 Hz), 7.54 (d, 2H, J=8.0 Hz), 7.53 (d, 1H, J=15.6 Hz), 7.33 (d, 1H, J=7.6 Hz), 6.91 (t, 1H, J=7.6 Hz), 6.89 (d, 1H, J=15.6 Hz), 6.75 (d, 1H, J=7.2 Hz), 6.58 (t, 1H, J=7.2 Hz), 4.94 (broad s, 2H), 4.51 (broad s, 1H), 3.59 (m, 4H), 3.45 (m, 2H), 2.66 (m, 2H), 2.33 (m, 4H).

The compounds described in the following table 3 were prepared by methods analogous to the synthetic methods described above, but using the appropriate starting materials.

TABLE 3

| Cmpd # | Structure | MW | MS (MH+) calc'd | MS (MH+) exp |
|---|---|---|---|---|
| 30-1 | ![structure] | 476.58 | 477 | 477 |

TABLE 3-continued
| Cmpd # | Structure | MW | MS (MH+) calc'd | MS (MH+) exp |
|---|---|---|---|---|
| 30-2 | 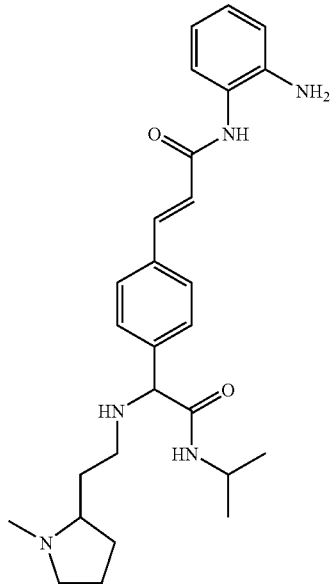 | 463.63 | 464 | 464 |
| 30-3 | 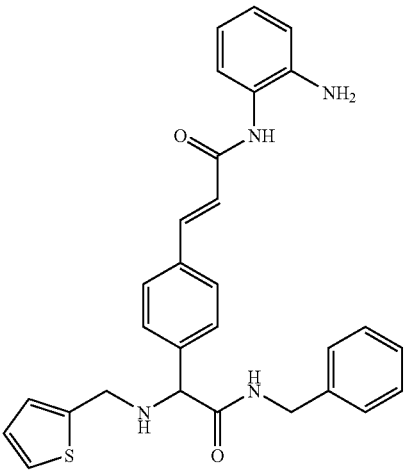 | 496.64 | 497 | 497 |

TABLE 3-continued

| Cmpd # | Structure | MW | MS (MH+) calc'd | MS (MH+) exp |
|---|---|---|---|---|
| 30-4 | 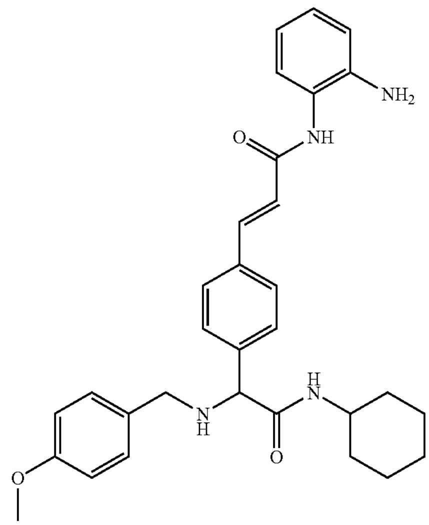 | 512.66 | 513 | 513 |
| 30-5 | 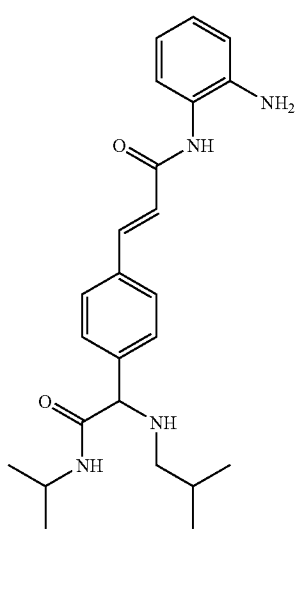 | 408.55 | 409 | 409 |

TABLE 3-continued

| Cmpd # | Structure | MW | MS (MH+) calc'd | MS (MH+) exp |
|---|---|---|---|---|
| 30-6 | 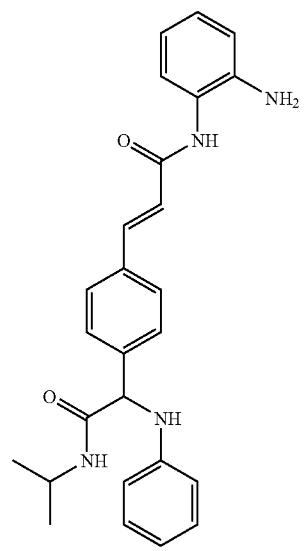 | 428.54 | 429 | 429 |
| 30-7 | 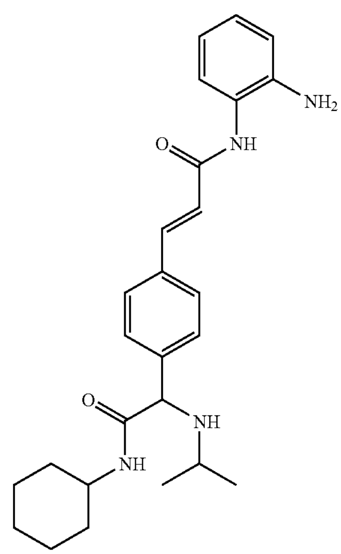 | 434.59 | 435 | 435 |
| 30-8 | 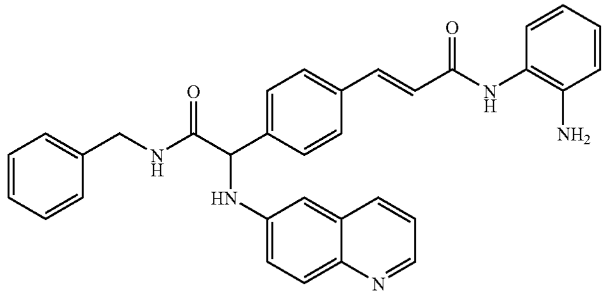 | 527.63 | 528 | 528 |

TABLE 3-continued
| Cmpd # | Structure | MW | MS (MH+) calc'd | MS (MH+) exp |
|---|---|---|---|---|
| 30-9 | 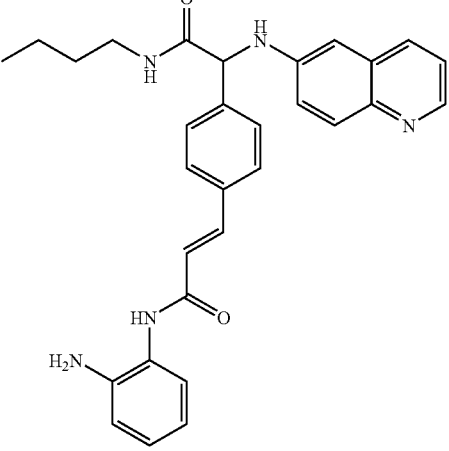 | 493.61 | 494 | 494 |
| 30-10 | 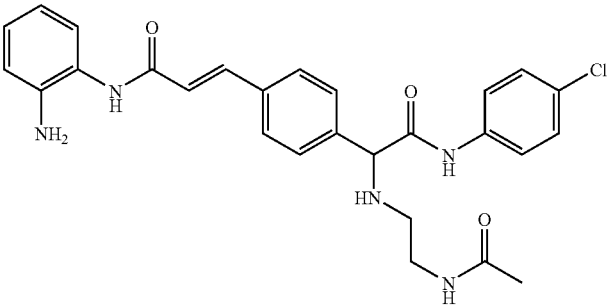 | 506.01 | 506 | 506 |
| 30-11 | 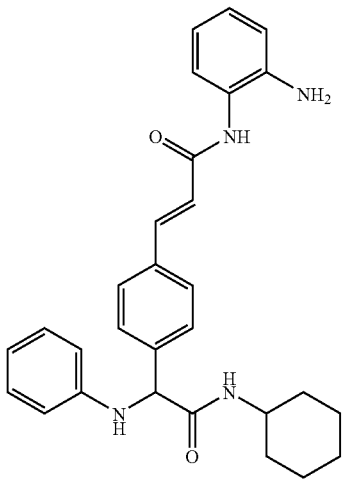 | 468.60 | 469 | 469 |

TABLE 3-continued

| Cmpd # | Structure | MW | MS (MH+) calc'd | MS (MH+) exp |
| --- | --- | --- | --- | --- |
| 30-12 | 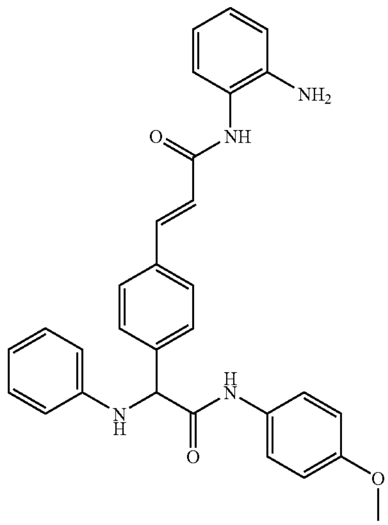 | 492.58 | 493 | 493 |
| 30-13 | 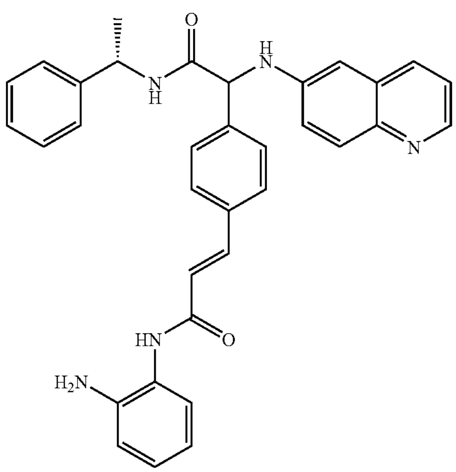 | 541.66 | 542 | 542 |
| 30-14 | 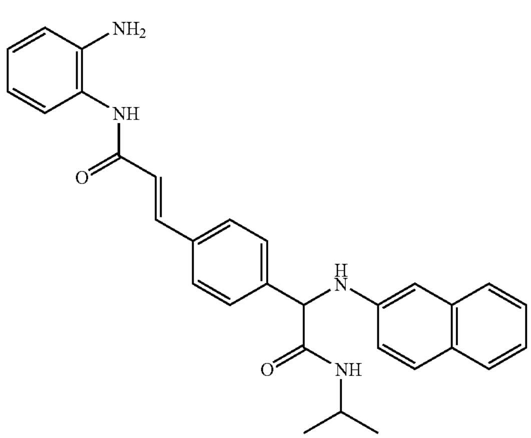 | 478.60 | 479 | 479 |

TABLE 3-continued

| Cmpd # | Structure | MW | MS (MH+) calc'd | MS (MH+) exp |
|---|---|---|---|---|
| 30-15 | 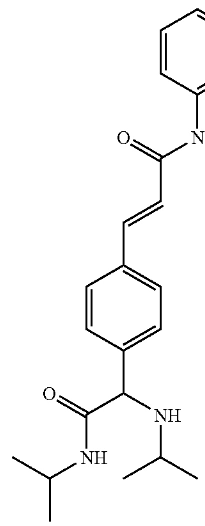 | 394.52 | 395 | 395 |
| 30-16 | 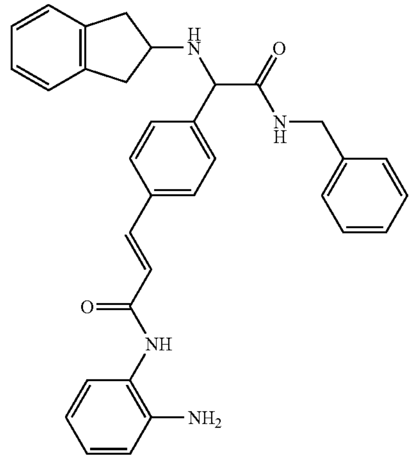 | 516.65 | 517 | 517 |
| 30-17 | 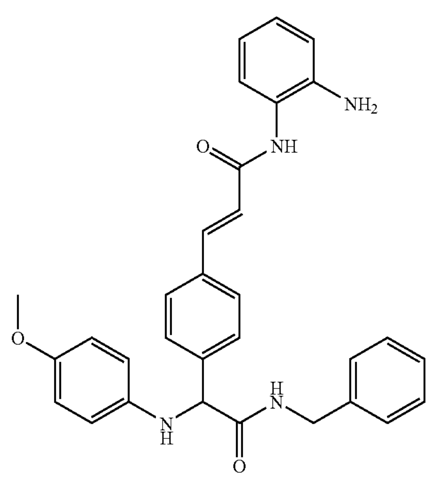 | 506.61 | 507 | 507 |

TABLE 3-continued

| Cmpd # | Structure | MW | MS (MH+) calc'd | MS (MH+) exp |
|---|---|---|---|---|
| 30-18 | 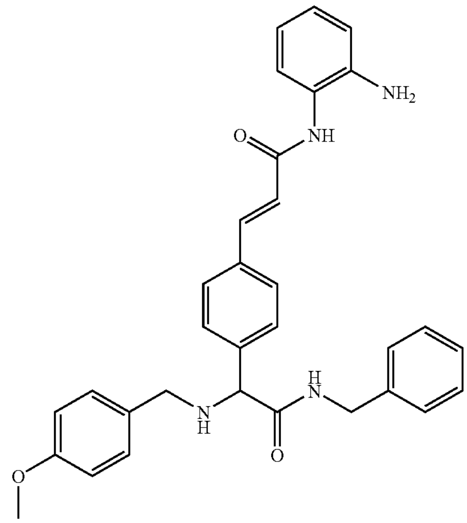 | 520.64 | 521 | 521 |
| 30-19 | 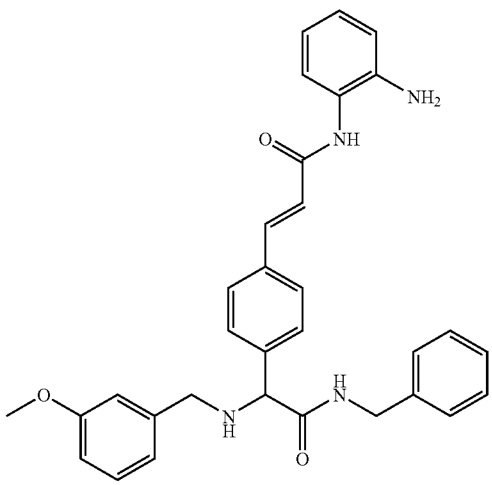 | 520.64 | 521 | 521 |
| 30-20 | 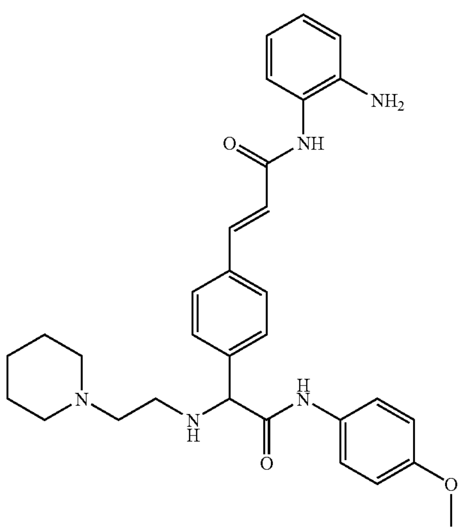 | 527.67 | 528 | 528 |

TABLE 3-continued

| Cmpd # | Structure | MW | MS (MH+) calc'd | MS (MH+) exp |
|---|---|---|---|---|
| 30-21 | 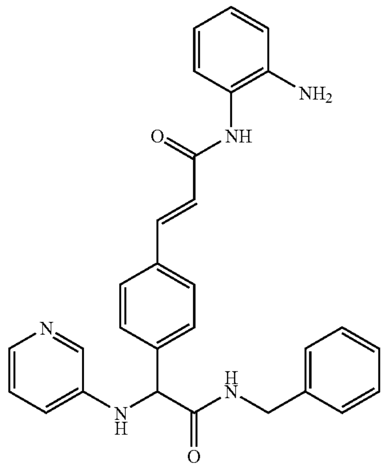 | 477.57 | 478 | 478 |
| 30-22 | 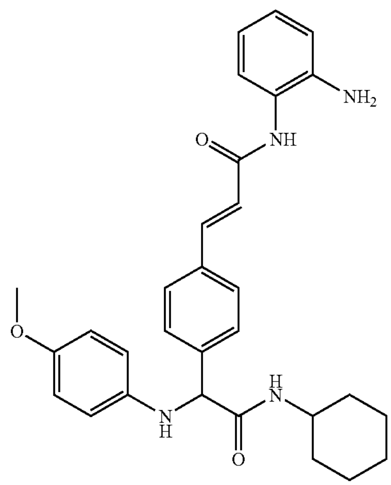 | 498.63 | 499 | 499 |
| 30-23 | 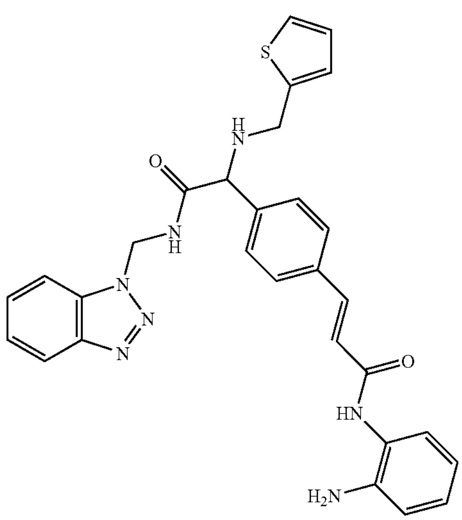 | 537.65 | 538 | 538 |

TABLE 3-continued
| Cmpd # | Structure | MW | MS (MH+) calc'd | MS (MH+) exp |
|---|---|---|---|---|
| 30-24 | 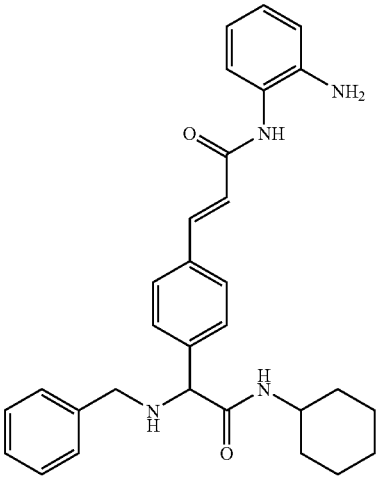 | 482.63 | 483 | 483 |
| 30-25 | 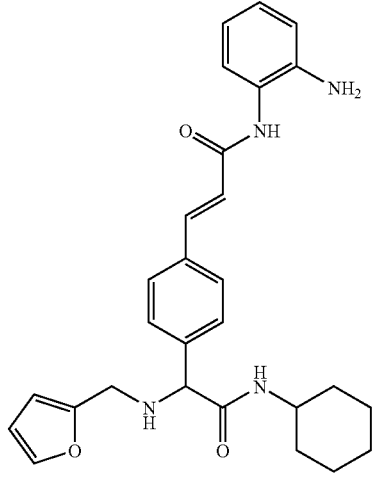 | 472.59 | 473 | 473 |
| 30-26 | 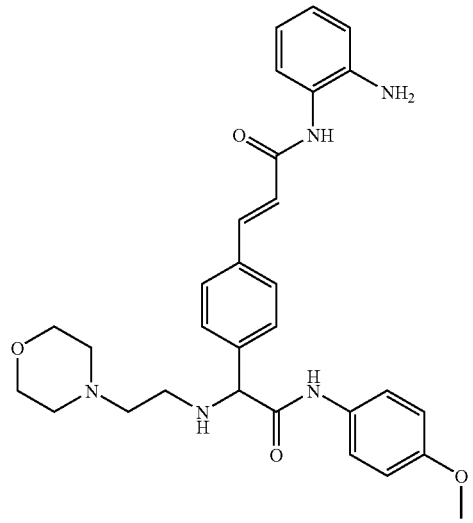 | 529.64 | 530 | 530 |

TABLE 3-continued

| Cmpd # | Structure | MW | MS (MH+) calc'd | MS (MH+) exp |
|---|---|---|---|---|
| 30-27 | 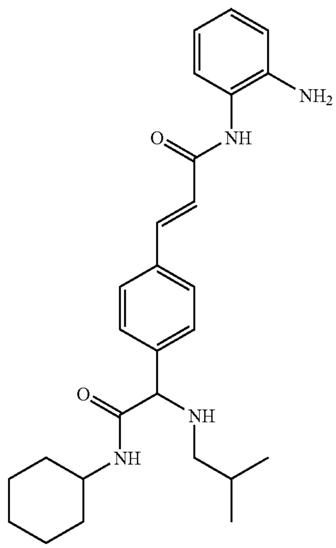 | 448.61 | 449 | 449 |
| 30-28 | 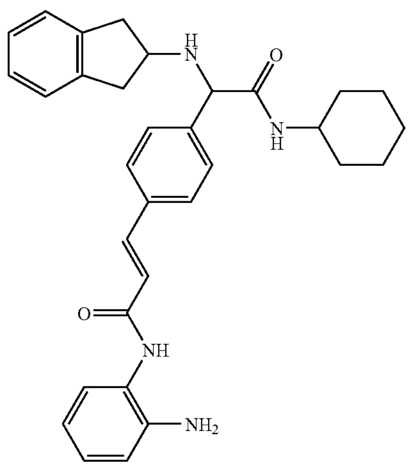 | 508.67 | 509 | 509 |
| 30-29 | 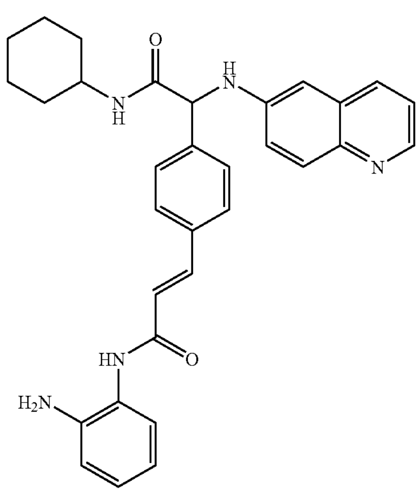 | 519.65 | 520 | 520 |

TABLE 3-continued
| Cmpd # | Structure | MW | MS (MH+) calc'd | MS (MH+) exp |
|---|---|---|---|---|
| 30-30 | 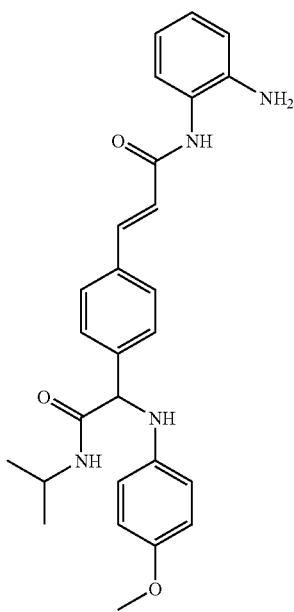 | 458.57 | 459 | 459 |
| 30-31 | 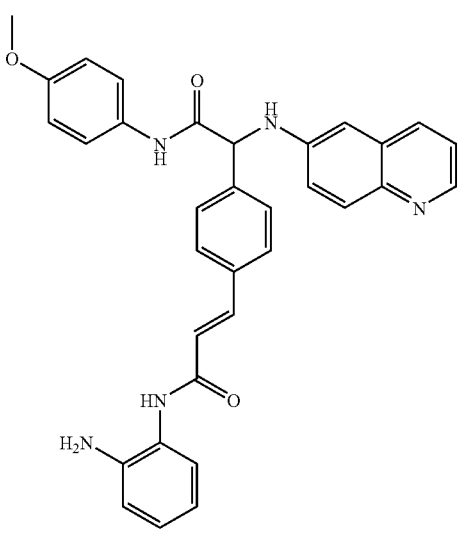 | 543.63 | 544 | 544 |

TABLE 3-continued

| Cmpd # | Structure | MW | MS (MH+) calc'd | MS (MH+) exp |
|---|---|---|---|---|
| 30-32 | 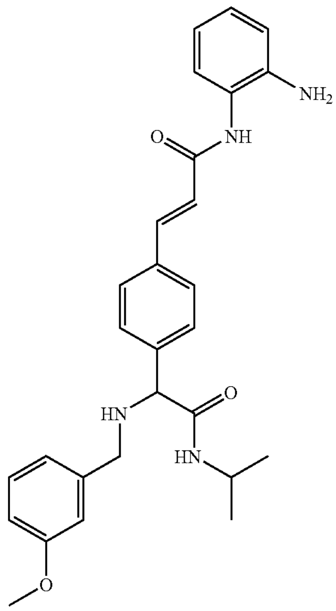 | 472.59 | 473 | 473 |
| 30-33 | 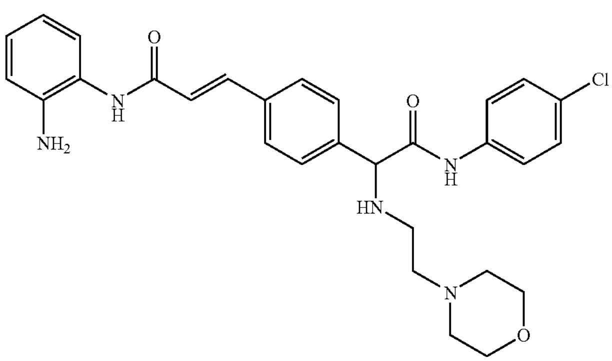 | 534.06 | 534 | 534 |

TABLE 3-continued

| Cmpd # | Structure | MW | MS (MH+) calc'd | MS (MH+) exp |
|---|---|---|---|---|
| 30-34 | 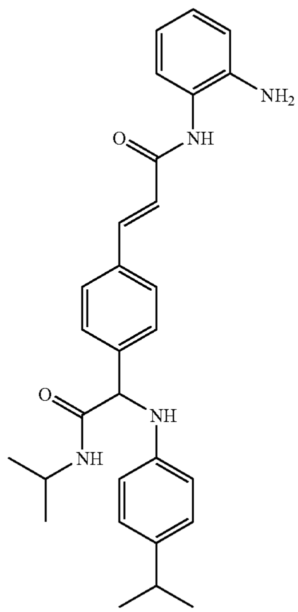 | 470.62 | 471 | 471 |
| 30-35 | 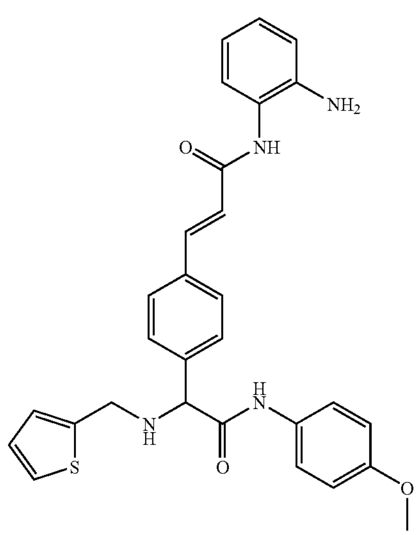 | 512.64 | 513 | 513 |

TABLE 3-continued

| Cmpd # | Structure | MW | MS (MH+) calc'd | MS (MH+) exp |
|---|---|---|---|---|
| 30-36 | 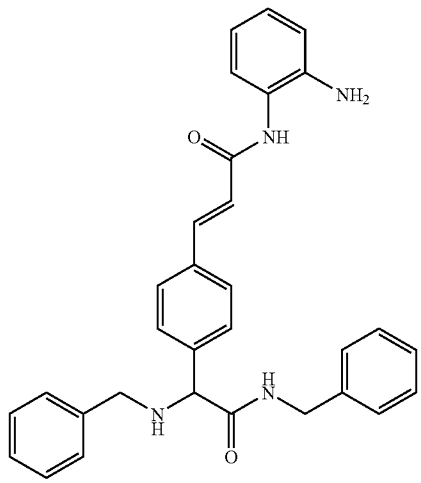 | 490.61 | 491 | 491 |
| 30-37 | 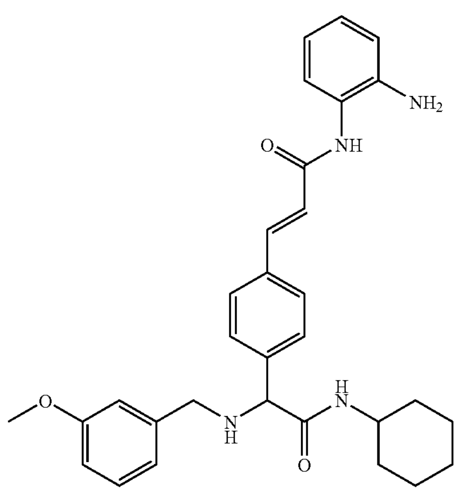 | 512.66 | 513 | 513 |

TABLE 3-continued

| Cmpd # | Structure | MW | MS (MH+) calc'd | MS (MH+) exp |
|---|---|---|---|---|
| 30-38 | 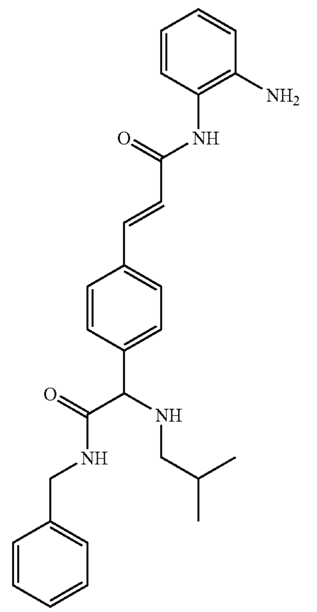 | 456.59 | 457 | 457 |
| 30-39 | 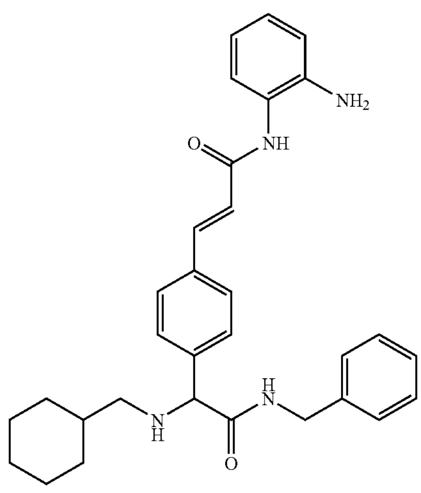 | 496.66 | 497 | 497 |
| 30-40 | 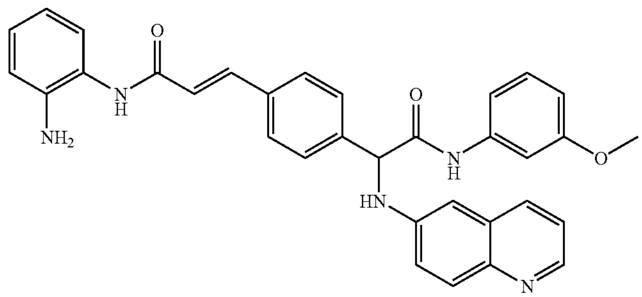 | 543.63 | 544 | 544 |

TABLE 3-continued

| Cmpd # | Structure | MW | MS (MH+) calc'd | MS (MH+) exp |
|---|---|---|---|---|
| 30-41 | 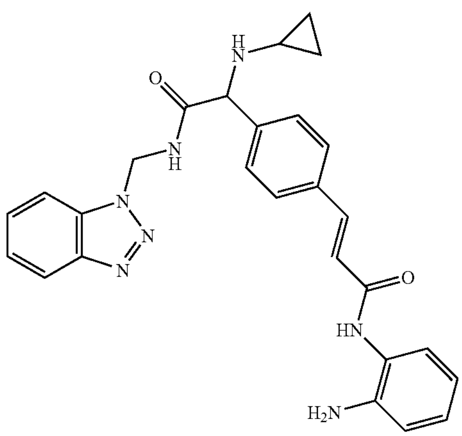 | 481.56 | 482 | 482 |
| 30-42 | 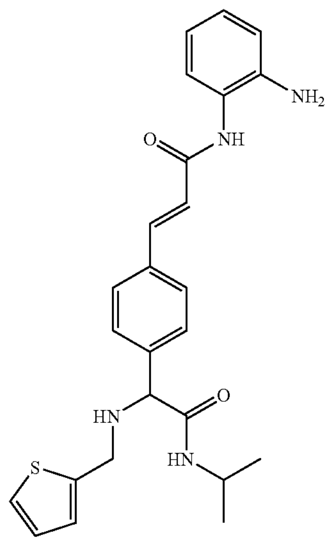 | 448.59 | 449 | 449 |
| 30-43 | 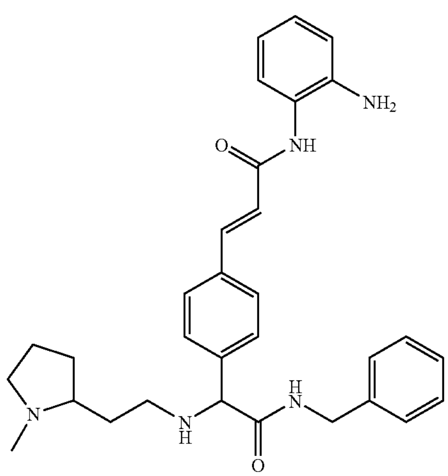 | 511.67 | 512 | 512 |

TABLE 3-continued

| Cmpd # | Structure | MW | MS (MH+) calc'd | MS (MH+) exp |
|---|---|---|---|---|
| 30-44 | 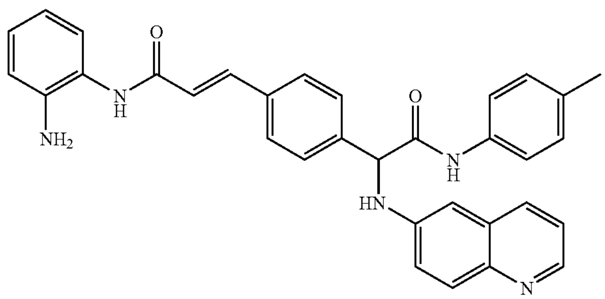 | 527.63 | 528 | 528 |
| 30-45 | 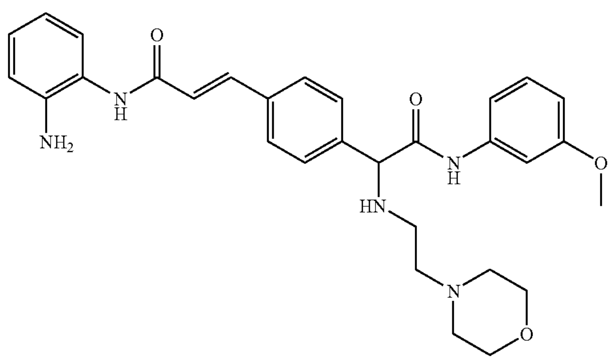 | 529.64 | 530 | 530 |
| 30-46 | 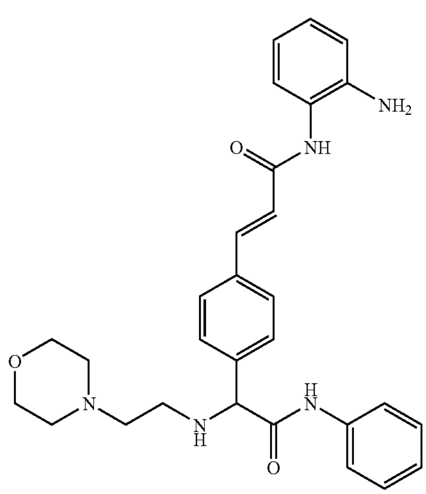 | 499.62 | 500 | 500 |

TABLE 3-continued

| Cmpd # | Structure | MW | MS (MH+) calc'd | MS (MH+) exp |
|---|---|---|---|---|
| 30-47 | 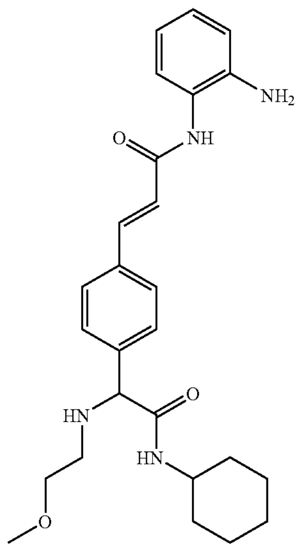 | 450.59 | 451 | 451 |
| 30-48 | 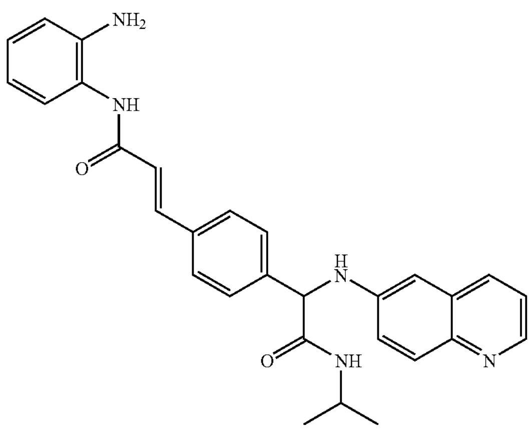 | 479.59 | 480 | 480 |
| 30-49 | 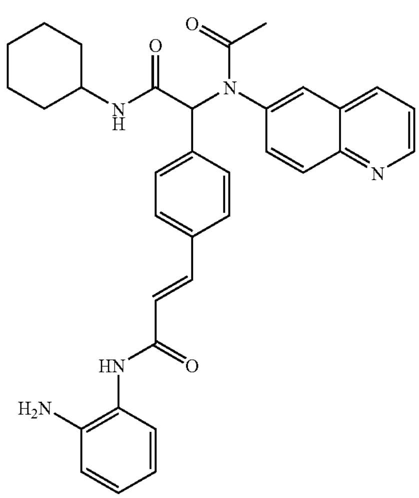 | 561.69 | 562 | 562 |

TABLE 3-continued

| Cmpd # | Structure | MW | MS (MH+) calc'd | MS (MH+) exp |
|---|---|---|---|---|
| 30-50 | 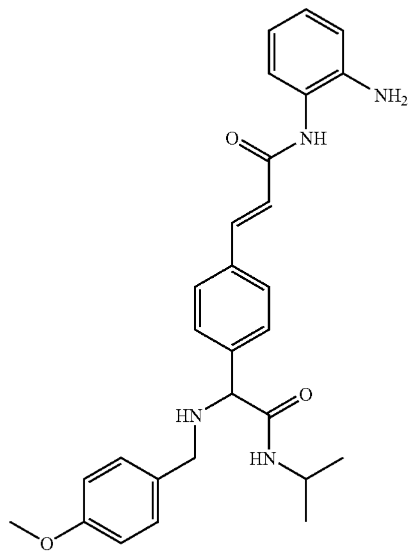 | 472.59 | 473 | 473 |
| 30-51 | 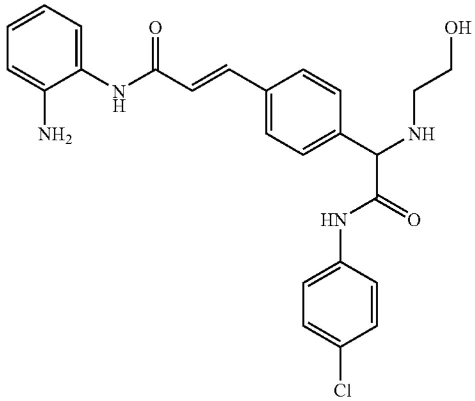 | 464.96 | 465 | 465 |
| 30-52 | 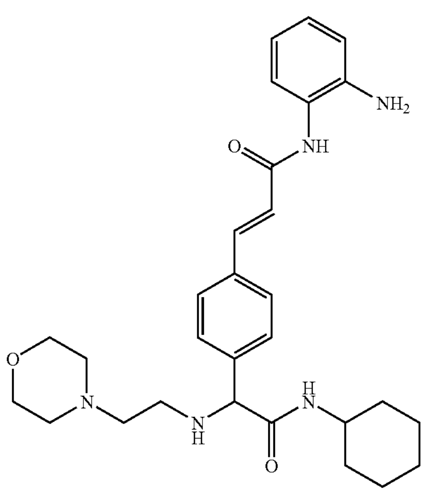 | 505.67 | 506 | 506 |

TABLE 3-continued

| Cmpd # | Structure | MW | MS (MH+) calc'd | MS (MH+) exp |
|---|---|---|---|---|
| 30-53 | 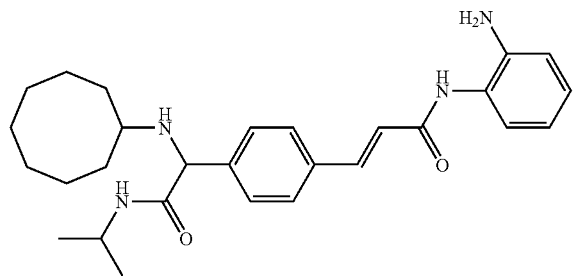 | 462.64 | 463 | 463 |
| 30-54 | 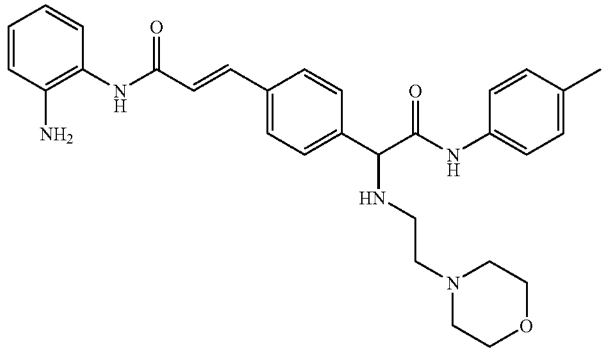 | 513.65 | 514 | 514 |
| 30-55 | 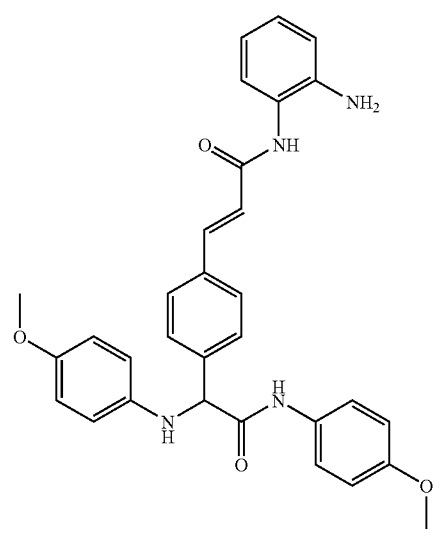 | 522.61 | 523 | 523 |

TABLE 3-continued
| Cmpd # | Structure | MW | MS (MH+) calc'd | MS (MH+) exp |
|---|---|---|---|---|
| 30-56 | 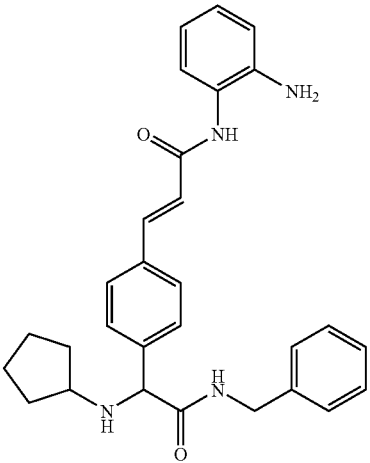 | 468.60 | 469 | 469 |
| 30-57 | 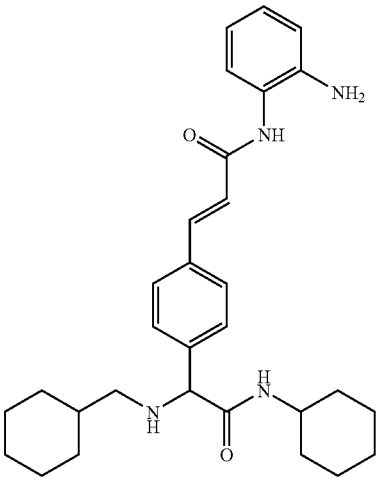 | 488.68 | 489 | 489 |
| 30-58 | 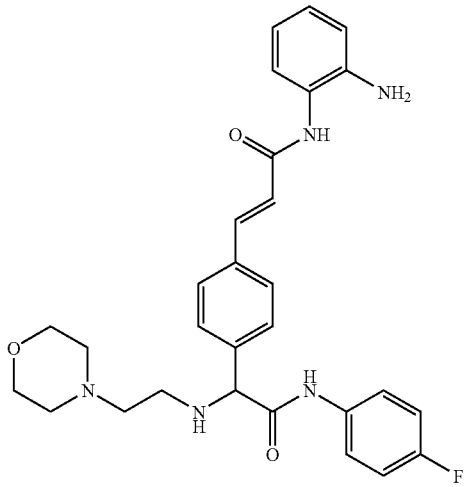 | 517.61 | 518 | 518 |

TABLE 3-continued
| Cmpd # | Structure | MW | MS (MH+) calc'd | MS (MH+) exp |
|---|---|---|---|---|
| 30-59 | 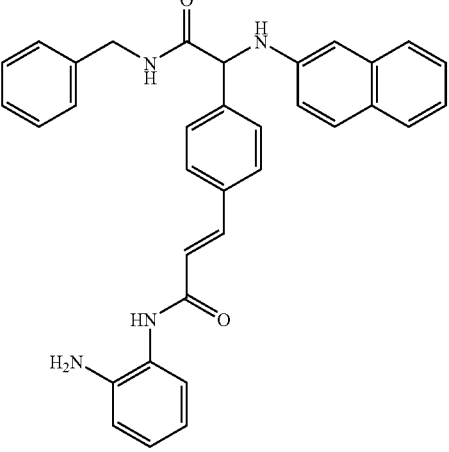 | 526.64 | 527 | 527 |
| 30-60 | 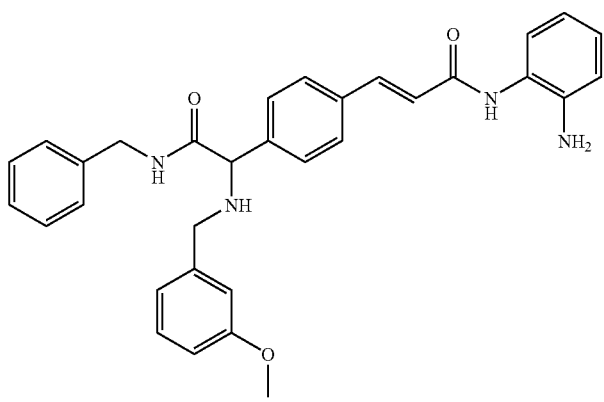 | 520.64 | 521 | 521 |
| 30-61 | 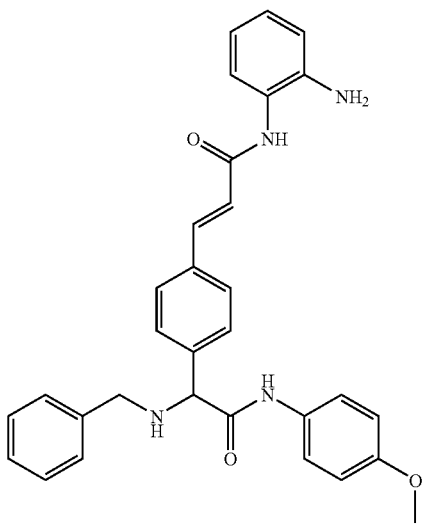 | 506.61 | 507 | 507 |

TABLE 3-continued
| Cmpd # | Structure | MW | MS (MH+) calc'd | MS (MH+) exp |
|---|---|---|---|---|
| 30-62 | 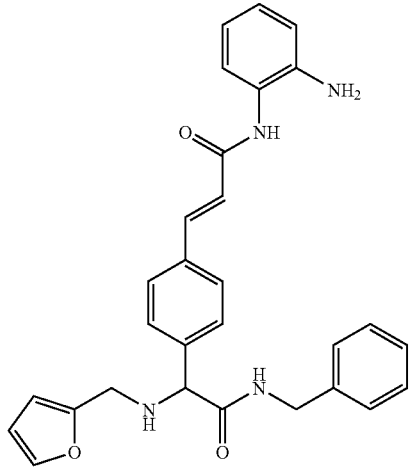 | 480.57 | 481 | 481 |
| 30-63 | 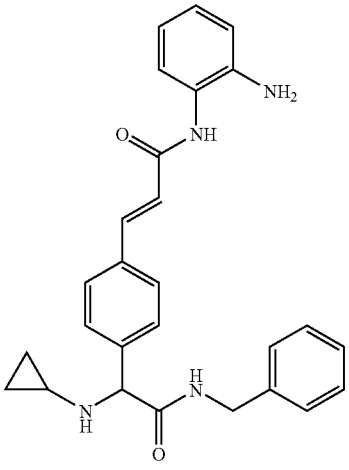 | 440.55 | 441 | 441 |
| 30-64 | 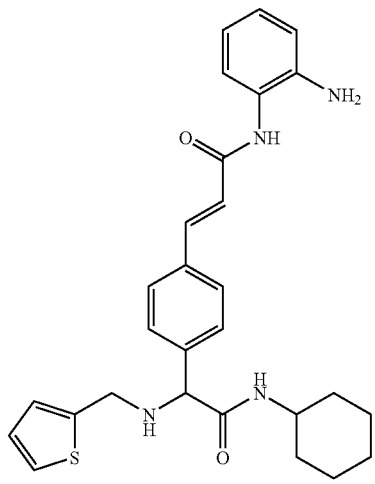 | 488.66 | 489 | 489 |

TABLE 3-continued
| Cmpd # | Structure | MW | MS (MH+) calc'd | MS (MH+) exp |
|---|---|---|---|---|
| 30-65 | 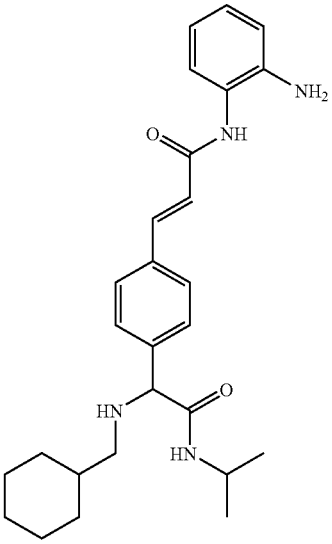 | 448.61 | 449 | 449 |
| 30-66 | 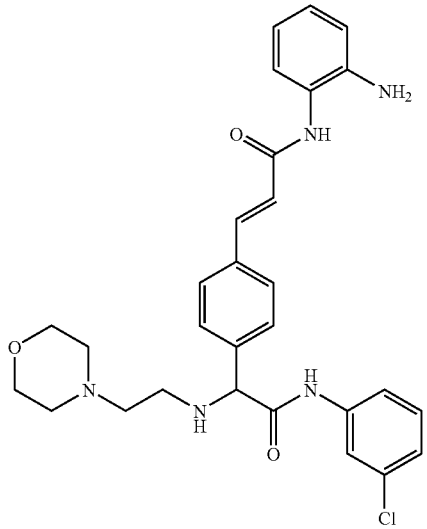 | 534.06 | 534 | 534 |
| 30-67 | 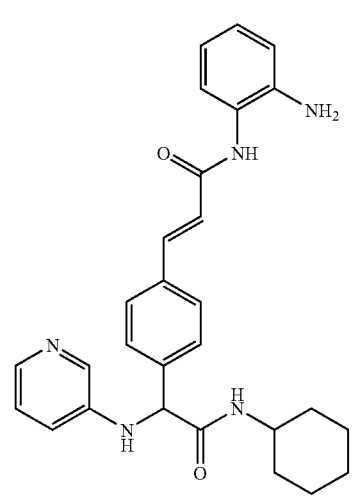 | 469.59 | 470 | 470 |

TABLE 3-continued

| Cmpd # | Structure | MW | MS (MH+) calc'd | MS (MH+) exp |
|---|---|---|---|---|
| 30-68 | 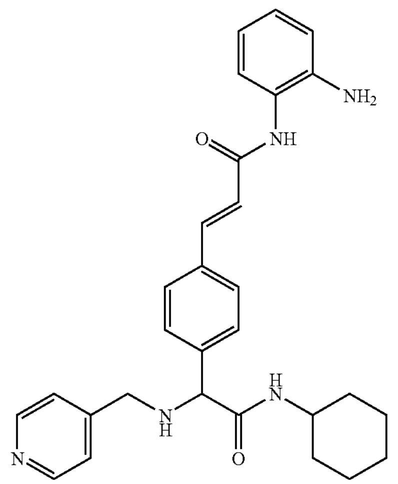 | 483.62 | 484 | 484 |
| 30-69 | 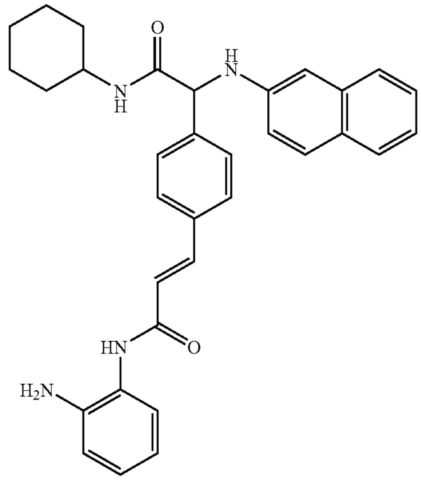 | 518.66 | 519 | 519 |
| 30-70 | 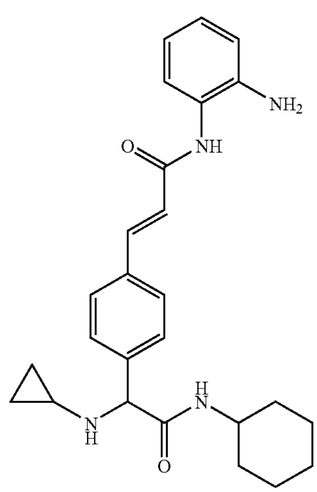 | 432.57 | 433 | 433 |

TABLE 3-continued

| Cmpd # | Structure | MW | MS (MH+) calc'd | MS (MH+) exp |
|---|---|---|---|---|
| 30-71 | 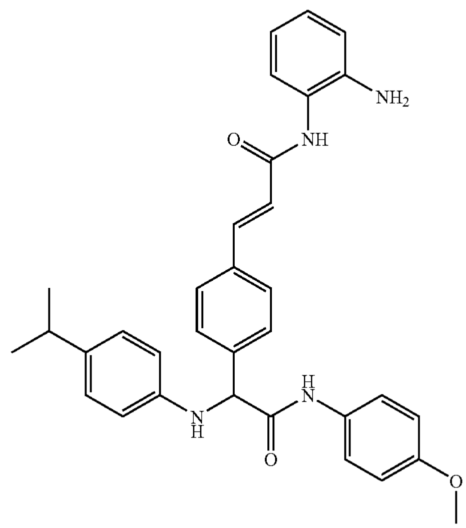 | 534.66 | 535 | 535 |
| 30-72 | 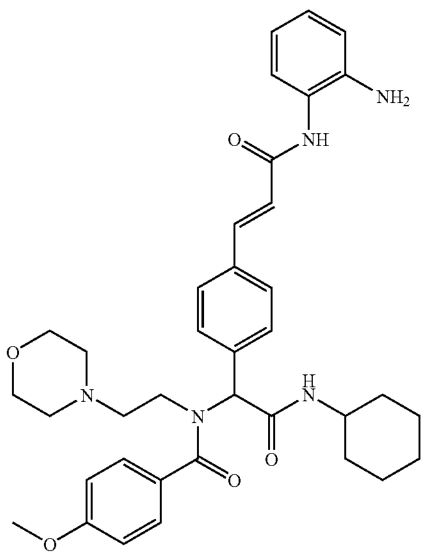 | 639.80 | 640 | 640 |

Example 31

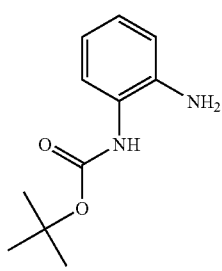

(2-Amino-phenyl)-carbamic acid tert-butyl ester

To a solution of o-phenylenediamine (54.0 g, 0.500 mol) in THF (500 mL) was added (Boc)$_2$O (109 g, 0.500 mol) in THF (150 mL) dropwise, and the mixture was stirred at room temperature overnight. After concentration under vacuum, the residue was diluted with ethyl acetate/petroleum ether=1/4 (v/v) (150 mL) and the precipitate was collected. The mother liquor was concentrated and the crude product was recrystallized with ethyl acetate/petroleum ether=1/4 (v/v). The combined solids were dried in vacuo at 40 degrees Celcius for 4 hours. An off-white solid (80 g, 77%) was obtained. MS: calc'd 209 (MH+), exp 209 (MH+). $^1$H NMR (CDCl$_3$, 400 MHz) δ 7.25 (m, 1H), 7.00 (m, 1H), 6.77 (m, 2H), 6.29 (broad m, 1H), 3.60 (broad m, 2H), 1.51 (s, 9H).

Example 32

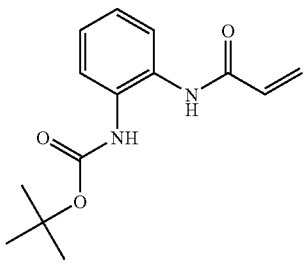

(2-Acryloylamino-phenyl)-carbamic acid tert-butyl ester

To a solution of acrylic acid (2.50 g, 34.7 mmol) in dichloromethane (80 mL) at 0 degrees Celcius was added N-methylmorpholine (4.73 g, 46.8 mmol), followed by isobutyl chloroformate (6.37 g, 46.8 mmol). After 30 minutes, a solution of (2-amino-phenyl)-carbamic acid tertbutyl ester (5.80 g, 27.8 mmol) in dichloromethane (50 mL) was added dropwise to the refluxing reaction mixture over 30 min. After the reaction was completed (2 hours later), the reaction mixture was allowed to cool down to room temperature, poured into ice water, and extracted with dichloromethane (30 mL×3). The organic layer was washed with water, dilute sodium bicarbonate solution, 0.1M HCl, water, and brine in turn. The organic layer was dried over sodium sulfate, filtered, and concentrated in vacuo. The crude solid was recrystallized from ethyl acetate/petroleum ether=1/4 (v/v) to obtain the desired product (2.5 g, 34%). MS: calc'd 263 (MH+), exp 263 (MH+).

Example 33

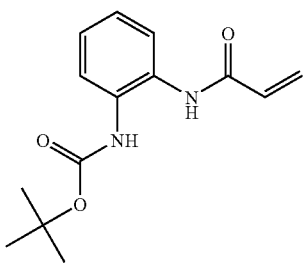

(E)-{2-[3-(4-Formyl-phenyl)-acryloylamino]-phenyl}-carbamic acid tert-butyl ester A mixture of (2-acryloylamino-phenyl)-carbamic acid tert-butyl ester (20.0 g, 76.3 mmol), 4-bromobenzaldehyde (14.4 g, 77.8 mmol), Pd$_2$(dba)$_3$ (0.56 g, 0.61 mmol), tri-o-tolylphosphine (0.370 g, 1.22 mmol) and triethylamine (42.1 mL, 0.300 mol) in DMF (300 mL) was stirred at 100 degrees Celcius under N$_2$ for 5 hours. The reaction mixture was allowed to cool down to room temperature and poured into a saturated aqueous solution of NH$_4$Cl. The precipitate was filtered off and washed with water, dried in vacuo at 40° C. overnight. The crude product was purified by flash column chromatography to obtain a yellow solid (15.5 g, 56%). MS: calc'd 367 (MH+), exp 367 (MH+). $^1$H NMR (d$_6$-DMSO, 400 MHz) δ 10.0 (s, 1H), 9.79 (s, 1H), 8.53 (s, 1H), 7.98 (d, 2H, J=8.0 Hz), 7.87 (d, 2H, J=8.0 Hz), 7.68 (d, 1H, J=16 Hz), 7.60 (m, 2H), 7.14 (m, 2H), 7.10 (d, 1H, J=16 Hz), 1.46 (s, 9H).

Example 34

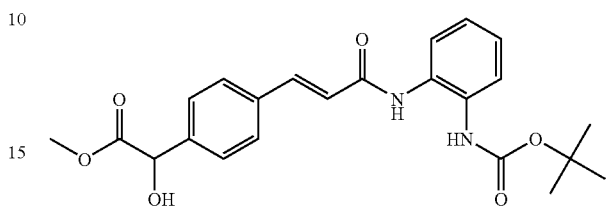

(E)-{4-[2-(2-tert-Butoxycarbonylamino-phenylcarbamoyl)-vinyl]-phenyl}-hydroxy-acetic acid methyl ester A mixture of 2-acryloylamino-phenyl)-carbamic acid tert-butyl ester (23 g, 87.7 mmol), methyl-2-(4-bromophenyl)-2-hydroxyacetate (25.6 g, 104.5 mmol), tri-o-tolyl-phosphine (2.8 g, 9.2 mmol), Et$_3$N (35.8 g, 353.8 mmol) and Pd$_2$(dba)$_3$ (4.3 g, 4.7 mmol) in DMF (400 mL) was heated at 100 degrees Celcius for 6 hours under N$_2$ atmosphere, monitored by TLC. After cooling to room temperature, the mixture was poured into a saturated aqueous solution of NH$_4$Cl, and extracted with ethyl acetate. The organic layer was washed with brine, dried over Na$_2$SO$_4$, filtered, concentrated in vacuo, and purified by flash column chromatography (ethyl acetate/petroleum ether 1:2) to obtain pale yellow solid (22.4 g, 60%). MS: calc'd 427 (MH+), exp 427 (MH+). $^1$H NMR (d$_6$-DMSO, 400 MHz) δ 9.71 (s, 1H), 8.48 (s, 1H), 7.64 (d, 2H, J=8.0 Hz), 7.59 (d, 1H, J=15.6 Hz), 7.57 (m, 1H), 7.48 (d, 2H, J=8.0 Hz), 7.14 (m, 2H), 6.92 (d, 1H, J=15.6, 6.17 (d, 1H, J=5.2 Hz), 5.21 (d, 1H, J=4.8 Hz), 3.64 (s, 3H), 1.47 (s, 9H).

Example 35

HDAC Inhibition by Novel Compounds: HeLa Extract HDAC Fluorometric Assay

Novel compounds were tested for their ability to inhibit histone deacetylase using an in vitro deacetylation assay. The enzyme source for this assay was HeLa nuclear extract. The substrate consisted of a commercial product containing an acetylated lysine side chain (both HeLa extract and substrate are available commercially from BIOMOL Research Laboratories, Inc., Plymouth Meeting, Pa.). After deacetylation of the substrate by incubation with HeLa nuclear extract, subsequent exposure to a developing reagent produces a fluorophore that is directly proportional to the level of deacetylation. Using the substrate concentration at the K$_m$ for the HeLa nuclear extract, the deacetylation assay was performed in the presence of novel compounds at 30 micromolar and the percent enzyme inhibition relative to a known reference HDAC inhibitor (SNDX-275) was determined. The compounds of the instant invention described in the Examples and Tables above exhibit histone deacetylase inhibitory activity in the range of about 65% to 180% relative to the known reference compound. Inhibitory activity for specific representative compounds can be found in Table 4.

Example 36 p21 Reporter Gene Induction by Novel Compounds

The novel compounds of the present invention were tested for their ability to induce p21 gene expression using a reporter gene assay involving HeLa cells transfected with a p21 promoter-luciferase construct. The p21 promoter contained the Sp1/Sp3 binding site for HDAC but not the upstream p53 binding site. Briefly, the day before transfection, HeLa cells were seeded at 11,000 cells/well in a 96-well culture plate and incubated at 37 degrees Celcius in 5% $CO_2$ overnight. For transfection, the medium was removed and replaced with 100 microliters/well transfection media previously prepared as follows: 5 microliters serum-free DMEM, 0.15 microliters Fugene 6 reagent, 40 ng p21-luc, 10 ng GFP were mixed gently and incubated at room temperature for 30 minutes; then 98 microliters DMEM (with 10% FBS, 1% penicillin and streptomycin) was added to the DNA:Fugene 6 reagent complex and mixed gently. After incubating the cells for 24 hours at 37 degrees Celcius in 5% $CO_2$, fresh media and test compounds were added to the wells and the cells further incubated for 15 hours at 37 degrees Celcius in 5% $CO_2$. Cells were lysed by adding 80 microliters/well of a cell culture lysis reagent (Promega). 50 microliters of each lysate was taken for GFP detection using an excitation wavelength of 486 nm and detection at 527 nm. 100 microliters Luciferase assay reagent (Promega) was then added to every 20 microliters cell lysate for luminometer detection. The compounds of the instant invention described in the Examples and Tables above exhibit p21 induction activity in the range of about 10% to 320% relative to the known HDAC inhibitor (SNDX-275) at a concentration of 3 micromolar. Induction activity for specific representative compounds can be found in Table 4.

Example 37 gdf11 Reporter Gene Induction by Novel Compounds

The novel compounds of the present invention were tested for their ability to induce gdf11 (growth differentiation factor 11) gene expression using a reporter gene assay involving HeLa cells transfected with a gdf11 promoter-luciferase construct. The gdf11 promoter has been reported to be negatively regulated by HDAC3 (*Mol. Cell. Bio.* 2004, 24, 5106-5118). Briefly, the day before transfection, HeLa cells were seeded at 11,000 cells/well in a 96-well culture plate and incubated at 37 degrees Celcius in 5% $CO_2$ overnight. For transfection, the medium was removed and replaced with 100 microliters/well transfection media previously prepared as follows: 5 microliters serum-free DMEM, 0.15 microliters Fugene 6 reagent, 40 ng gdf11-luc, 10 ng GFP were mixed gently and incubated at room temperature for 30 minutes; then 98 microliters DMEM (with 10% FBS, 1% penicillin and streptomycin) was added to the DNA:Fugene 6 reagent complex and mixed gently. After incubating the cells for 24 hours at 37 degrees Celcius in 5% $CO_2$, fresh media and test compounds were added to the wells and the cells further incubated for 15 hours at 37 degrees Celcius in 5% $CO_2$. Cells were lysed by adding 80 microliters/well of a cell culture lysis reagent (Promega). 50 microliters of each lysate was taken for GFP detection using an excitation wavelength of 486 nm and detection at 527 nm. 100 microliters Luciferase assay reagent (Promega) was then added to every 20 microliters cell lysate for luminometer detection. The compounds of the instant invention described in the Examples and Tables above exhibit gdf11 induction activity in the range of about 20% to 200% relative to the known HDAC inhibitor (SNDX-275) at a concentration of 3 micromolar. Induction activity for specific representative compounds can be found in Table 4.

Example 38 klf2 Reporter Gene Induction by Novel Compounds

The novel compounds of the present invention were tested for their ability to induce klf2 gene expression using a reporter gene assay involving A204 cells transfected with a klf2 promoter-luciferase construct. The klf2 promoter contained the MEF2 binding site for HDAC3/class IIa HDAC complex. Briefly, the day before transfection, A204 cells were seeded at 11,000 cells/well in a 96-well culture plate and incubated at 37 degrees Celcius in 5% $CO_2$ overnight. For transfection, the medium was removed and replaced with 100 microliters/well transfection media previously prepared as follows: 5 microliters serum-free DMEM, 0.15 microliters Fugene 6 reagent, 40 ng klf2-luc, 10 ng GFP were mixed gently and incubated at room temperature for 30 minutes; then 98 microliters DMEM (with 10% FBS, 1% penicillin and streptomycin) was added to the DNA:Fugene 6 reagent complex and mixed gently. After incubating the cells for 24 hours at 37 degrees Celcius in 5% $CO_2$, fresh media and test compounds were added to the wells and the cells further incubated for 15 hours at 37 degrees Celcius in 5% $CO_2$. Finally, 10 ng/ml TNF-α was added and the cells further incubated for 4 hours. Cells were lysed by adding 80 microliters/well of a cell culture lysis reagent (Promega). 50 microliters of each lysate was taken for GFP detection using an excitation wavelength of 486 nm and detection at 527 nm. 100 microliters Luciferase assay reagent (Promega) was then added to every 20 microliters cell lysate for luminometer detection. The compounds of the instant invention described in the Examples and Tables above exhibit differential induction of p21 versus klf2 of 0.1 to 5.5-fold at 10 micromolar concentration. p21 versus klf2 selectivity for specific representative compounds can be found in Table 4.

Example 39

Antiproliferative Activity Against Cancer Cell Lines by Novel Compounds

The novel compounds of the present invention were tested for their ability to inhibit growth of various cancer cell lines (HeLa, MCF7, U2OS, HepG2, HL60, HCT-116) using in vitro growth inhibition assays described below.

MTS Assay

Cells were seeded in 96-well culture plates (200 microliters/well at different seeding concentrations depending on cell type) and incubated overnight at 37 degrees Celcius in 5% $CO_2$. After adding compound dilutions to the cells (DMSO concentration kept below 0.5%), the cells were incubated at 37 degrees Celcius in 5% $CO_2$ for 72 hours. The effects on proliferation were determined by addition of MTS reagent (Promega) according to the manufacturer's instruction, followed by incubation for 2 hours at 37 degrees Celcius in 5% $CO_2$, and finally recording the absorbance at 490 nm using an ELISA plate reader.

WST Assay

Similar to MTS assay except that the developer is the CCK-8 reagent (Dojindo) and the plate reader is set to 450 nm absorbance.

The compounds of the instant invention described in the Examples and Tables above inhibited growth of the abovementioned cancer cell lines with 72 hour $GI_{50}$ values in the range of about 100 nanomolar to greater than 30 micromolar. $GI_{50}$ values against HCT-116 colon cancer cells for specific representative compounds can be found in Table 4.

TABLE 4

Biological activity data for selected examples from the present invention.

| Example | HDAC (RP30) | p21 (RP3) | p21/klf2 (RP3) | p21/klf2 (RP10) | GI50 (micromolar) HCT116 |
|---|---|---|---|---|---|
| 4-1 | 178% | 300% | 1.4 | 5.5 | 0.7 |
| 4-2 | 169% | 324% | 2.2 | 3.6 | 0.7 |
| 4-3 | 162% | 99% | 0.8 | 1.2 | 1.0 |
| 4-4 | 162% | 125% | 1.2 | 3.1 | 1.1 |
| 4-5 | 156% | 241% | 1.2 | 4.5 | 0.8 |
| 4-6 | 152% | 184% | 1.4 | 3.0 | 0.6 |
| 4-12 | 130% | 167% | 10.6 | 0.8 | 0.4 |
| 4-14 | 128% | 84% | 1.2 | 5.1 | 0.6 |
| 4-22 | 119% | 103% | 1.8 | 2.0 | 1.2 |
| 4-24 | 118% | 162% | 1.5 | 1.5 | 2.1 |
| 4-29 | 117% | 48% | 0.6 | 2.3 | 2.1 |
| 4-31 | 114% | 178% | 1.2 | 1.2 | 0.2 |
| 4-35 | 112% | 140% | 2.0 | 3.0 | 1.3 |
| 4-36 | 111% | 43% | 0.7 | 3.1 | 2.0 |
| 4-37 | 110% | 60% | 1.1 | 1.7 | 1.0 |
| 4-41 | 107% | 156% | 3.5 | 2.1 | 1.4 |
| 4-43 | 106% | 89% | 0.9 | 2.1 | 2.2 |
| 4-47 | 104% | 79% | 1.0 | 1.8 | 0.9 |
| 4-48 | 104% | 130% | 1.9 | 1.9 | 1.4 |
| 4-49 | 98% | 128% | 1.5 | 1.5 | 1.4 |
| 4-68 | 117% | 41% | 0.5 | 1.3 | 3.7 |
| 4-69 | 112% | 117% | 1.0 | 2.3 | 1.7 |
| 9-1 | 174% | 144% | 1.0 | 2.2 | 1.0 |
| 9-3 | 140% | 152% | 1.6 | 1.7 | 0.3 |
| 9-6 | 134% | 47% | 0.9 | 1.7 | 2.7 |
| 9-7 | 132% | 54% | 0.5 | 2.1 | 2.5 |
| 9-10 | 131% | 80% | 1.0 | 1.6 | 1.1 |
| 9-11 | 131% | 97% | 1.1 | 2.7 | 0.9 |
| 9-17 | 117% | 84% | 1.3 | 1.9 | 1.9 |
| 9-18 | 115% | 70% | 1.0 | 1.7 | 1.0 |
| 9-28 | 89% | 33% | 0.5 | 0.9 | 1.8 |
| 9-29 | 88% | 10% | 0.3 | 0.5 | 7.1 |
| 19 | 104% | 98% | 1.6 | 3.6 | 2.2 |
| 30 | 90% | 100% | 1.3 | 3.9 | 0.8 |
| 30-33 | 100% | 193% | 2.1 | 1.2 | 0.9 |
| 30-54 | 89% | 183% | 2.0 | 1.3 | 1.0 |

HDAC (RP30) is the relative inhibitory potency compared with SNDX-275 at 30 micromolar; p21 (RP3) is the relative induction potency compared with SNDX-275 at 3 micromolar; p21/klf2 (RP3) is the relative selectivity at 3 micromolar compared with SNDX-275 (p21/klf2 ratio defined as 1.0); p21/klf2 (RP10) is the relative selectivity at 10 micromolar compared with SNDX-275 (p21/klf2 ratio defined as 1.0).

(RP3) is the relative selectivity at 3 micromolar compared with SNDX-275 (p21/klf2 ratio defined as 1.0); p21/klf2 (RP10) is the relative selectivity at 10 micromolar compared with SNDX-275 (p21/klf2 ratio defined as 1.0).

The invention claimed is:

1. A compound of formula (I),

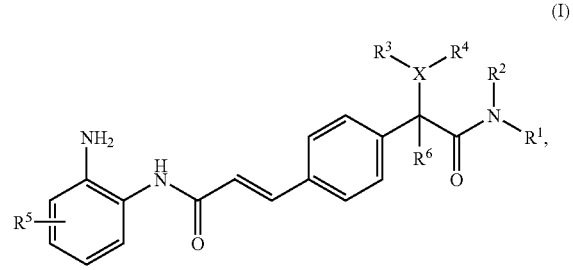

(I)

wherein:
X is —N—;
$R^1$ is hydrogen;
$R^2$ is selected from the group consisting of:
  hydrogen;
  $C_{1-6}$ alkyl, which is unsubstituted or substituted by morpholino;
  —$(CH_2)_k$-phenyl;
  —$(CH_2)_k$-pyridinyl;
  —$(CH_2)_k$-benzotriazolyl;
  —$(CH_2)_k$-cyclohexyl; and
  —$(CH_2)_k$-heterocyclyl, wherein said heterocyclyl is 6 membered and one or two ring atoms are, individually, oxygen, nitrogen or sulphur;
  and wherein all of the aforementioned cyclic groups are unsubstituted or one or two times substituted by halogen, cyano, trifluoromethyl, trifluoromethoxy, $C_{1-6}$ alkyl or $C_{3-6}$ cycloalkyl; and
$R^3$ and $R^4$ are:
each independently selected from the group consisting of:
  hydrogen;
  a 5 to 10 membered, mono- or bicyclic aryl, wherein the ring may be unsubstituted or one or two times substituted by hydroxyl, cyano, halogen, trifluoromethyl, trifluoromethoxy, cyclopropyl, $C_{1-4}$ alkyl, $C_{1-4}$ alkoxy, —$N(C_{1-4}$ alkyl$)_2$ or —$NH(C_{1-4}$alkyl);
  a 5 to 10 membered, mono- or bicyclic heteroaryl wherein 1 or 2 ring atoms are, individually, oxygen, nitrogen or sulphur, and wherein the ring may be unsubstituted or one or two times substituted by hydroxyl, cyano, halogen, trifluoromethyl, trifluoromethoxy, cyclopropyl, $C_{1-4}$ alkyl, $C_{1-4}$ alkoxy, —$N(C_{1-4}$ alkyl$)_2$ or —$NH(C_{1-4}$alkyl);
  a $C_{3-8}$ cycloalkyl; and
  a $C_{1-6}$ alkyl which is unsubstituted or substituted by —OH; —O—$C_{1-6}$ alkyl; —$N(C_{1-6}$ alkyl$)_2$; —NH($C_{1-6}$ alkyl); —N—C(O)—$C_{1-6}$ alkyl; —C(O)-morpholino;
  —C(O)—$C_{1-6}$ alkyl; a 5 to 10 membered, mono- or bicyclic aryl which is optionally substituted with methyl or —C(O)—$CH_3$; a 15 to 10 membered, mono- or bicyclic heteroaryl wherein 1, 2 or 3 ring atoms are, individually, oxygen, nitrogen or sulphur, and which is optionally substituted with methyl or
  —C(O)—$CH_3$; a 3 to 8 membered, mono- or bicyclic cycloalkyl which is optionally substituted with methyl or —C(O)—$CH_3$; or a 3 to 8 membered, mono- or bicyclic heterocyclyl wherein 1, 2 or 3 ring atoms are, individually, oxygen, nitrogen or sulphur, and which is optionally substituted with methyl or —C(O)—CH$_3$; or $R^3$ and $R^4$, together with the nitrogen atom to which they are attached, form a 4- to 6-membered heterocyclyl wherein one ring atom, other than X, may be oxygen or nitrogen;

$R^5$ and $R^6$ are each hydrogen; and k is 0, 1, 2 or 3;

or a pharmaceutically acceptable salt thereof.

2. A compound of formula (I) according to claim 1, wherein:

X is —N—;

$R^1$, $R^5$ and $R^6$ are each hydrogen;

$R^2$ is phenyl or pyridinyl, which are either unsubstituted or one or two times substituted by a substituent selected from the group consisting of: halogen; cyano; trifluoromethyl; trifluoromethoxy; C$_{1-6}$ alkyl; and C$_{3-6}$ cycloalkyl; and $R^3$ is hydrogen and $R^4$ is:

phenyl, which is unsubstituted or substituted by halogen; or a C$_{1-6}$ alkyl, which is unsubstituted or once substituted by a substituent selected from the group consisting of:

—N(C$_{1-6}$ alkyl)$_2$;

—NH(C$_{1-6}$ alkyl);

—OH; and a 5 to 7 membered, mono- or bicyclic heterocyclyl, wherein one or two ring atoms are, individually, nitrogen, oxygen or sulphur; or $R^3$ and $R^4$, together with the nitrogen atom to which they are attached, form a 5- to 6-membered heterocyclyl wherein one ring atom, other than X, may be oxygen;

or a pharmaceutically acceptable salt thereof.

3. A pharmaceutical composition comprising a compound according to claim 1 and a pharmaceutically acceptable adjuvant.

4. A method for the treatment of colon cancer, comprising administering, to a patient in need of such treatment, a compound according to claim 1.

* * * * *

UNITED STATES PATENT AND TRADEMARK OFFICE
CERTIFICATE OF CORRECTION

PATENT NO. : 7,795,315 B2
APPLICATION NO. : 12/358348
DATED : September 14, 2010
INVENTOR(S) : Li Chen et al.

It is certified that error appears in the above-identified patent and that said Letters Patent is hereby corrected as shown below:

Claim 1, column 150, line 59, delete "15" and insert -- 5 --.

Signed and Sealed this

Thirtieth Day of November, 2010

David J. Kappos
*Director of the United States Patent and Trademark Office*